United States Patent
Quibell et al.

(10) Patent No.: US 8,008,290 B2
(45) Date of Patent: Aug. 30, 2011

(54) COMPOUNDS

(75) Inventors: Martin Quibell, Madingley (GB); John P. Watts, Madingley (GB); Nicholas S. Flinn, Madingley (GB)

(73) Assignee: Amura Therapeutics Limited, Cambridge (GB)

(*) Notice: Subject to any disclaimer, the term of this patent is extended or adjusted under 35 U.S.C. 154(b) by 0 days.

(21) Appl. No.: 12/852,998

(22) Filed: Aug. 9, 2010

(65) Prior Publication Data

US 2011/0009385 A1     Jan. 13, 2011

Related U.S. Application Data

(63) Continuation of application No. PCT/GB2009/000672, filed on Mar. 11, 2009.

(51) Int. Cl.

| | |
|---|---|
| A61K 31/407 | (2006.01) |
| A61K 31/422 | (2006.01) |
| A61K 31/4155 | (2006.01) |
| A61K 31/4178 | (2006.01) |
| A61K 31/427 | (2006.01) |
| A61K 31/4523 | (2006.01) |
| A61K 31/4709 | (2006.01) |
| A61K 31/496 | (2006.01) |
| A61K 31/5377 | (2006.01) |
| C07D 223/16 | (2006.01) |
| C07D 241/52 | (2006.01) |
| C07D 491/048 | (2006.01) |

(52) U.S. Cl. ........ 514/213.01; 514/230.5; 514/312; 514/254.08; 514/338; 514/403; 514/374; 514/359; 514/406; 514/367; 514/381; 514/382; 514/397; 548/453; 548/253; 548/311.7; 548/159; 548/154; 548/364.4; 548/261; 548/235; 548/362.5; 546/276.7; 546/158; 544/353; 544/373; 544/105; 340/593

(58) Field of Classification Search .......... None
See application file for complete search history.

(56) References Cited

FOREIGN PATENT DOCUMENTS

WO    WO 02057270 A1 *  7/2002
WO    WO 2008/007127 A1   1/2008

OTHER PUBLICATIONS

Hackh's Chemical Dictionary, 5th ed. McGraw-Hill, Inc., 1987.*
Byrn et al. Solid-State Chemistry of Drugs, 2d, Chapter 11 Hydrates and Solvates, 233-247 (1999).*
Morissette et al. Adv. Drug Delivery Rev. 56:274 (2004).*
Rouhi, Chem. & Eng. News, Feb. 24, 2003, 81(8), 32-35.*
International Preliminary Report on Patentability PCT/GB2009/000672 (Parent), May 24, 2010.

* cited by examiner

Primary Examiner — Yong Chu
Assistant Examiner — Michael Barker
(74) Attorney, Agent, or Firm — Edwards Angell Palmer & Dodge LLP; Kathleen Williams; Weiying Yang

(57) ABSTRACT

A first aspect of the invention relates to a compound of formula (I), or a pharmaceutically acceptable salt, hydrate, complex or pro-drug thereof,

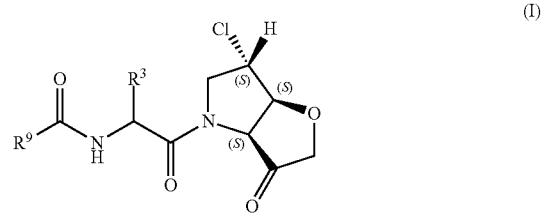

wherein:
$R^3$ is selected from cyclopentyl and cyclohexyl;
$R^9$ is a substituted 5 or 6-membered aryl or heteroaryl group or a 6,5- or 6,6-fused biaryl or heterobiaryl group.
Compounds of formula (I) exhibit surprisingly high dual efficacies for human cathepsin S and K and are useful for the treatment of rheumatoid arthritis, osteoarthritis, chronic obstructive pulmonary disease (COPD), atherosclerosis, cardiovascular diseases which exhibit significant damage and remodeling of extracellular matrix (ECM) and chronic pain.

39 Claims, No Drawings

COMPOUNDS

RELATED APPLICATIONS

This present invention is a continuation patent application which claims priority to PCT patent application number PCT/GB2009/000672, filed Mar. 11, 1009, which claims priority to Great Britain patent application number 0804702.9, filed Mar. 13, 2008, the entirety of which are herein incorporated by reference.

The present invention relates to compounds that are inhibitors of cysteine proteinases, pharmaceutical compositions containing said compounds, and their use in therapy. More specifically, the invention relates to compounds that are dual inhibitors of cathepsin S and cathepsin K, which are cysteine proteinases of the CA clan. Such compounds are particularly useful for the in vivo therapeutic treatment of diseases in which participation of cathepsin S and cathepsin K are implicated.

BACKGROUND TO THE INVENTION

Proteinases form a substantial group of biological molecules which to date constitute approximately 2% of all the gene products identified following analysis of several completed genome sequencing programmes. Proteinases have evolved to participate in an enormous range of biological processes, mediating their effect by cleavage of peptide amide bonds within the myriad of proteins found in nature. This hydrolytic action is performed by initially recognising, then binding to, particular three-dimensional electronic surfaces displayed by a protein, which align the bond for cleavage precisely within the proteinase catalytic site. Catalytic hydrolysis then commences through nucleophilic attack of the amide bond to be cleaved either via an amino acid side-chain of the proteinase itself, or through the action of a water molecule that is bound to and activated by the proteinase. Proteinases in which the attacking nucleophile is the thiol side-chain of a Cys residue are known as cysteine proteinases. The general classification of 'cysteine proteinase' contains many members found in a wide range of organisms from viruses, bacteria, protozoa, plants and fungi to mammals. Cathepsins S and K and indeed many other crucial mammalian proteinases belong to the papain-like CAC1 family (see Barrett, A. J et al, in 'Handbook of Proteolytic Enzymes', Eds. Barrett, A. J., Rawlings, N. D., and Woessner, J. F. Publ. Academic Press, 1998, for a thorough discussion).

To date, cysteine proteinases have been classified into five clans, CA, CB, CC, CD and CE (Barrett, A. J. et al, 1998). A proteinase from the tropical papaya fruit 'papain' forms the foundation of clan CA, which currently contains over 80 distinct and complete entries in various sequence databases, with many more expected from the current genome sequencing efforts. Proteinases of clan CA/family C1 have been implicated in a multitude of house-keeping roles and disease processes. e.g. human proteinases such as cathepsin K (osteoporosis, osteoarthritis), cathepsin S (multiple sclerosis, rheumatoid arthritis, autoimmune disorders), cathepsin L (metastases), cathepsin B (metastases, arthritis), cathepsin F (antigen processing), cathepsin V (T-cell selection), dipeptidyl peptidase I (granulocyte serine proteinase activation) or parasitic proteinases such as falcipain (malaria parasite *Plasmodium falciparum*) and cruzipain (*Trypanosoma cruzi* infection).

There currently exists a major unmet need for safe orally administered medications for the treatment of inflammatory diseases such as rheumatoid arthritis, osteoarthritis, chronic obstructive pulmonary disease (COPD) and cardiovascular disease, which exhibit significant damage and remodeling of extracellular matrix (ECM). Destruction of the ECM is brought about through proteolysis of its elastin, collagen and proteoglycan constituents, which provide structure, elasticity and tensile strength to materials such as cartilage, bone, lung and vascular tissue. The proteolytic enzymes cathepsin S and cathepsin K are up-regulated under inflammatory conditions and have been implicated in the degradation of ECM components.

Cathepsins K and S are found over-expressed in rheumatoid and osteoarthritic synovium and have been shown to degrade collagen type-I and type-II, as well as aggrecan (a multidomain proteoglycan component of articular cartilage) respectively (see Hou, W. S. et al., Arthritis & rheumatism, 46 (3). 663-674, 2002; Hou, W. S. et al., Biol Chem, 384. 891-897, 2003 & Yasuda, Y. et al., Adv Drug Del Rev, 57. 973-993, 2005 and references cited herein). In addition, transgenic mice overexpressing cathepsin K, show spontaneous development of synovitis and cartilage degeneration (see Morko, J. et al., Arthritis & rheumatism, 52 (12). 3713-3717, 2005). Cathepsin S is also known to play a role in auto-antigen presentation in rheumatoid arthritis, helping prime the immune system to attack self-tissues in susceptible joints (e.g. see Podolin, P. L., et al., inflamm Res, 50:S159.2001).

As well as destruction of articular cartilage, cathepsin S and cathepsin K demonstrate potent elastinolytic activity and are involved in a broad spectrum of pathological conditions associated with elastin degradation, such as COPD and cardiovascular disease. Both enzymes are readily secreted by macrophages and smooth muscle cells and have been shown to degrade elastins from bovine aorta and lung tissue. Furthermore, in a murine model of COPD/emphysema, induced by IL-13, Cathepsin S and K were shown to be present in the diseased lung tissue and infiltrating macrophage and disease symptoms were abrogated by cysteine proteinase inhibitors (see Wolters, P. J. and Chapman, H. A., Respir Res, 1. 170-177, 2000; Novinec, M. et al., J Biol Chem, 282 (11). 7893-7902, 2007; Zheng, T. et al., J Clin Invest, 106. 1081-1093, 2000). Cathepsins S and K are also responsible for the vascular tissue damage associated with chronic cardiovascular disease and vascular injury. In murine models of atherosclerosis, Cathepsin S has been found in abundance, in atherosclerotic plaques (secreted from infiltrating macrophage) and induces plaque rupture (see Rodgers, K. J. et al., Arterioscler Thromb Vasc Biol, 26 (4):851-856, 2006). Cathepsin K and cathepsin S have been associated with vascular remodeling and causing ECM damage during the development of atherosclerosis and vascular injury-induced neointimal formation (see Cheng, X. W. et al., Am J Pathol, 164 (1). 243-251, 2004). While both enzymes are involved in the growth and rupture of abdominal aortic aaneurysms (see Abdul-Hussien, H. et al., Am J Pathol, 170 (3). 809-817, 2007).

Thus inhibition of cathepsins K and S offer an attractive approach to prevent the underlying tissue destruction which occurs in chronic inflammatory diseases such as rheumatoid arthritis, osteoarthritis, COPD and cardiovascular disease.

In the prior art, the development of cysteine proteinase inhibitors for human use has recently been an area of intense activity (e.g. see Deaton, D. N. and Kumar, S., Prog. Med. Chem. 42, 245-375, 2004; Bromme, D. and Kaleta, J., Curr. Pharm. Des., 8, 1639-1658, 2002; Kim, W. and Kang, K., Expert Opin. Ther. Patents, 12 (3), 419-432, 2002; Leung-Toung, R. et al. Curr. Med. Chem., 9, 979-1002, 2002; Lecaille, F. et al., Chem. Rev., 102, 4459-4488, 2002; Hernandez, A. A. and Roush, W. R., Curr. Opin. Chem. Biol., 6, 459-465, 2002; Link, J. O. and Zipfel, S. Curr. Opin. Drug Discov. Dev., 9 (4), 471-482, 2006). Considering the CAC1 family members, particular emphasis has been placed upon the development of inhibitors of human cathepsins, primarily cathepsin K (osteoporosis) and cathepsin S (autoimmune disorders) through the use of covalent-bound but reversible peptide and peptidomimetic nitriles (e.g. see Bekkali, Y. et al, Bioorg. Med. Chem. Lett., 17 (9), 2465-2469, 2007; WO-A-07137738, WO-A-07003056), linear and cyclic peptide and peptidomimetic ketones (e.g. see Veber, D. F. and Thompson, S. K., Curr. Opin. Drug Discovery Dev., 3 (4), 362-369, 2000; WO-A-02057270, WO-A-04007501, WO-A-06064286, WO-A-05066180, WO-A-0069855), ketoheterocycles (e.g. see Palmer, J. T. et al, Bioorg. Med. Chem. Lett., 16 (11), 2909-2914, 2006, WO-A-04000838), α-ketoamides (e.g. see WO-A-06102243), cyanamides (WO-A-01077073, WO-A-01068645) and arylnitriles (e.g. see WO-A-07080191, WO-A-07039470, WO-A-06018284, WO-A-05121106, WO-A-04000843). Inhibition of CAC1 proteases by non-covalent bound compounds has been extensively described in the literature. Particular emphasis has been placed upon inhibition of cathepsin K and cathepsin S by arylaminoethylamides (e.g. see Altmann, E., et al, J. Med. Chem., 45 (12), 2352-2354, 2002; Chatterjee, A. K. et al, Bioorg. Med. Chem. Lett., 17 (10), 2899-2903, 2007; US-20050113356, US-20050107368, US-20050118568) and substituted pyrazoles or piperidines (e.g. see Wei, J., et al, Bioorg. Med. Chem. Lett., 17 (20), 5525-5528, 2007; US-2007117785, US-2003073672, WO-A-02020013).

Thus the extensive prior art describes potent in vitro inhibitors of either cathepsin S or cathepsin K and inhibitors showing efficacy in numerous animal models of disease. However, since these enzymes appear to work in tandem and both are present in many chronic inflammatory diseases, a single compound possessing dual inhibitory activity would be a distinct advantage. There are presently no human therapeutic dual inhibitors of cathepsin K and S.

Recently, Quibell, M. (WO-A-02057270) described a new motif for the general inhibition of CAC1 proteinases based upon a cis-5,5-bicyclic ketone (1).

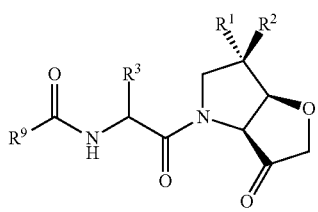

(1)

Based upon this motif, highly potent and selective inhibitors of cathepsin K were discovered (see WO-A-0807109, WO-A-0807103, WO-A-0807130, WO-A-0807114, WO-A-0807127, WO-A-0807107, WO-A-0807112). The present inventors have now discovered a small genus of 6-(S)-chlorotetrahydrofuro[3,2-b]pyrrol-3-ones that exhibit potent dual inhibition versus human cathepsins S and K.

STATEMENT OF INVENTION

A first aspect of the invention relates to a compound of formula (I), or a pharmaceutically acceptable salt, hydrate, complex or pro-drug thereof,

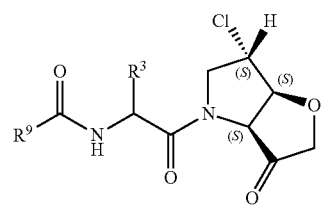

(I)

wherein:
$R^3$ is selected from cyclopentyl and cyclohexyl;
$R^9$ is selected from the following:

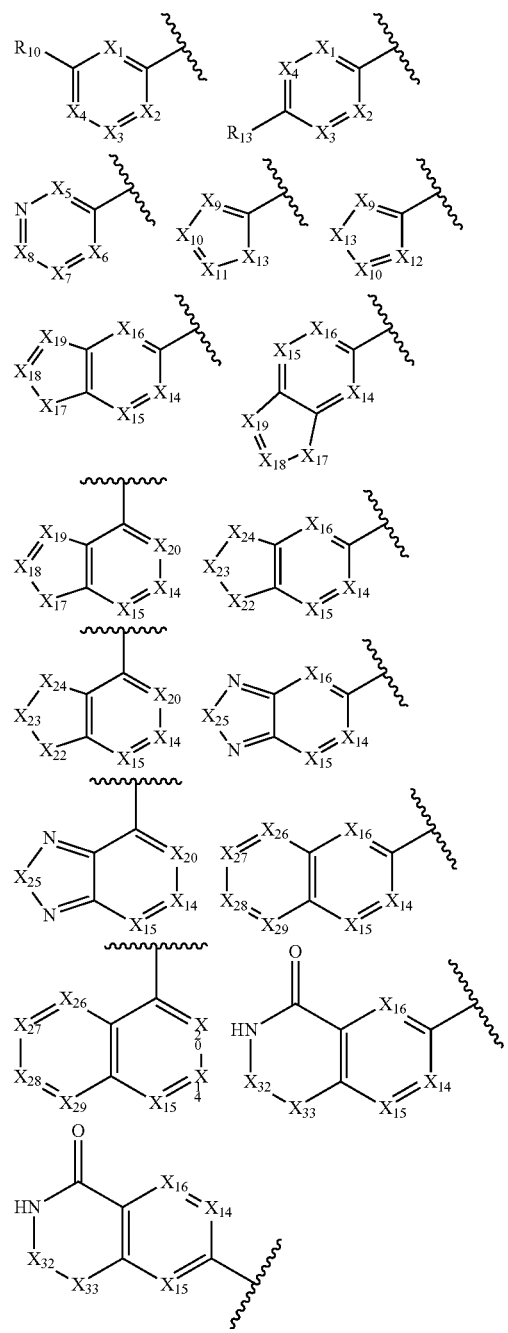

-continued

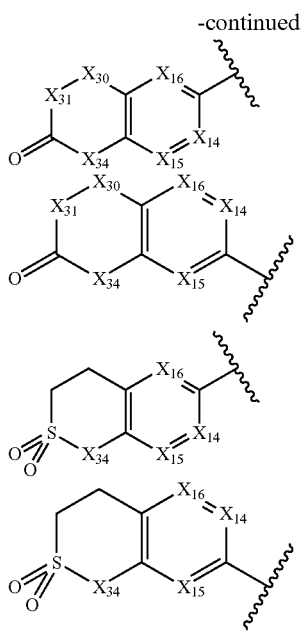

wherein:
$X_1, X_2, X_3, X_4, X_{14}, X_{15}, X_{16}$ and $X_{20}$ are each independently selected from:
  CH, C—($C_{1-6}$-alkyl), C—($C_{1-6}$-alkoxy), C-halo and N;
such that a maximum of two of $X_1, X_2, X_3, X_4, X_{14}, X_{15}, X_{16}$ and $X_{20}$ are selected from N, C-halo and C—($C_{1-6}$-alkoxy);
$X_5, X_6, X_7$ and $X_8$ are each independently selected from:
  CH, C—($C_{1-6}$-alkyl), C—($C_{1-6}$-alkoxy), C-halo, N and C—OH;
such that a maximum of one of $X_5, X_6, X_7$ and $X_8$ is N, C-halo, C—OH or C—($C_{1-6}$-alkoxy);
$X_9$ and $X_{12}$ are each independently selected from:
  CH, C—($C_{1-6}$-alkyl), C—($C_{1-6}$-alkoxy), C-halo and N;
$X_{10}$ and $X_{11}$ are each independently selected from:
  CH, C—($C_{1-6}$-alkyl), C—($C_{1-6}$-alkoxy), C-halo, N and $R_{10}$;
$X_{19}$ is selected from:
  CH, C—($C_{1-6}$-alkyl), C—($C_{1-6}$-alkoxy), C—C(O)NH$_2$, C—C(O)NH($C_{1-6}$-alkyl), C—C(O)N($C_{1-6}$-alkyl)$_2$, C-halo and N;
$X_{18}$ is selected from:
  CH, C—($C_{1-6}$-alkyl), C—($C_{1-6}$-alkoxy), C—NH$_2$, C—N($C_{1-6}$-alkyl)$_2$, C—NH($C_{1-6}$-alkyl), C—NHC(O)$C_{1-6}$-alkyl, C-halo and N;
  or when $X_{19}$ is CH, C—($C_{1-6}$-alkyl), or C-halo then $X_{18}$ may additionally be selected from C—C(O)NH$_2$ and C—C(O)N($C_{1-6}$-alkyl)$_2$;
$X_{13}$ and $X_{17}$ are each independently selected from:
  O, S, NH and N—($C_{1-6}$-alkyl);
$X_{22}$ and $X_{24}$ are each independently selected from:
  CH$_2$, CH—($C_{1-6}$-alkyl), O, S, NH, NMe and )C=O;
$X_{23}$ is selected from:
  CH$_2$, CH—($C_{1-6}$-alkyl), C—($C_{1-6}$-alkyl)$_2$, NH and NMe;
  or when either $X_{22}$ or $X_{24}$ are other than )C=O then $X_{23}$ may additionally be )C=O or )S(O)$_2$;
$X_{25}$ is selected from:
  O, S, NH and N($C_{1-6}$-alkyl);
$X_{26}, X_{27}, X_{28}$ and $X_{29}$ are each independently selected from:
  CH, C—($C_{1-6}$-alkyl), C—($C_{1-6}$-alkoxy), C—OH, C-halo and N;
such that a maximum of two of $X_{26}, X_{27}, X_{28}$ and $X_{29}$ are selected from C—($C_{1-6}$-alkoxy), C—OH, C-halo and N;
$X_{30}$ is selected from:
  CH$_2$, CH$_2$CH$_2$, NH, NMe, O, S and )C=O;
$X_{31}$ is selected from:
  CH$_2$, NH and NMe;
  or when $X_{30}$ is other than )C=O, O or S then $X_{31}$ may additionally be )C=O or O;
$X_{32}$ is selected from:
  CH$_2$, CH$_2$CH$_2$, NH, NMe and )C=O;
$X_{33}$ is selected from:
  CH$_2$, NH and NMe;
  or when $X_{32}$ is other than )C=O then $X_{33}$ may additionally be )C=O or O;
$X_{34}$ is selected from:
  NH and NMe;
$R_{10}$ is selected from:

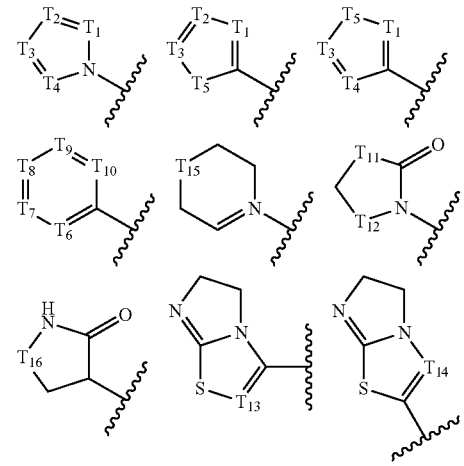

wherein:
$T_1, T_2, T_3$ and $T_4$ are each independently selected from:
  CH, C—($C_{1-6}$-alkyl), C—($C_{1-6}$-alkoxy), C—NH$_2$, C—NH($C_{1-6}$-alkyl), C—N($C_{1-6}$-alkyl)$_2$, C-halo and N;
such that a maximum of one of $T_1, T_2, T_3$ and $T_4$ is C—($C_{1-6}$-alkoxy), C—NH$_2$, C—NH($C_{1-6}$-alkyl), C—N($C_{1-6}$-alkyl)$_2$ or C-halo;
$T_5$ is selected from:
  O, S, NH and N($C_{1-6}$-alkyl);
$T_6, T_7, T_8, T_9$ and $T_{10}$ are each independently selected from:
  CH, C—($C_{1-6}$-alkyl), C—($C_{1-6}$-alkoxy), C—NH$_2$, C—NH($C_{1-6}$-alkyl), C—N($C_{1-6}$-alkyl)$_2$, C-halo and N;
such that a maximum of two of $T_6, T_7, T_8, T_9$ and $T_{10}$ are selected from C—($C_{1-6}$-alkoxy), C—NH$_2$, C—NH($C_{1-6}$-alkyl), C—N($C_{1-6}$-alkyl)$_2$, C-halo and N;
$T_{11}$ is selected from:
  CH$_2$, NH and N($C_{1-6}$-alkyl);
$T_{12}$ is selected from:
  CH$_2$, NH, N($C_{1-6}$-alkyl) and )C=O;
$T_{13}$ and $T_{14}$ are each independently selected from:
  CH, C—($C_{1-6}$-alkyl) and C-halo;
$T_{15}$ is selected from:
  O, NH and N($C_{1-6}$-alkyl);
$T_{16}$ is selected from:
  CH$_2$ and )C=O;

or $R_{10}$ is selected from:

H, $C_{1-6}$-alkyl, OH, $C_{1-6}$-alkoxy, $NO_2$, halo, CN, $C(O)NH_2$, $C(O)NH(C_{1-6}$-alkyl), $C(O)N(C_{1-6}$-alkyl)$_2$, $C(O)NH(C_{3-6}$-cycloalkyl), $S(O)_2NH_2$, $S(O)_2(C_{1-6}$-alkyl), $S(O)_2NH(C_{1-6}$-alkyl), $S(O)_2N(C_{1-6}$-alkyl)$_2$, $S(O)_2NH(C_{3-6}$-cycloalkyl) and $(CH_2)_n$—$NR^{11}R^{12}$;

wherein n is 0 or 1;

and $R^{11}$ is selected from $C_{1-6}$-alkyl, $C(O)C_{1-6}$-alkyl, $C(O)(C_{3-6}$-cycloalkyl), $C(O)$(aryl), $C(O)NH_2$, $C(O)NH(C_{1-6}$-alkyl), $C(O)N(C_{1-6}$-alkyl)$_2$, $C(O)NH(C_{3-6}$-cyclo alkyl), $C(O)O(C_{1-6}$-alkyl), $C(O)O(C_{3-6}$-cycloalkyl), $C(O)O$(aryl), $S(O)_2(C_{1-6}$-alkyl), $S(O)_2(C_{3-6}$-cycloalkyl), $S(O)_2NH_2$, $S(O)_2NH(C_{1-6}$-alkyl), $S(O)_2N(C_{1-6}$-alkyl)$_2$, $S(O)_2NH(C_{3-6}$-cycloalkyl) and $S(O)_2$(aryl);

and $R^{12}$ is selected from H and $C_{1-6}$-alkyl.

$R_{13}$ is selected from:

$C(O)NH_2$, $C(O)NH(C_{1-6}$-alkyl), $C(O)N(C_{1-6}$-alkyl)$_2$, $C(O)NH(C_{3-6}$-cycloalkyl), $S(O)_2NH_2$, $S(O)_2(C_{1-6}$-alkyl), $S(O)_2NH(C_{1-6}$-alkyl), $S(O)_2N(C_{1-6}$-alkyl)$_2$, $S(O)_2NH(C_{3-6}$-cycloalkyl) and $(CH_2)_n$—$NR^{14}R^{15}$;

wherein n is 0 or 1;

and $R^{14}$ is selected from H, $C_{1-6}$-alkyl, $C(O)C_{1-6}$-alkyl, $C(O)(C_{3-6}$-cycloalkyl), $C(O)$(aryl), $C(O)NH_2$, $C(O)NH(C_{1-6}$-alkyl), $C(O)N(C_{1-6}$-alkyl)$_2$, $C(O)NH(C_{3-6}$-cycloalkyl), $C(O)O(C_{1-6}$-alkyl), $C(O)O(C_{3-6}$-cycloalkyl), $C(O)O$(aryl), $S(O)_2(C_{1-6}$-alkyl), $S(O)_2(C_{3-6}$-cycloalkyl), $S(O)_2NH_2$, $S(O)_2NH(C_{1-6}$-alkyl), $S(O)_2N(C_{1-6}$-alkyl)$_2$, $S(O)_2NH(C_{3-6}$-cycloalkyl) and $S(O)_2$(aryl);

and $R^{15}$ is selected from H and $C_{1-6}$-alkyl.

Compounds of formula (I) exhibit surprisingly high dual potency for human cathepsins S and K.

A second aspect of the invention relates to a pharmaceutical or veterinary composition comprising a compound of formula (I) and a pharmaceutically acceptable or veterinarily acceptable diluent, excipient and/or carrier.

A third aspect of the invention relates to a process for preparing a pharmaceutical or veterinary composition as defined above, said process comprising admixing a compound of the invention with a pharmaceutically acceptable or veterinarily acceptable diluent, excipient and/or carrier.

A fourth aspect of the invention relates to compounds of formula (I) for use in medicine.

A fifth aspect of the invention relates to the use of a compound of formula (I) in the preparation of a medicament for treating a disease selected from rheumatoid arthritis, osteoarthritis, chronic obstructive pulmonary disease (COPD), atherosclerosis, cardiovascular diseases which exhibit significant damage and remodeling of extracellular matrix (ECM) and chronic pain.

A sixth aspect of the invention relates to a method of inhibiting cathepsin S and cathepsin K in a cell, said method comprising contacting said cell with a compound of formula (I).

A seventh aspect of the invention relates to method of inhibiting cathepsin S and cathepsin K in a subject, said method comprising administering to the subject a pharmacologically effective amount of a compound of formula (I).

An eighth aspect of the invention relates to a method of treating a disease selected from rheumatoid arthritis, osteoarthritis, chronic obstructive pulmonary disease (COPD), atherosclerosis, cardiovascular diseases which exhibit significant damage and remodeling of extracellular matrix (ECM) and chronic pain, in a subject, said method comprising administering to the subject a pharmacologically effective amount of a compound of formula (I).

A ninth aspect of the invention relates to the use of a compound according to the invention in an assay for identifying further candidate compounds capable of inhibiting one or more cysteine proteinases.

A tenth aspect of the invention relates to the use of a compound of formula (I) in the validation of a known or putative cysteine proteinase as a therapeutic target.

An eleventh aspect of the invention relates to a process of preparing a compound of formula (I).

A twelfth aspect of the invention relates to a compound of formula (I) for treating a disease selected from rheumatoid arthritis, osteoarthritis, chronic obstructive pulmonary disease (COPD), atherosclerosis, cardiovascular diseases which exhibit significant damage and remodeling of extracellular matrix (ECM) and chronic pain.

DETAILED DESCRIPTION

The term 'alkyl' as applied herein includes stable straight and branched chain aliphatic carbon chains which may be optionally substituted. Preferred examples include methyl, ethyl, n-propyl, isopropyl, n-butyl, isobutyl, t-butyl, pentyl, isopentyl, hexyl, heptyl and any simple isomers thereof. Suitable substituents include, for example, one or more $C_{1-6}$ alkoxy, OH, COOH, COOMe, $NH_2$, $NMe_2$, NHMe, $NO_2$, CN and/or $CF_3$ groups. Additionally, where the alkyl group contains two or more contiguous carbon atoms, an alkene group (—CH═CH—) or alkyne group (—C≡C—) may be present. Furthermore, the alkyl group may optionally contain one or more heteroatoms for example, to give ethers, thioethers, sulphones, sulphonamides, substituted amines, amidines, guanidines, carboxylic acids, carboxamides. If the heteroatom is located at a chain terminus then it is appropriately substituted with one or two hydrogen atoms. For example, the group $CH_3$—$CH_2$—O—$CH_2$—$CH_2$— is defined within 'alkyl' as a $C_4$ alkyl that contains a centrally positioned heteroatom whereas the group $CH_3$—$CH_2$—$CH_2$—$CH_2$— is defined within 'alkyl' as an unsubstituted $C_4$ alkyl. Preferably, the alkyl group is a $C_{1-6}$ alkyl group, more preferably a $C_{1-4}$ group.

The term 'cycloalkyl' as applied herein refers to a cyclic alkyl group (i.e. a carbocyclic ring) which may be substituted (mono- or poly-) or unsubstituted. Suitable substituents include, for example, one or more $C_{1-6}$ alkyl, $C_{1-6}$ alkoxy, OH, COOH, COOMe, $NH_2$, $NMe_2$, NHMe, $NO_2$, CN, $CF_3$ and/or halo groups. Preferably, the cycloalkyl group is a $C_{3-6}$-cycloalkyl, even more preferably a $C_{3-4}$ cycloalkyl group. Examples include cyclopropyl, cyclobutyl, cyclopentyl, cyclohexyl and the like. In addition, the carbocyclic ring itself may optionally contain one or more heteroatoms, for example, to give a heterocycloalkyl group such as tetrahydrofuran, pyrrolidine, piperidine, piperazine or morpholine.

The term 'alkyoxy' refers to the group 'O-alkyl' or 'O-cycloalkyl', wherein alkyl and cycloalkyl are as defined above.

'Halogen' or 'halo' as applied herein encompasses F, Cl, Br, I.

The term 'haloalkyl' refers to an alkyl group as defined above substituted by one or more halogen atoms.

As used herein, the term 'aryl' refers to a stable 5 or 6-membered monocylic ring which is unsaturated. The aryl group may optionally include one or more heteroatoms selected from O, N and S. In addition, the aryl group may be optionally substituted, for example, by one or more $C_{1-6}$ alkyl, $C_{1-6}$ alkoxy, OH, COOH, COOMe, $NH_2$, $NMe_2$, NHMe, $NO_2$, CN, $CF_3$ and/or halo groups. More preferably, the aryl group may be optionally substituted by one or more Me, OMe, OEt, OiPr, $NO_2$, Cl or F groups.

The term 'aralkyl' as applied herein includes an alkyl group as defined above in combination with an aryl group. The aryl group may be an aromatic ring, for example, a stable 5 or 6-membered monocylic or a stable 9 or 10-membered bicyclic ring which is unsaturated. The aryl group may optionally comprise one or more heteroatoms selected from O, N and S. In addition, the aryl group may be optionally substituted, for example, by one or more $C_{1-6}$ alkyl, $C_{1-6}$ alkoxy, OH, COOH, COOMe, $NH_2$, $NMe_2$, NHMe, $NO_2$, CN, $CF_3$ and/or halo groups. Preferably, the aralkyl group is a $C_{1-8}$-alkyl-$C_{5-10}$-aryl group, even more preferably a $C_{1-8}$-alkyl-phenyl group. More preferably still, the alkyl-aryl group is selected from $CH_2Ph$ and $CH_2OCH_2Ph$.

The present invention includes all salts, hydrates, solvates, complexes and prodrugs of the compounds of this invention. The term "compound" is intended to include all such salts, hydrates, solvates, complexes and prodrugs, unless the context requires otherwise.

In particular, the skilled person will appreciate that the ketone group of the bicycle core of compounds of formula (I) may exist in alternative forms such as the hydrate (as shown below), and the invention extends to all such alternative forms.

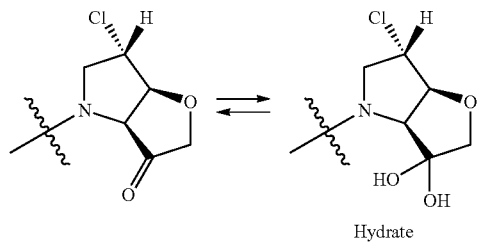

Hydrate

Abbreviations and symbols commonly used in the peptide and chemical arts are used herein to describe compounds of the present invention, following the general guidelines presented by the IUPAC-IUB Joint Commission on Biochemical Nomenclature as described in *Eur. J. Biochem.*, 158, 9-, 1984. Compounds of formula (I) and the intermediates and starting materials used in their preparation are named in accordance with the IUPAC rules of nomenclature in which the characteristic groups have decreasing priority for citation as the principle group.

In one preferred embodiment of the invention:

$R^3$ is selected from cyclopentyl or cyclohexyl;

$R^9$ is selected from the following:

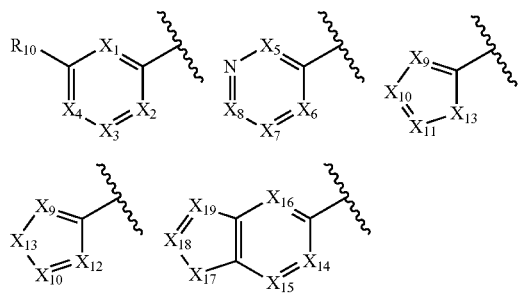

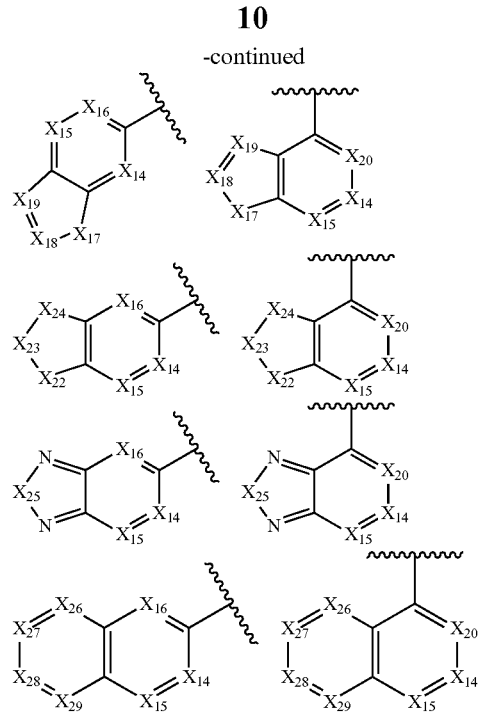

wherein:

$X_1, X_2, X_3, X_4, X_{14}, X_{15}, X_{16}$ and $X_{20}$ are each independently selected from:
  CH, C—($C_{1-6}$-alkyl), C—($C_{1-6}$-alkoxy), C-halo and N;
  such that a maximum of two of $X_1, X_2, X_3, X_4, X_{14}, X_{15}, X_{16}$ and $X_{20}$ are selected from N, C-halo and C—($C_{1-6}$-alkoxy);

$X_5, X_6, X_7$ and $X_8$ are each independently selected from:
  CH, C—($C_{1-6}$-alkyl), C—($C_{1-6}$-alkoxy), C-halo, N and C—OH;
  such that a maximum of one of $X_5, X_6, X_7$ and $X_8$ is N, C-halo, C—OH or C—($C_{1-6}$-alkoxy);

$X_9$ and $X_{12}$ are each independently selected from:
  CH, C—($C_{1-6}$-alkyl), C—($C_{1-6}$-alkoxy), C-halo and N;

$X_{10}$ and $X_{11}$ are each independently selected from:
  CH, C—($C_{1-6}$-alkyl), C—($C_{1-6}$-alkoxy), C-halo, N and $R_{10}$;

$X_{19}$ is selected from:
  CH, C—($C_{1-6}$-alkyl), C—($C_{1-6}$-alkoxy), C—C(O)$NH_2$, C—C(O)NH($C_{1-6}$-alkyl), C—C(O)N($C_{1-6}$-alkyl)$_2$, C-halo and N;

$X_{18}$ is selected from:
  CH, C—($C_{1-6}$-alkyl), C—($C_{1-6}$-alkoxy), C—$NH_2$, C—N($C_{1-6}$-alkyl)$_2$, C—NH($C_{1-6}$-alkyl), C—NHC(O)$C_{1-6}$-alkyl, C-halo and N;
  or when $X_{19}$ is CH, C—($C_{1-6}$-alkyl), or C-halo then $X_{18}$ may additionally be selected from C—C(O)$NH_2$ and C—C(O)N($C_{1-6}$-alkyl)$_2$;

$X_{13}$ and $X_{17}$ are each independently selected from:
  O, S, NH and N—($C_{1-6}$-alkyl);

$X_{22}$ and $X_{24}$ are each independently selected from:
  $CH_2$, CH—($C_{1-6}$-alkyl), O, S, NH and )C=O;

$X_{23}$ is selected from:
  $CH_2$, CH—($C_{1-6}$-alkyl), C—($C_{1-6}$-alkyl)$_2$ and NH;
  or when either $X_{22}$ or $X_{24}$ are other than )C=O then $X_{23}$ may additionally be )C=O;

$X_{25}$ is selected from:
  O, S, NH and N($C_{1-6}$-alkyl);

$X_{26}, X_{27}, X_{28}$ and $X_{29}$ are each independently selected from:
  CH, C—($C_{1-6}$-alkyl), C—($C_{1-6}$-alkoxy), C-halo and N;

such that a maximum of two of $X_{26}$, $X_{27}$, $X_{28}$ and $X_{29}$ are selected from C—($C_{1-6}$-alkoxy), C-halo and N;
$R_{10}$ is selected from:

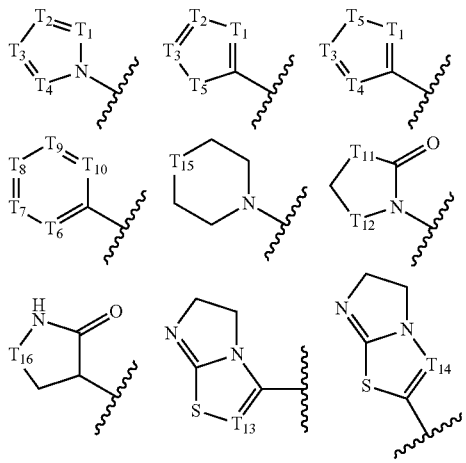

wherein:
$T_1$, $T_2$, $T_3$ and $T_4$ are each independently selected from:
CH, C—($C_{1-6}$-alkyl), C—($C_{1-6}$-alkoxy), C—$NH_2$, C—NH($C_{1-6}$-alkyl), C—N($C_{1-6}$-alkyl)$_2$, C-halo and N;
such that a maximum of one of $T_1$, $T_2$, $T_3$ and $T_4$ is C—($C_{1-6}$-alkoxy), C—$NH_2$, C—NH($C_{1-6}$-alkyl), C—N($C_{1-6}$-alkyl)$_2$ or C-halo;
$T_5$ is selected from:
O, S, NH and N($C_{1-6}$-alkyl);
$T_6$, $T_7$, $T_8$, $T_9$ and $T_{10}$ are each independently selected from:
CH, C—($C_{1-6}$-alkyl), C—($C_{1-6}$-alkoxy), C—$NH_2$, C—NH($C_{1-6}$-alkyl), C—N($C_{1-6}$-alkyl)$_2$, C-halo and N;
such that a maximum of two of $T_6$, $T_7$, $T_8$, $T_9$ and $T_{10}$ are selected from C—($C_{1-6}$-alkoxy), C—$NH_2$, C—NH($C_{1-6}$-alkyl), C—N($C_{1-6}$-alkyl)$_2$, C-halo and N;
$T_{11}$ is selected from:
$CH_2$, NH and N($C_{1-6}$-alkyl);
$T_{12}$ is selected from:
$CH_2$, NH, N($C_{1-6}$-alkyl) and $\rangle$C=O;
$T_{13}$ and $T_{14}$ are each independently selected from:
CH, C—($C_{1-6}$-alkyl) and C-halo;
$T_{15}$ is selected from:
O, NH and N($C_{1-6}$-alkyl);
$T_{16}$ is selected from:
$CH_2$ and $\rangle$C=O;
or $R_{10}$ is selected from:
H, $C_{1-6}$-alkyl, OH, $C_{1-6}$-alkoxy, $NO_2$, halo, CN, C(O)$NH_2$, C(O)NH($C_{1-6}$-alkyl), C(O)N($C_{1-6}$-alkyl)$_2$, and $(CH_2)_n$—$NR^{11}R^{12}$;
wherein n is 0 or 1
and $R^{11}$ is selected from H, $C_{1-6}$-alkyl, acetyl, C(O)$NH_2$, C(O)N($C_{1-6}$-alkyl)$_2$:
and $R^{12}$ is selected from H and $C_{1-6}$-alkyl.

In one preferred embodiment of the invention:
$R^3$ is selected from cyclopentyl or cyclohexyl;
$X_1$, $X_2$, $X_3$, $X_4$, $X_{14}$, $X_{15}$, $X_{16}$ and $X_{20}$ are independently selected from:
CH, CMe, C—OMe, C—F, C—Cl and N:
such that a maximum of two of $X_1$, $X_2$, $X_3$, $X_4$, $X_{14}$, $X_{15}$, $X_{16}$ and $X_{20}$ are chosen as N or C—Cl or C—OMe;

$X_5$, $X_6$, $X_7$ and $X_8$ are independently selected from:
CH, CMe, C—OMe, C—F, C—Cl, N and OH;
such that a maximum of one of $X_5$, $X_6$, $X_7$ and $X_8$ is chosen as N or C—Cl or C—OH or C—OMe;
$X_9$ and $X_{12}$ are independently selected from:
CH, CMe, C—OMe, C—F, C—Cl and N;
$X_{10}$ and $X_{11}$ are independently selected from:
CH, CMe, C—OMe, C—F, C—Cl, N and $R_{10}$;
$X_{19}$ is selected from:
CH, CMe, C—OMe, C—C(O)$NH_2$, C—C(O)$NMe_2$, C—F, C—Cl and N;
$X_{18}$ is selected from:
CH, CMe, C—OMe, C—$NH_2$, C—$NMe_2$, C—NHMe, C—NHC(O)Me, C—F, C—Cl and N;
or when $X_{19}$ is CH, CMe or C—F then $X_{18}$ may additionally be selected from C—C(O)$NH_2$ and C—C(O)$NMe_2$;
$X_{13}$ and $X_{17}$ are independently selected from:
O, S, NH and NMe.
$X_{22}$ and $X_{24}$ are independently selected from:
$CH_2$, CHMe, O, S, NH, NMe and $\rangle$C=O;
$X_{23}$ is selected from:
$CH_2$, CHMe, $CMe_2$, NH and NMe;
or when either $X_{22}$ or $X_{24}$ are other than $\rangle$C=O then $X_{23}$ may additionally be $\rangle$C=O or $\rangle$S(O)$_2$;
$X_{25}$ is selected from:
O, S, NH and NMe;
$X_{26}$, $X_{27}$, $X_{28}$ and $X_{29}$ are independently selected from:
CH, CMe, C—OMe, C—F, C—Cl, C—Br and N;
such that a maximum of two of $X_{26}$, $X_{27}$, $X_{28}$ and $X_{29}$ are chosen as C—OMe, C—Cl, C—Br and N;
$X_{30}$ is selected from:
$CH_2$, $CH_2CH_2$, NH, NMe, O, S and $\rangle$C=O;
$X_{31}$ is selected from:
$CH_2$, NH and NMe;
or when $X_{30}$ is other than $\rangle$C=O, O or S then $X_{31}$ may additionally be $\rangle$C=O or O;
$X_{32}$ is selected from:
$CH_2$, NH, NMe and $\rangle$C=O;
$X_{33}$ is selected from:
$CH_2$, NH and NMe;
or when $X_{32}$ is other than $\rangle$C=O then $X_{33}$ may additionally be $\rangle$C=O or O;
$X_{34}$ is selected from:
NH and NMe;
$T_1$, $T_2$, $T_3$ and $T_4$ are independently selected from:
CH, CMe, C—OMe, C—$NH_2$, C—NHMe, C—$NMe_2$, C—F, C—Cl and N:
such that a maximum of one of $T_1$, $T_2$, $T_3$ and $T_4$ is chosen as C—OMe, C—$NH_2$, C—NHMe, C—$NMe_2$, C—F and C—Cl;
$T_5$ is selected from:
O, S, NH and NMe.
$T_6$, $T_7$, $T_8$, $T_9$ and $T_{10}$ are independently selected from:
CH, CMe, C—OMe, C—$NH_2$, C—NHMe, C—$NMe_2$, C—F, C—Cl and N:
such that a maximum of two of $T_6$, $T_7$, $T_8$, $T_9$ and $T_{10}$ are chosen as C—OMe, C—$NH_2$, C—NHMe, C—$NMe_2$, C—F, C—Cl and N;
$T_{11}$ is selected from:
$CH_2$, NH and NMe;
$T_{12}$ is selected from:
$CH_2$, NH, NMe and $\rangle$C=O;
$T_{13}$ and $T_{14}$ are independently selected from:
CH, C—F and C—Cl;
$T_{15}$ is selected from:
O, NH and NMe;

$T_{16}$ is selected from:

CH$_2$ and )C=O;

or $R_{10}$ is selected from:

H, Me, OH, OMe, OEt, OiPr, NO$_2$, F, Cl, Br, CN, C(O)NH$_2$, C(O)NHMe, C(O)NMe$_2$, and (CH$_2$)$_n$—NR$^{11}$R$^{12}$:

wherein n=0 or 1 and $R^{11}$ is selected from H, Me, acetyl, C(O)NH$_2$, C(O)NMe$_2$:

and $R^{12}$ is selected from H and Me;

$R_{13}$ is selected from:

C(O)NH$_2$, C(O)NHMe, C(O)N(Me)$_2$, C(O)NH(cyclopropyl), S(O)$_2$NH$_2$, S(O)$_2$(Me), S(O)$_2$NH(Me), S(O)$_2$N(Me)$_2$, S(O)$_2$NH(cyclopropyl) and (CH$_2$)$_n$—NR$^{14}$R$^{15}$;

wherein n is 0 or 1;

and $R^{14}$ is selected from H, Me, C(O)Me, C(O)Et, C(O)(cyclopropyl), C(O)Ph, C(O)NH$_2$, C(O)NH(Me), C(O)N(Me)$_2$, C(O)NH(cyclopropyl), C(O)O(Me), C(O)O(cyclopropyl), C(O)OPh, S(O)$_2$(Me), S(O)$_2$(cyclopropyl), S(O)$_2$NH$_2$, S(O)$_2$NH(Me), S(O)$_2$N(Me)$_2$, S(O)$_2$NH(cyclopropyl) and S(O)$_2$Ph;

and $R^{15}$ is selected from H and Me.

In one preferred embodiment, $R^3$ is cyclopentyl.

In another preferred embodiment, $R^3$ is cyclohexyl.

In one preferred embodiment, the compound of the invention is of formula Ia such that the central amino acid moiety is derived from (S)-2-amino-2-cyclohexylacetic acid (CAS 14328-51-9).

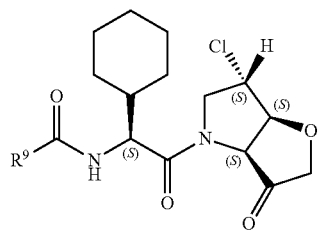

(Ia)

wherein $R^9$ is as defined above.

In another preferred embodiment, the compound of the invention is of formula Ib such that the central amino acid moiety is derived from (S)-2-amino-2-cyclopentylacetic acid (CAS 2521-84-8).

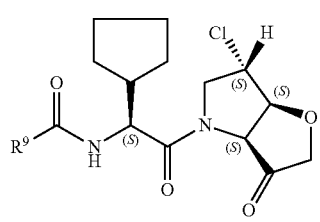

(Ib)

wherein $R^9$ is as defined above.

In one preferred embodiment, $R^9$ is selected from:

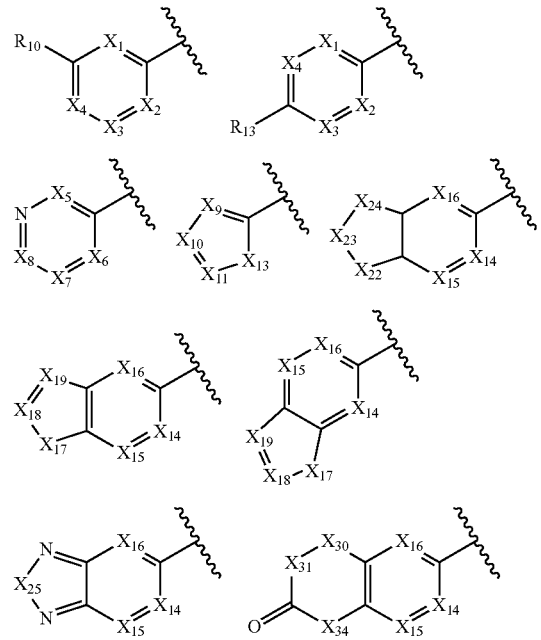

wherein $X_1$, $X_2$, $X_3$, $X_4$, $X_5$, $X_6$, $X_7$, $X_8$, $X_9$, $X_{10}$, $X_{11}$, $X_{13}$, $X_{14}$, $X_{15}$, $X_{16}$, $X_{17}$, $X_{18}$, $X_{19}$, $X_{22}$, $X_{23}$, $X_{24}$, $X_{25}$, $X_{30}$, $X_{31}$, $X_{34}$, $R_{10}$ and $R_{13}$ are as defined above.

In one preferred embodiment $R^9$ is selected from:

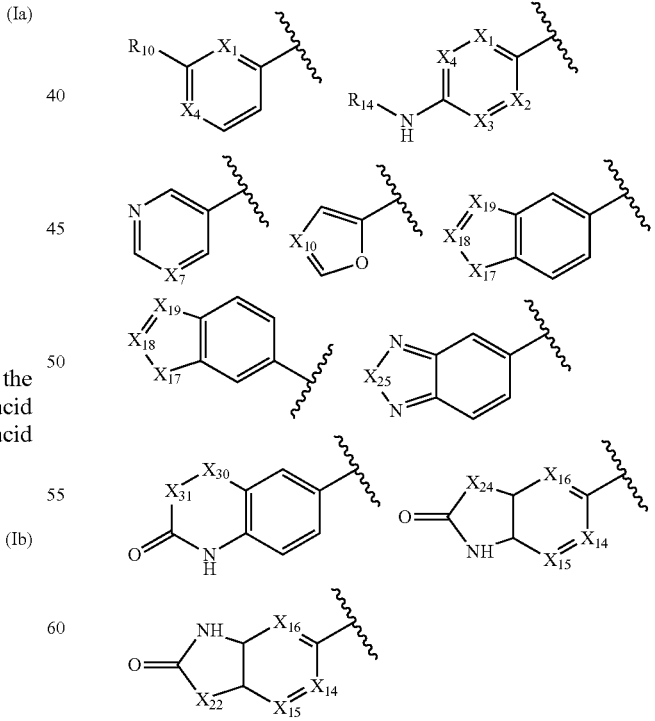

wherein $X_1$, $X_2$, $X_3$, $X_4$, $X_7$, $X_{10}$, $X_{17}$, $X_{18}$, $X_{19}$, $X_{22}$, $X_{24}$, $X_{25}$, $X_{30}$, $X_{31}$, $R_{10}$ and $R_{14}$ are as defined above.

In one preferred embodiment, $R_{10}$ is selected from:

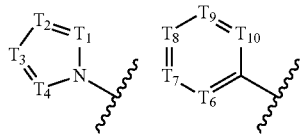

wherein $T_1$, $T_2$, $T_3$, $T_4$, $T_6$, $T_7$, $T_8$, $T_9$ and $T_{10}$ are as defined above.

In an even more preferred embodiment, $R_{10}$ is:

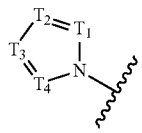

wherein one, two or three of $T_1$, $T_2$, $T_3$ and $T_4$ are N and the remainder are CH or CMe.

In another preferred embodiment, $R_{10}$ is selected from:

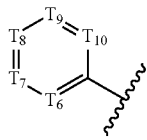

wherein one of $T_6$, $T_7$, $T_8$, $T_9$ and $T_{10}$ is N and the remainder are CH or C—F.

In one preferred embodiment $R^9$ is selected from:

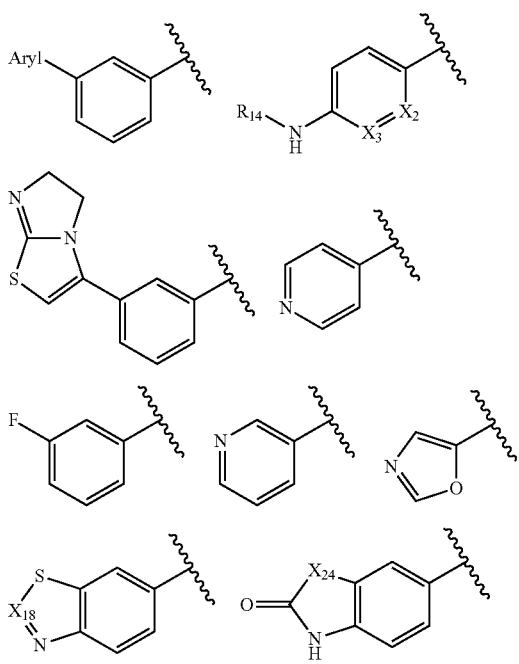

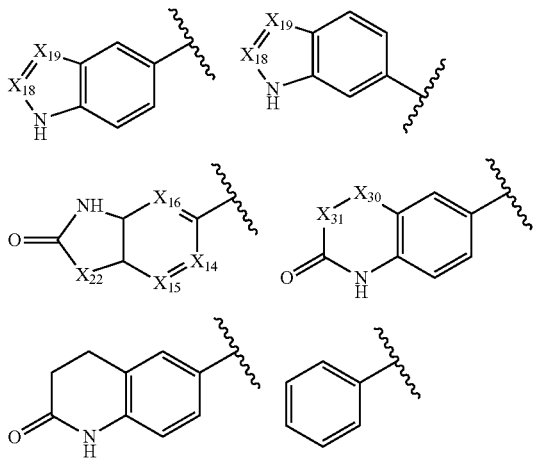

wherein aryl, $X_2$, $X_3$, $X_{18}$, $X_{19}$, $X_{22}$, $X_{24}$, $X_{30}$ and $X_{31}$ are as defined above and;

$R^{14}$ is selected from C(O)Me, C(O)Et, C(O)(cyclopropyl), C(O)NH$_2$, C(O)NH(Me), C(O)N(Me)$_2$, C(O)NH(cyclopropyl), C(O)O(Me), C(O)O(cyclopropyl), S(O)$_2$(Me), S(O)$_2$(cyclopropyl), S(O)$_2$NH$_2$, S(O)$_2$NH(Me), S(O)$_2$N(Me)$_2$, S(O)$_2$NH(cyclopropyl) and S(O)$_2$Ph.

In one highly preferred embodiment, $R^9$ is selected from:

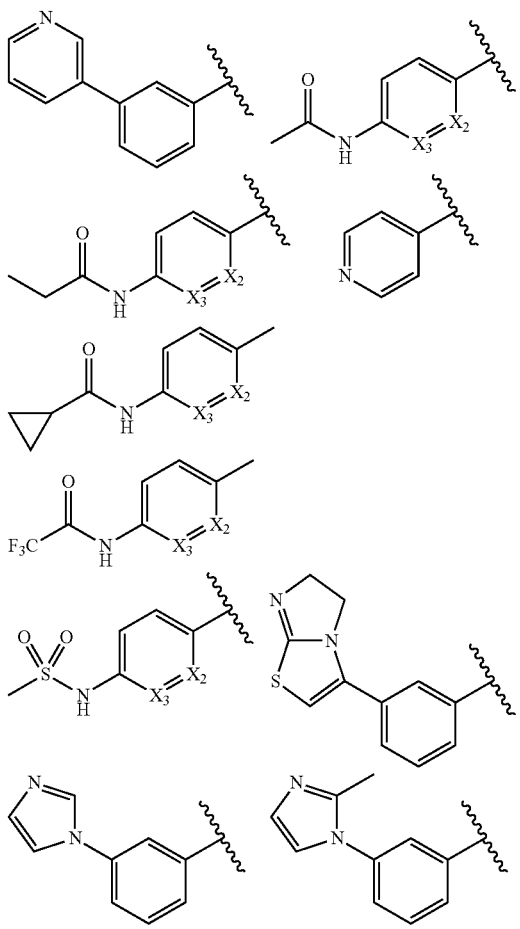

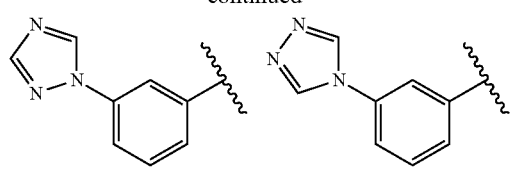
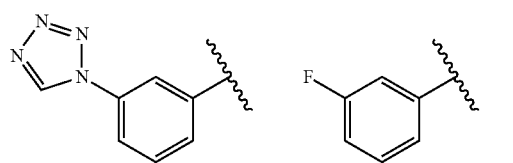
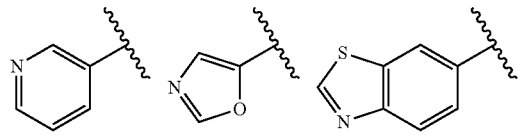
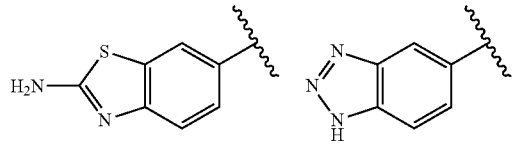
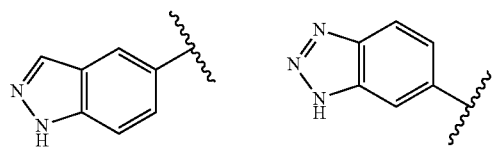
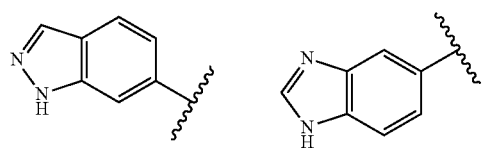
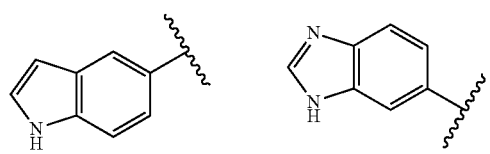
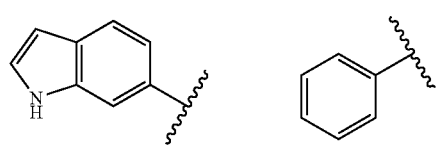
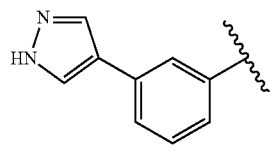
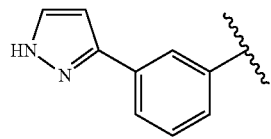
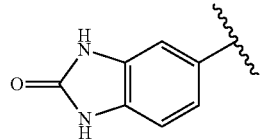
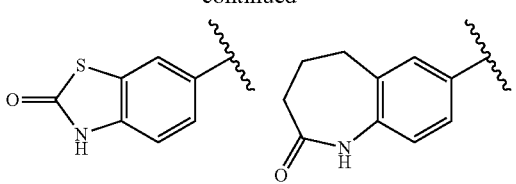
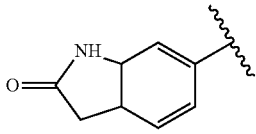
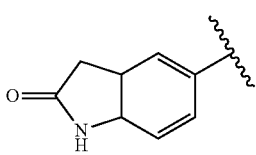
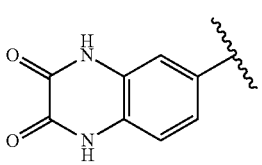
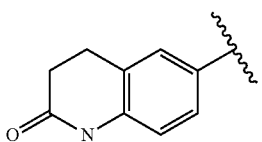
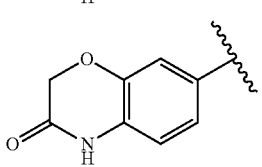
In one particularly preferred embodiment, $R^9$ is selected from:
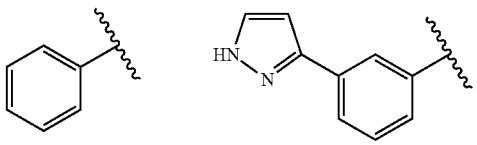
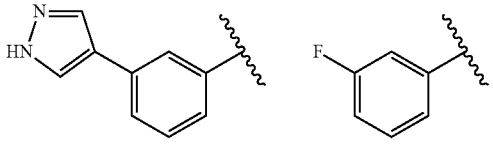
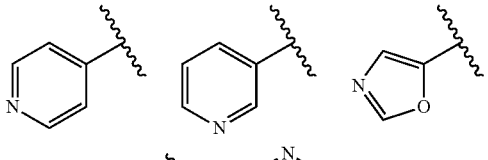
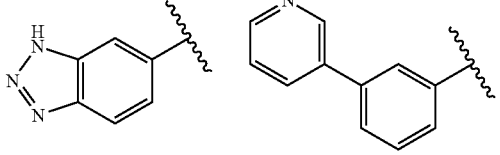

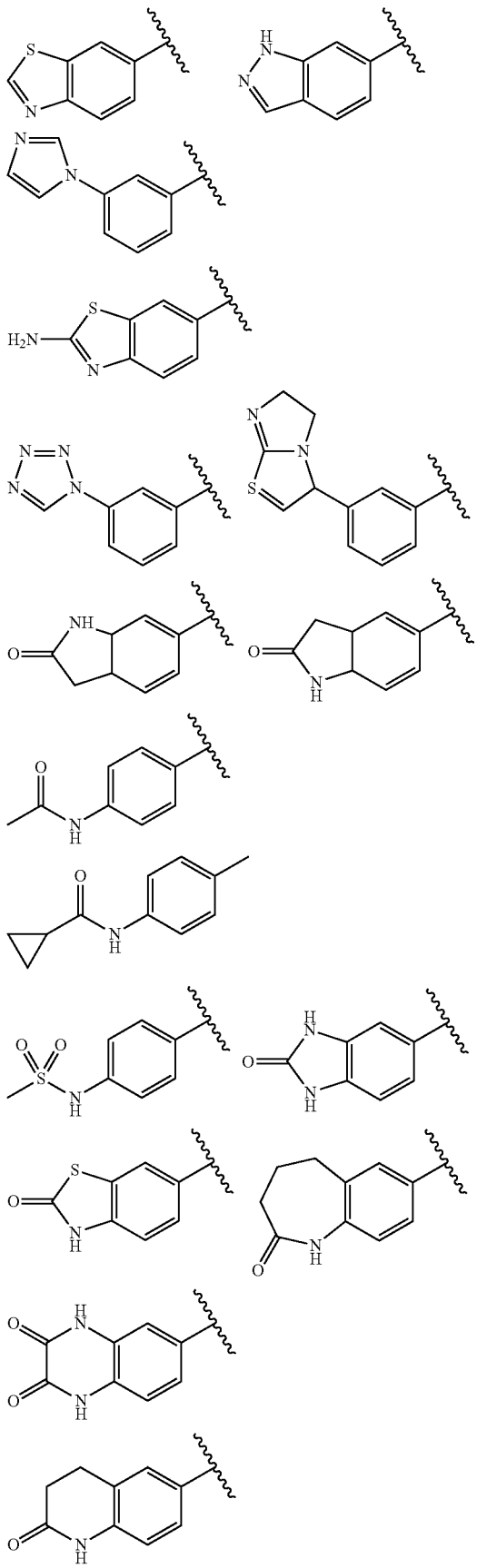
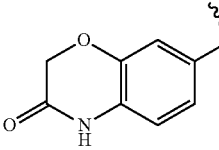

In one highly preferred embodiment, the compound of the invention is selected from the following:

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)nicotinamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-tetrazol-1-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)isonicotinamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-fluorobenzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-imidazol-1-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(2-methyl-1H-imidazol-1-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(pyridin-3-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(5,6-dihydroimidazo[2,1-b]thiazol-3-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indole-5-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-pyrazol-4-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-pyrazol-3-yl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-benzo[d][1,2,3]triazole-6-carboxamide 2-Amino-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indazole-6-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)oxazole-5-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2,3-dioxo-1,2,3,4-tetrahydro quinoxaline-6-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-1,2,3,4-tetrahydroquinoline-6-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-5-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-6-carboxamide 4-Acetamido-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(cyclopropanecarboxamido)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(methylsulfonamido)benzamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydro-1H-benzo[d]imidazole-5-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydrobenzo[d]thiazole-6-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3,4,5-tetrahydro-1H-benzo[b]azepine-7-carboxamide N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-oxo-3,4-dihydro-2H-benzo[b][1,4]oxazine-7-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)nicotinamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-tetrazol-1-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)isonicotinamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-fluorobenzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-imidazol-1-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(2-methyl-1H-imidazol-1-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(pyridin-3-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzo[d]thiazole-6-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(5,6-dihydroimidazo[2,1-b]thiazol-3-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-indole-5-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-pyrazol-4-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-pyrazol-3-yl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-benzo[d][1,2,3]triazole-6-carboxamide 2-Amino-N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzo[d]thiazole-6-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-indazole-6-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)oxazole-5-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-1,2,3,4-tetrahydroquinoline-6-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-5-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-6-carboxamide 4-Acetamido-N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(cyclopropanecarboxamido)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(methylsulfonamido)benzamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydro-1H-benzo[d]imidazole-5-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydrobenzo[d]thiazole-6-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3,4,5-tetrahydro-1H-benzo[b]azepine-7-carboxamide N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-oxo-3,4-dihydro-2H-benzo[b][1,4]oxazine-7-carboxamide In one particularly preferred embodiment, the compound of the invention is selected from Examples 1-39 described hereinbelow.

Even more preferably, the compound of the invention is selected from Examples 2, 3, 4, 5, 6, 9, 10, 12, 14, 15, 16, 17 and 18-39 described hereinbelow.

Pharmaceutical Compositions

A further aspect of the invention relates to a pharmaceutical composition comprising a compound of the invention admixed with one or more pharmaceutically acceptable diluents, excipients or carriers. Other active materials may also be present, as may be considered appropriate or advisable for the disease or condition being treated or prevented.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller. The carrier, or, if more than one be present, each of the carriers, must be acceptable in the sense of being compatible with the other ingredients of the formulation and not deleterious to the recipient.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with amino acids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkane alcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers-e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

A prodrug may for example constitute a ketal or hemiketal derivative of the exocyclic ketone functionality present in the 6-(S)-chlorotetrahydrofuro[3,2-b]pyrrol-3-one scaffold.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Assays

Another aspect of the invention relates to the use of a compound of the invention as defined hereinabove in an assay for identifying further candidate compounds that influence the activity of a cysteine proteinase.

Preferably, the assay is capable of identifying candidate compounds that are capable of inhibiting one or more CAC1 cysteine proteinases.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays. Preferably, the competitive binding assay comprises contacting a compound of the invention with a cysteine proteinase in the presence of a known substrate of said enzyme and detecting any change in the interaction between said cysteine proteinase and said known substrate.

A further aspect of the invention provides a method of detecting the binding of a ligand to a cysteine proteinase, said method comprising the steps of:
(i) contacting a ligand with cysteine proteinase in the presence of a known substrate of said enzyme;
(ii) detecting any change in the interaction between said enzyme and said known substrate;
and wherein said ligand is a compound of the invention.

One aspect of the invention relates to a process comprising the steps of:
(a) performing an assay method described hereinabove;
(b) identifying one or more ligands capable of binding to a ligand binding domain; and
(c) preparing a quantity of said one or more ligands.

Another aspect of the invention provides a process comprising the steps of:
(a) performing an assay method described hereinabove;
(b) identifying one or more ligands capable of binding to a ligand binding domain; and (c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders selected from rheumatoid arthritis, osteoarthritis, chronic obstructive pulmonary disease (COPD), atherosclerosis, cardiovascular diseases which exhibit significant damage and remodeling of extracellular matrix (ECM) and chronic pain.

The above methods may be used to screen for a ligand useful as an inhibitor of one or more cysteine proteinases.

Compounds of general formula (I) are useful both as laboratory tools and as therapeutic agents. In the laboratory certain compounds of the invention are useful in establishing whether a known or newly discovered cysteine proteinase contributes a critical or at least significant biochemical function during the establishment or progression of a disease state, a process commonly referred to as 'target validation'.

According to a further aspect of the invention, there is provided a method of validating a known or putative cysteine proteinase as a therapeutic target, the method comprising:
(a) assessing the in vitro binding of a compound as described above to an isolated known or putative cysteine proteinase, providing a measure of potency; and optionally, one or more of the steps of:
(b) assessing the binding of the compound to closely related homologous proteinases of the target and general housekeeping proteinases (e.g. trypsin) to provide a measure of selectivity;
(c) monitoring a cell-based functional marker of a particular cysteine proteinase activity, in the presence of the compound; and
(d) monitoring an animal model-based functional marker of a particular cysteine proteinase activity in the presence of the compound.

The invention therefore provides a method of validating a known or putative cysteine proteinase as a therapeutic target. Differing approaches and levels of complexity are appropriate to the effective inhibition and 'validation' of a particular target. In the first instance, the method comprises assessing the in vitro binding of a compound of general formula (I) to an isolated known or putative cysteine proteinase, providing a measure of 'potency'. An additional assessment of the binding of a compound of general formula (I) to closely related homologous proteinases of the target and general housekeeping proteinases (e.g. trypsin) provides a measure of 'selectivity'. A second level of complexity may be assessed by monitoring a cell-based functional marker of a particular cysteine proteinase activity, in the presence of a compound of general formula (I). For example, an 'osteoclast resorption assay' has been utilised as a cell-based secondary in vitro testing system for monitoring the activity of cathepsin K and the biochemical effect of proteinase inhibitors (e.g. see WO-A-9850533). An 'MHC—II processing—T-cell activation assay' has been utilised as a cell-based secondary in vitro testing system for monitoring the activity of cathepsin S and the biochemical effect of proteinase inhibitors (Shi, G-P., et al, *Immunity*, 10, 197-206, 1999). When investigating viral or bacterial infections such a marker could simply be a functional assessment of viral (e.g. count of mRNA copies) or bacterial loading and assessing the biochemical effect of proteinase inhibitors. A third level of complexity may be assessed by monitoring an animal model-based functional marker of a particular cysteine proteinase activity, in the presence of a compound of general formula (I). For example, murine models of *Leishmania* infection, *P. vinckei* infection, malaria (inhibition of falcipain) and *T. cruzi* infection (cruzipain), indicate that inhibition of cysteine proteinases that play a key role in pathogen propagation is effective in arresting disease symptoms, 'validating' said targets.

The invention therefore extends to the use of a compound of general formula (I) in the validation of a known or putative cysteine proteinase as a therapeutic target.

Biological Activity

The compounds of the present invention are structurally distinct from the prior art (e.g. WO-A-02057270; Quibell, M. et. al., Bioorg. Med. Chem. 13, 609-625, 2005; Quibell M, et al Bioorg. Med. Chem., 12, 5689-5710, 2004; WO-A-05066180) in that a 6-(S)-chloro substituent and a cyclohexylglycyl or cyclopentylglycyl moiety form an integral part. This combination of features provides compounds with surprisingly high dual efficacies for human cathepsin S and cathepsin K which are important properties required for development of an efficacious dual therapeutic. If either of these intrinsic moieties is removed from compounds of formula I, then a surprisingly large loss in potency and/or a significant loss in selectivity is observed. Indeed, all of the compounds of the present invention prepared to date exhibit dual potent in vitro inhibition for human cathepsin S and cathepsin K with Ki<50 nM. In contrast, the majority of the eighty-two prior art compounds detailed in WO-A-02057270 are either inhibitors of cathepsin S or cathepsin K and in the majority of examples, greater than 100-fold less potent against either proteinase.

The closest prior art, compound (38) (see WO-A-02057270, pg 151), exhibits a 65-fold improvement in in vitro potency against human cathepsin S and a greater than 114-fold improvement in in vitro potency against human cathepsin K upon addition of a 6-(S)-chloro substituent and substitution of the (S)-cyclohexylalanyl moiety with (S)-cyclohexylglycyl (EXAMPLE 1). The surprising synergistic relationship between these two intrinsic changes is clearly seen when comparing prior art compound (38) with novel compounds (1-2) and EXAMPLE 1. Prior art compound (38) exhibits a 2.5-fold improvement in in vitro potency against human cathepsin S and a greater than 13-fold improvement in in vitro potency against human cathepsin K upon substitution of the (S)-cyclohexylalanyl moiety with (S)-cyclohexylglycyl (Compound 1), providing a dual inhibitor that has only moderate potency versus cathepsins S and K. Further addition of a 6-(S)-fluoro substituent to Compound 1 provides a 3.8-fold improvement in in vitro potency against human cathepsin S and a 3.2-fold improvement in in vitro potency against human cathepsin K (Compound 2), again providing a dual inhibitor that has only moderate potency versus cathepsins S and K. Alternatively, addition of a 6-(S)-chloro substituent to Compound 1 provides a 27-fold improvement in in vitro potency against human cathepsin S and a 8.7-fold improvement in in vitro potency against human cathepsin K (EXAMPLE 1) providing a dual inhibitor that has high potency versus cathepsins S and K.

By way of further comparison, consider novel compounds (3-4) and EXAMPLE 2. Addition of a 6-(S)-fluoro substituent to compound 3 provides a 3.4-fold improvement in in vitro potency against human cathepsin S and a 1.7-fold improvement in in vitro potency against human cathepsin K (Compound 4), providing a dual inhibitor that has only moderate potency versus cathepsins S and K. Alternatively, addition of a 6-(S)-chloro substituent to Compound 3 provides a 47-fold improvement in in vitro potency against human cathepsin S and a 20.5-fold improvement in in vitro potency against human cathepsin K (EXAMPLE 2), providing a dual inhibitor that has high potency versus cathepsins S and K.

As a further comparison, consider novel compound (5) with EXAMPLES 3 and 4. The 6-(R)-chloro analogue (compound 5) has an in vitro Ki of 32 nM versus cathespin S and 230 nM versus cathespin K. The stereochemical importance of the 6-(S)-chloro substituent in clearly seen when comparing compound (5) with EXAMPLE 3 that has an in vitro Ki of 1.7 nM versus cathespin S and 23 nM versus cathespin K. Considering EXAMPLE 3, substitution of the (S)-cyclohexylglycyl moiety for the (S)-cyclopentylglycyl moiety provides EXAMPLE 4 that has an in vitro Ki of 14.6 nM versus cathespin S and 10.4 nM versus cathespin K. Both EXAMPLE 3 and 4 are highly potent dual inhibitors of cathepsins S and K.

Preferably, the compounds exhibit dual in vitro inhibition versus human cathepsin S and cathepsin K with Ki<50 nM, more preferably <25 nM and even more preferably <10 nM.

Therapeutic Use

Compounds of general formula (I) are useful for the in vivo treatment or prevention of diseases in which participation of a cysteine proteinase is implicated.

Preferably, the compound of general formula I is a dual inhibitor of cathepsin S and cathepsin K. As used herein, the term "dual for cathepsin S and K" means that the inhibitor is a potent inhibitor of oth cathepsin S and cathepsin K. Preferably, the inhibitor exhibits a selectivity ratio for cathepsin S and cathepsin K over other mammalian CAC1 cysteinyl proteinases of greater than 2-fold, more preferably greater than 5-fold, more preferably greater than 10-fold, even more preferably greater than 25-fold, more preferably still, greater than 50-fold or 100-fold.

According to a further aspect of the invention, there is provided a compound of general formula (I) for use in medicine, especially for preventing or treating diseases in which the disease pathology may be modified by inhibiting a cysteine proteinase.

According to a further aspect of the invention, there is provided the use of a compound of general formula (I) in the preparation of a medicament for preventing or treating diseases in which the disease pathology may be modified by inhibiting a cysteine proteinase.

Certain cysteine proteinases function in the normal physiological process of protein degradation in animals, including humans, e.g. in the degradation of connective tissue. However, elevated levels of these enzymes in the body can result in pathological conditions leading to disease. Thus, cysteine proteinases have been implicated in various disease states, including but not limited to, infections by *Pneumocystis carinii, Trypsanoma cruzi, Trypsanoma brucei brucei* and *Crithidia fusiculata*; as well as in osteoporosis, osteoarthritis, rheumatoid arthritis, multiple sclerosis, chronic pain, autoimmunity, schistosomiasis, malaria, tumour metastasis, metachromatic leukodystrophy, muscular dystrophy, amytrophy, and the like (see WO-A-9404172 and EP-A-0603873 and references cited therein). Additionally, a secreted bacterial cysteine proteinase from *S. Aureus* called staphylopain has been implicated as a bacterial virulence factor (Potempa, J., et al. J. Biol. Chem., 262 (6), 2664-2667, 1998).

The invention is useful in the prevention and/or treatment of each of the disease states mentioned or implied above. The present invention also is useful in a method of treatment or prevention of diseases caused by pathological levels of cysteine proteinases, particularly cysteine proteinases of the papain superfamily, which methods comprise administering to an animal, particularly a mammal, most particularly a human, in need thereof a compound of the present invention. The present invention particularly provides methods for treating diseases in which cysteine proteinases are implicated, including infections by *Pneumocystis carinii, Trypsanoma cruzi, Trypsanoma brucei, Leishmania mexicana, Clostridium histolyticum, Staphylococcus aureus*, foot-and-mouth disease virus and *Crithidia fusiculata*; as well as in osteoarthritis, rheumatoid arthritis, multiple sclerosis, chronic pain, autoimmunity, schistosomiasis, malaria, tumour metastasis, metachromatic leukodystrophy, muscular dystrophy, amytrophy.

Dual inhibitors of cathepsin S and K are particularly useful for the treatment of rheumatoid arthritis, osteoarthritis, chronic obstructive pulmonary disease (COPD), atherosclerosis, cardiovascular diseases which exhibit significant damage and remodeling of extracellular matrix (ECM) and chronic pain. The compounds of the invention are particularly useful in the treatment of the above disorders.

Preferred features for each aspect of the invention are as for each other aspect *mutatis mutandis*.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica.

Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to inhibit the proteinase implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful.

Typically, the parenteral dose will be about 0.01 to about 100 mg/kg; preferably between 0.1 and 20 mg/kg, in a manner to maintain the concentration of drug in the plasma at a concentration effective to inhibit a cysteine proteinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect. Prodrugs of compounds of the present invention may be prepared by any suitable method. For those compounds in which the prodrug moiety is a ketone functionality, specifically ketals and/or hemiketals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

Synthesis

Synthesis of 5,5-Bicyclic Core

One aspect of the invention relates to a process of preparing a compound of formula (I) as defined above, said process comprising oxidation of a compound of formula (II).

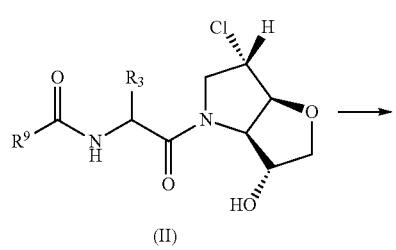

(II)

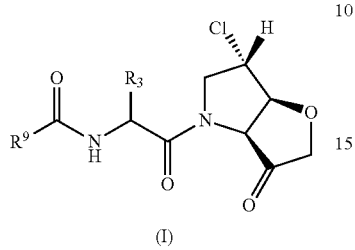

(I)

Any suitable oxidising agent may be used to convert the secondary alcohol group of (II) into the corresponding ketone (I). Suitable oxidising agents will be familiar to the skilled artisan. By way of example, the oxidation may be carried out via a Dess-Martin periodinane reaction [Dess, D. B. et al, J. Org. Chem. 1983, 48, 4155; Dess, D. B. et al, J. Am. Chem. Soc. 1991, 113, 7277], or via a Swern oxidation [Mancuso, A. J. et al, J. Org. Chem. 1978, 43, 2480]. Alternatively, the oxidation can be carried out using $SO_3$/pyridine/$Et_3N$/DMSO [Parith, J. R. et al, J. Am. Chem. Soc. 1967, 5505; U.S. Pat. No. 3,444,216, Parith, J. R. et al,], $P_2O_5$/DMSO or $P_2O_5$/$Ac_2O$ [Christensen, S. M. et al, Organic Process Research and Development, 2004, 8, 777]. Other alternative oxidation reagents include activated dimethyl sulphoxide [Mancuso, A. J., Swern, D. J., Synthesis, 1981, 165], pyridinium chlorochromate [Pianeatelli, G. et al, Sythesis, 1982, 245] and Jones' reagent [Vogel, A, I., Textbook of Organic Chemistry, 6$^{th}$ Edition].

More preferably, the process comprises treating a compound of formula (II) with Dess-Martin periodinane. Preferably, the reaction is carried out using dichloromethane as solvent.

In one preferred embodiment, the process of the invention comprises the step of converting a compound of formula (III) into a compound of formula (II) through standard amide bond formation between $R^9CONHCH(R^3)COOH$ and the compound of formula (III; $R^5$=H) with a suitable carboxylic acid activating agent.

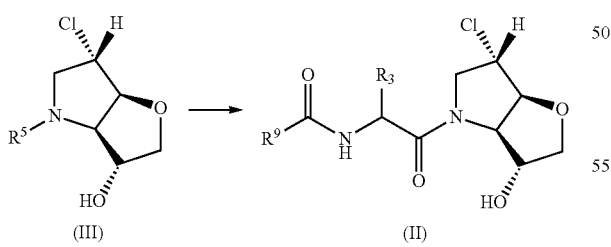

where $R^5$ is a protecting group or hydrogen.

In one preferred embodiment, protecting group $R^5$ is selected from benzyloxycarbonyl, tert-butoxycarbonyl, fluoren-9-ylmethoxycarbonyl, 1-(biphenyl-4-yl)-1-methylethoxycarbonyl, α,α-dimethyl-3,5-dimethoxylbenzyloxycarbonyl, p-methoxybenzyloxycarbonyl, p-nitrobenzyloxycarbonyl, allyloxycarbonyl and trichloroethoxycarbonyl.

More preferably, $R^5$ is benzyloxycarbonyl, tert-butoxycarbonyl (Boc) or flouren-9-ylmethoxycarbonyl (Fmoc).

In another preferred embodiment $R^5$ is H.

In a more preferred embodiment the process of the invention comprises the step of converting a compound of formula (IV) into a compound of formula (III; $R^5$=H)

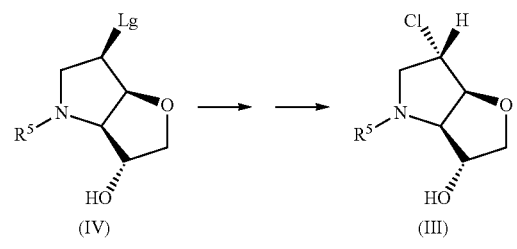

where Lg is a leaving group such as tosylate or mesylate and $R^5$ is as previously defined.

In an even more preferred embodiment the process of the invention comprises the step of converting a compound of formula (IVa; $R^5$=H) into a compound of formula (IIIa) or a compound of formula (IVb; $R^5$=Cbz) into a compound of formula (IIIb)

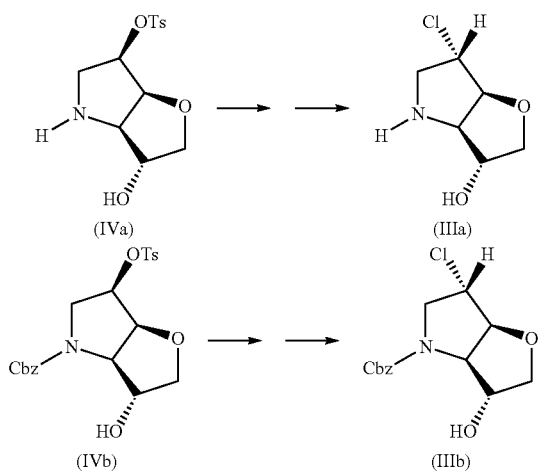

For compounds of formulae (IIIa) and (IIIb) the displacement of tosylate is typically performed using an excess of lithium chloride in DMF at 130° C. Displacement proceeds with inversion of configuration.

In one preferred embodiment the process of the invention comprises the step of converting a compound of formula (V) into a compound of formula (IV)

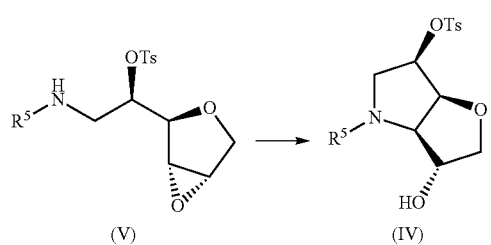

More preferably the intra-molecular cyclisation of compound (V) is induced by removal of the protecting group $R^5$.

Preferably, for this embodiment, $R^5$ is benzyloxycarbonyl (Cbz), and the process comprises hydrogenating a compound of formula (V) in the presence of a palladium catalyst.

In one preferred embodiment the process of the invention comprises the step of converting a compound of formula (VI) into a compound of formula (V)

(VI) → (V) (anti)

In one preferred embodiment, the oxidising agent is mCPBA.

In another preferred embodiment, the oxidising agent is a dioxirane.

The use of dioxiranes as oxidising agents is well documented in the literature [see (a) Hodgson, D. M. et al, Synlett, 310 (2002); (b) Adam, W. et al, Acc. Chem. Res. 22, 205, (1989); (c) Yang, D. et al, J. Org. Chem., 60, 3887, (1995); (d) Mello, R. et al, J. Org. Chem., 53, 3890, (1988); (e) Curci, R. et al, Pure & Appl. Chem., 67 (5), 811 (1995); (f) Emmons, W. D. et al, J. Amer. Chem. Soc. 89, (1955)].

Preferably, the dioxirane is generated in situ by the reaction of $KHSO_5$ with a ketone. However, the oxidation step can also be carried out using an isolated dioxirane, for example a stock solution of the dioxirane formed from acetone.

More preferably, the dioxirane is generated in situ using Oxone®, which is a commercially available oxidising agent containing $KHSO_5$ as the active ingredient.

Thus, in one preferred embodiment, the claimed process involves the in situ epoxidation of a compound of formula (VI) using Oxone® ($2KHSO_5 \cdot KHSO_4 \cdot K_2SO_4$) and a ketone co-reactant.

As mentioned above, the active ingredient of Oxone® is potassium peroxymonosulfate, $KHSO_5$ [CAS-RN 10058-23-8], commonly known as potassium monopersulfate, which is present as a component of a triple salt with the formula $2KHSO_5 \cdot KHSO_4 \cdot K_2SO_4$ [potassium hydrogen peroxymonosulfate sulfate (5:3:2:2), CAS-RN 70693-62-8; commercially available from DuPont]. The oxidation potential of Oxone® is derived from its peracid chemistry; it is the first neutralization salt of peroxymonosulfuric acid $H_2SO_5$ (also known as Caro's acid).

$$K^+{-}O{-}S(={O})_2({-}OOH)$$

Potassium Monopersulfate

Under slightly basic conditions (pH 7.5-8.0), persulfate reacts with the ketone co-reactant to form a three membered cyclic peroxide (a dioxirane) in which both oxygens are bonded to the carbonyl carbon of the ketone. The cyclic peroxide so formed then epoxidises the compound of formula VI by syn specific oxygen transfer to the alkene bond.

Preferably, the ketone is of formula (XIX)

(XIX)

wherein $R^a$ and $R^b$ are each independently alkyl, aryl, haloalkyl or haloaryl.

Where $R^a$ and/or $R^b$ are alkyl, the alkyl group may be a straight chain or branched alkyl group. Preferably, the alkyl group is a $C_{1-20}$ alkyl group, more preferably a $C_{1-15}$, more preferably still a $C_{1-12}$ alkyl group, more preferably still, a $C_{1-8}$ or $C_{1-6}$ alkyl group, more preferably a $C_{1-4}$ alkyl group. Particularly preferred alkyl groups include, for example, methyl, ethyl, propyl, isopropyl, butyl, isobutyl, tert-butyl, pentyl and hexyl.

As used herein, the term "haloalkyl" refers to an alkyl group as described above in which one or more hydrogens are replaced by halo.

Where $R^a$ and/or $R^b$ are aryl, the aryl group is typically a $C_{6-12}$ aromatic group. Preferred examples include phenyl and naphthyl etc.

As used herein, the term "haloaryl" refers to an aryl group as described above in which one or more hydrogens are replaced by halo.

By way of example, the reaction of $KHSO_5$ (Oxone®) with a ketone of formula XVI would form a dioxirane of formula:

wherein $R^a$ and $R^b$ are as defined above.

More preferably, $R^a$ and $R^b$ are each independently alkyl or haloalkyl.

In a highly preferred embodiment, at least one of $R^a$ and $R^b$ is a haloalkyl, more preferably, $CF_3$ or $CF_2CF_3$.

In one preferred embodiment, $R^a$ and $R^b$ are each independently methyl or trifluoromethyl.

In one preferred embodiment of the invention, the ketone is selected from acetone and a 1,1,1-trifluoroalkyl ketone.

In a more preferred embodiment of the invention, the trifluoroalkyl ketone is 1,1,1-trifluoroacetone or 1,1,1-trifluoro-2-butanone, more preferably 1,1,1-trifluoro-2-butanone.

In one preferred embodiment the process of the invention comprises the step of converting a compound of formula (VII) into a compound of formula (VI)

(VII) → (VI)

Preferably the process comprises treating a compound of formula (VII) with tosyl chloride in pyridine. Alternatively the process comprises treating a compound of formula (VII) with tosyl chloride in dichloromethane and triethylamine.

In one preferred embodiment the process of the invention comprises the step of converting a compound of formula (VIII) into a compound of formula (VII)

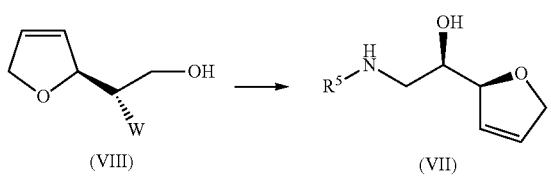

where W is halogen or tosyl.

Preferably, this step comprises the steps of:
(a) reacting a compound of formula (VIII), where W is halogen or OTs, with aqueous ammonia and alcohol; and
(b) converting the product formed in step (a) to a compound of formula (VII).

Preferably, steps (a) and (b) of the above process are a one-pot process.

In one particularly preferred embodiment, $R^5$ is benzyloxycarbonyl, and step (b) comprises treating the mixture formed in step (a) with benzyloxycarbonyl chloride.

Preferably, W is I, Br or OTs, more preferably, Br or OTs, even more preferably OTs.

Preferably, the alcohol is isopropyl alcohol or ethanol.

In one preferred embodiment of the invention, said compound of formula VIII is prepared from a compound of formula IX

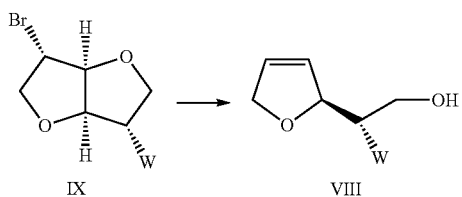

Preferably, the above process comprises treating said compound of formula IX with methyl lithium.

More preferably, compound of formula IX is compound 47 and compound of formula VIII is compound 14. Treatment of monobromotosylate 47 with zinc dust at room temperature in organic/aqueous mixtures (most preferably an isopropanol, tetrahydrofuran, water, ammonium chloride mixture) provides alcohol 14 respectively in high yield. Additionally, completion of the one-pot conversion gives alcohol VII and with defined stereochemistry and in high yield.

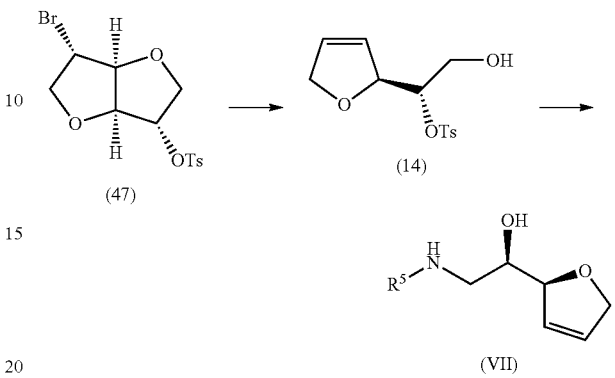

Commencing from the commercially available sugar isosorbide, the present invention also provides facile preparation of monobromotosylate 47. One highly preferred preparation is shown below in Scheme 15

Scheme 15: (a) TsCl, triethylamine, DCM, 25° C. → 50° C., 20 h under Ar; (b) LiBr, DMSO, 110° C., → 120°C., 10 h under Ar; (c) Zn, $^i$PrOH, THF, H$_2$O, NH$_4$Cl, RT, 16 h; (d) (i) NH$_4$OH, NH$_3$ in iPrOH, 75° C., 16 h; (ii) Cbz-Cl, Na$_2$CO$_3$, dioxane, water.

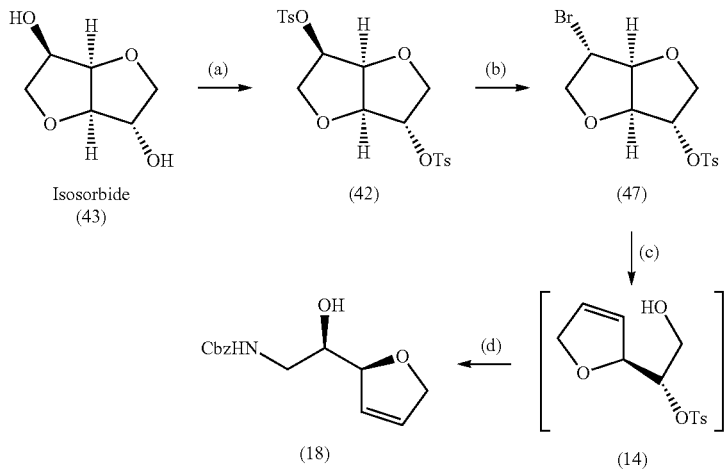

Isosorbide (43) is converted to the di-tosylate (42) which is obtained following recrystallisation from methanol in 97% yield. Mono-bromination is effected by 2.5 eq lithium bromide in DMSO (or DMF) with temperature control 110° C.→120° C. The product bromide is isolated following extractive work-up and purification either by column chromatography (74%) or attractive for large scale by recrystallisation from methanol giving a first crop of 55% plus mother liquors containing good quality material that may be pooled from batch runs and purified later. Thus, preparation of monobromotosylate (47) with defined stereochemistry by methods in Scheme 15 is attractive for large scale applications. Treatment of monobromotosylate (47) with zinc dust at room temperature in organic/aqueous mixtures (most preferably an isopropanol, tetrahydrofuran, water, ammonium chloride mixture) provides alcohol (14) which is derivatised as the Cbz compound (18) through one pot conversion.

In one highly preferred embodiment of the invention, the 6-Cl-5,5-bicylic core is prepared in accordance with the steps set forth in Scheme 1 below:

The alcohol functionality of (18) may be derivatised as the para-toluene sulphonate (Ts) giving (R)-2-(benzyloxycarbonylamino)-1-((S)-2,5-dihydrofuran-2-yl)ethyl 4-methylbenzenesulfonate (32b) which proceeds through the anti-epoxide (R)-2-(benzyloxycarbonylamino)-1-((1S,2S,5S)-3,6-dioxabicyclo[3.1.0]hexan-2-yl)ethyl 4-methylbenzenesulphonate (33b). Hydrogenation of tosylate (33b) provides free amine that undergoes intramolecular cyclisation to provide intermediate (74). Intermediate (74) undergoes displacement with an excess of lithium chloride in DMF at 130° C., to give the 6-chloro analogue with inversion of configuration. Urethane protection of the secondary amine of the bicyclic intermediate (69) followed by oxidation to ketone provides intermediate (71) that is particularly useful for solid phase synthesis of compounds of general formula I.

Advantageously, the epoxidation to give the desired anti-epoxide is directed by the presence of the tosylate group.

Alternatively, intermediate tosylate (74) may be Cbz protected to give protected analogue (34b) that may undergo inversion to chloride (68) through treatment with LiBr in DMF at typically 130° C. (Scheme 1).

Synthesis of Compounds of Formula (I)

To those skilled in the practices of organic chemistry, compounds of general formula (I) may be readily synthesised by a number of chemical strategies, performed either in solution or on the solid phase (see Atherton, E. and Sheppard, R. C. In 'Solid Phase Peptide Synthesis: A Practical Approach', Oxford University Press, Oxford, U.K. 1989, for a general review of solid phase synthesis principles), or a combination thereof.

Compounds of general formula (I) may be conveniently considered as a combination of three building blocks (P1, P2 and P3) that respectively occupy the S1, S2 and S3 binding sites of the protease (see Berger, A. and Schechter, I., *Philos. Trans. R. Soc. Lond. [Biol.]*, 257, 249-264, 1970 for a description of the designation of enzyme S-subsites and substrate P-subsites within enzyme-substrate or enzyme-inhibitor complexes). The notional concepts of P1, P2 and P3 are used

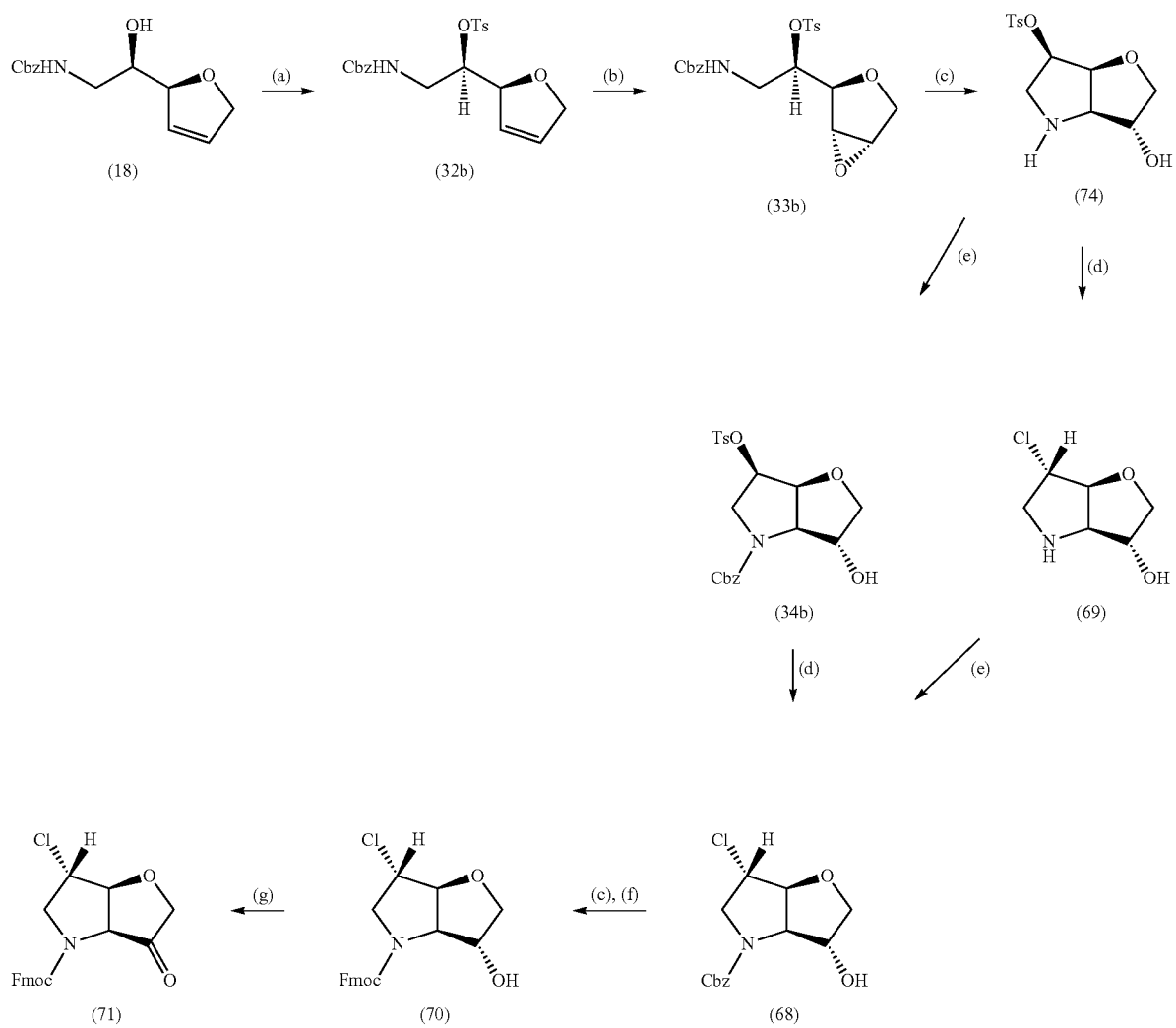

Scheme 1: (a) TsCl, pyridine: (b) (i) mCPBA, DCM or (ii) OXONE®, NaHCO₃, 1,1,1-trifluoroacetone, CH₃CN, H₂O, Na₂•EDTA 0° C. or (iii) 30% H₂O₂, CH₃CN, MeOH, NaHCO₃; (c) Pd—C, H₂, ethanol; (d) LiCl, DMF; 130° C.; (e) Cbz—Cl, Na₂CO₃, dioxane, H₂O; (f) Fmoc—Cl, Na₂CO₃, dioxane, H₂O; (g) Dess-Martin periodinane, anhydrous DCM, RT.

herein for convenience only and the above-mentioned compounds are intended to be within the scope of the invention regardless of binding mode.

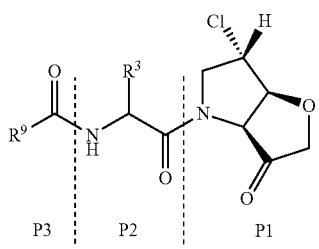

A suitably protected and/or activated building block may then be prepared and subsequently chemically bonded (coupled) together with other building blocks to provide compounds of general formula (I).

Compounds of formula (I) may be prepared: (1) by the stepwise addition of P3 and P2 to the bicyclic 6-(S)-chlorotetrahydrofuro[3,2-b]pyrrol-3-one core; or (2) by reaction of the bicyclic 6-(S)-chlorotetrahydrofuro[3,2-b]pyrrol-3-one core with a P3-P2 prescursor molecule; or (3) by introducing the P3-P2 group prior to formation of the bicyclic 6-(S)-chlorotetrahydrofuro[3,2-b]pyrrol-3-one core, i.e. prior to the oxidation step or prior to the intramolecular cyclisation step.

Thus, alternative orders of coupling of the building blocks are possible, for example P2+P1→P2-P1 then addition of P3→P3-P2-P1 or P3+P2→P3-P2 then addition to P1→P3-P2-P1. Within each of these combinations each of the P1, P2 or P3 building blocks may contain additional alternative functionalities that are further transformed following coupling to give the final compound. For example the ketone functionality of the P1 building block may be protected as a ketal during coupling of building blocks and transformed to the final ketone by hydrolysis following completion of the coupling reactions. Alternatively, the ketone functionality of the P1 building block may be initially introduced via a lower oxidation state such as the corresponding alcohol and following completion of the coupling reactions be re-introduced by oxidation of the alcohol. Alternatively, the ketone functionality of the P1 building block may be protected through a semi-carbazone suitable for solid phase synthesis (e.g. see WO 02/057270 and references cited therein) and following completion of the coupling reactions released from the solid phase by acidolytic reaction.

The chemical bond formed by coupling of the building blocks is a secondary amide (P3-P2) or a tertiary amide (P2-P1) that is formed through reaction of an activated carboxylic acid with a primary and secondary amine respectively. Many methods are available for activation of a carboxylic acid prior to coupling to an amine and in principle, any of these methods may be used herein. Typical carboxylic acid activation methods are exemplified but not restricted to the azide method, mixed anhydride method (e.g. via isobutylchloroformate), carbodiimide methods (e.g. via dicyclohexylcarbodiimide, diisopropylcarbodiimide, 1-ethyl-3-(3'-dimethylamino propyl)carbodiimide), active ester method (e.g. via p-nitrophenyl ester, N-hydroxysuccinic imido ester, pentafluorophenyl ester), uronium method (e.g. via addition of HBTU, PyBop, BOP), carbonyldiimidazole method or via pre-formation of acyl fluorides or acyl chlorides. In some instances the coupling reaction may be enhanced by the addition of a further activation catalyst such as 1-hydroxybenzotriazole, or 4-dimethylaminopyridine. A general description of carboxylic acid activation techniques and the use of activation additives may be found in Bodanszky, M. 'Principles of Peptide Synthesis', $2^{nd}$ rev. ed., Springer-Verlag, Berlin, 1993 and references cited therein.

The α-amino group of the P2 amino acid building block is usually protected during coupling reactions to the P1 building block to avoid the formation of undesired self-condensation products. The art of α-amino protection is well known in peptide chemistry (e.g. see Bodanszky, M. 'Principles of Peptide Synthesis', $2^{nd}$ rev. ed., Springer-Verlag, Berlin, 1993 and references cited therein) and example protection groups include, but are not limited to, 9-fluorenylmethoxycarbonyl (Fmoc), tert-butoxycarbonyl (Boc), benzyloxycarbonyl (Cbz), allyloxycarbonyl (Alloc) and trichloroethoxycarbonyl (Treoc). The Fmoc group is particularly well suited for solid phase syntheses (e.g. see Atherton, E.; Sheppard, R. C. in 'Solid Phase Peptide Synthesis A Practical Approach', IRL Press, Oxford, U.K., 1989) typically being removed by treatment with 20% v/v piperidine in dimethylformamide or 1% v/v 1,8-diazabicyclo[5.4.0]undec-7-ene in dimethylformamide. The Boc group is particularly well suited to solution phase syntheses typically being removed by treatment with trifluoroacetic acid based mixtures or HCl in dioxane or ethyl acetate. The Cbz group is also particularly well suited for solution phase syntheses typically being removed by catalytic hydrogenation with hydrogen and palladium catalysis or by treatment with HBr in acetic acid. Once the coupling sequence is complete, any protecting groups are removed in whatever manner is dictated by the choice of protecting groups (for a general description of protecting groups and their respective stabilities and methods of removal see Greene, T. W. and Wuts, P. G. M. 'Protective Groups in Organic Synthesis' John Wiley and Sons, New York, 1991 and references therein).

In the simplest example, the entire left hand portion of a compound of general formula (I) (i.e. P3-P2) as the carboxylic acid can be prepared in solution by traditional organic chemistry methods and coupled to ketone, alcohol or ketal intermediates such as compounds (IIb), (IIc) and (IId). Then oxidation of the alcohol intermediate (e.g. Dess-Martin periodinane in DCM) or acidolytic cleavage of the ketal intermediate provides compounds of general formula (I). The alcohol oxidation route is particularly useful when the compound of general formula (I) contains a substituent that is labile to trifluoroacetic acid, this being the final reagent used in each of the solid phase syntheses.

(IIb)

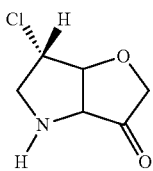

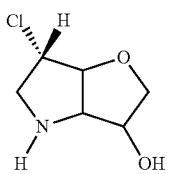

(IIc)

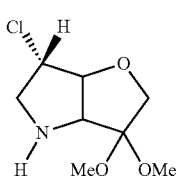

(IId)

Examples of these different coupling tactics have been detailed previously (see (i) Quibell, M. et. al., *Bioorg. Med. Chem.* 13, 609-625, 2005. (ii) Wang, Y. et. al., *Bioorg. Med. Chem. Lett.* 15, 1327-1331, 2005) and the optimum synthetic route is dependant upon the specific substituent combinations of the target compound of general formula (I).

In more detail, one preferred strategy for the synthesis of compounds of general formula (I) comprises:—
(a) Preparation of an appropriately functionalised and protected bicyclic ketone or bicyclic alcohol building block in solution;
(b) Attachment of the building block (a) to the solid phase through a linker that is stable to the conditions of synthesis, but readily labile to cleavage at the end of a synthesis (see James, I. W., *Tetrahedron*, 55 (Report №489), 4855-4946, 1999, for examples of the 'linker' function as applied to solid phase synthesis);
(c) Solid phase organic chemistry (see Brown, R. D. *J. Chem. Soc., Perkin Trans.* 1, 19, 3293-3320, 1998), to construct the remainder of the molecule;
(d) Compound cleavage from the solid phase into solution; and
(e) Cleavage work-up and compound analysis.

A second strategy for the synthesis of compounds of general formula (I) comprises:—

(a) Preparation of an appropriately functionalised and protected bicyclic intermediate building block in solution. Preferred protecting groups for solution phase chemistry are the 9-fluorenylmethoxycarbonyl (Fmoc), Nα-tert-butoxycarbonyl (Boc), Nα-benzyloxycarbonyl (Cbz) and Nα-allyloxycarbonyl group (Alloc).
(b) Standard organic chemistry methods for the conversion of building block obtained in step (a) towards compounds of general formula (I).

As mentioned above, in one preferred embodiment of the invention, compounds of formula (I) may be prepared using conventional solution phase chemistry, for example, as described in Quibell, M et al, Bioorg. Med. Chem., 13, 609-625, 2005 (see in particular, Schemes 3 and 4). The solution phase strategy is attractive in being able to generate larger quantities of preferred analogues, typically on a multi-gram to multi-kilogram scale.

In an alternative preferred embodiment of the invention, compounds of formula (I) may be prepared using conventional solid phase chemistry, for example, as described in Quibell M, et al Bioorg. Med. Chem., 12, 5689-5710, 2004, see in particular, Scheme 3 and Section 3.2, and references cited therein; and Bioorg. Med. Chem., 13, 609-625, 2005, see Scheme 5 and Section 2.2, and references cited therein). The solid phase strategy is attractive in being able to generate many thousands of analogues, typically on a 5-100 mg scale, through established parallel synthesis methodologies (e.g. see (a) Bastos, M.; Maeji, N. J.; Abeles, R. H. *Proc. Natl. Acad. Sci. USA,* 92, 6738-6742, 1995).

The synthetic strategy is based on reversible anchorage of the ketone functionality via a hydrazide linker bond using general multipin techniques previously described in the art (Watts J. et al, Bioorg. Med. Chem. 12 (11), 2903, 2004; Quibell M., et al, Bioorg. Med. Chem. 5689-5710, 2004; Grabowksa U. et al, J. Comb. Chem. 2000, 2 (5), 475).

Compounds of formula (III; $R^5$=Fmoc) may be oxidised to the corresponding ketone (e.g. XVI, Scheme 3) and utilised in a solid phase synthesis of inhibitor molecules (I). The solid phase linkage of an aldehyde or ketone, has previously been described by a variety of methods (e.g. see (a) James, I. W., 1999, (b) Lee, A., Huang, L., Ellman, J. A., *J. Am. Chem. Soc,* 121 (43), 9907-9914, 1999, (c) Murphy, A. M., et al, J. Am. Chem. Soc, 114, 3156-3157, 1992). A suitable method amenable to the reversible linkage of an alkyl ketone functionality is through a combination of the previously described chemistries. The semicarbazide, 4-[[(hydrazinocarbonyl)amino]methyl]cyclohexane carboxylic acid. trifluoroacetate (Murphy, A. M., et al, J. Am. Chem. Soc, 114, 3156-3157, 1992), may be utilised as illustrated in Scheme 3, exemplified by linkage of the Fmoc protected 6-(S)-chlorotetrahydrofuro[3,2-b]pyrrol-3-one (71).

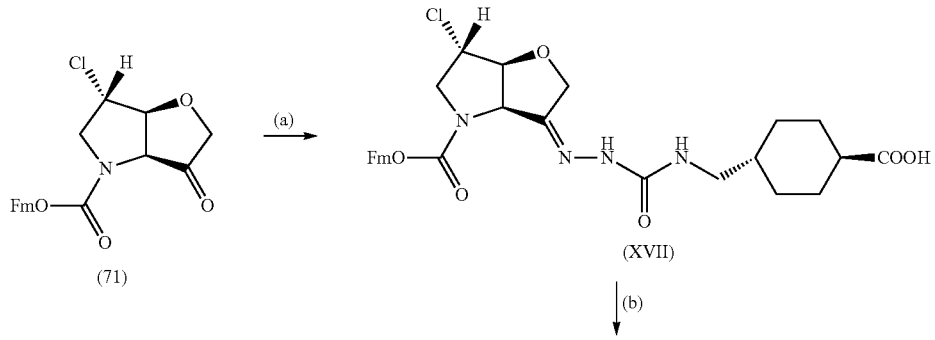

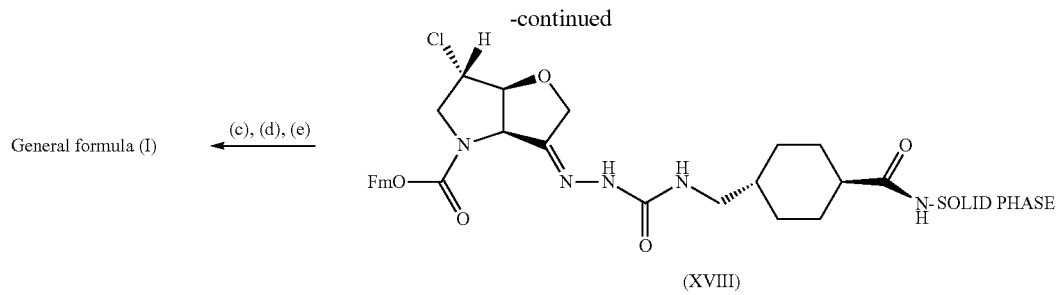

(XVIII)

Scheme 3: (a) (71) in 90% EtOH/H$_2$O/1.5eq NaOAc/4-[[(hydrazinocarbonyl)-amino]methyl]-cyclohexane carboxylic acid•trifluoroacetate, 2 hr reflux. (b) 3eq construct (XVII)/3eq HBTU/3eq HOBt/6eq NMM, NH$_2$-SOLID PHASE, DMF, RT, o/n. (c) 20% piperidine/DMF, 30 mins. (d) Range of chemistries to introduce P3-P2 (e) TFA/H$_2$O (95:5, v/v), RT, 2 hr.

Construct (XVII) is prepared through reaction of the linker molecule and the 6-(S)-chlorotetrahydrofuro[3,2-b]pyrrol-3-one (71) by refluxing in aqueous ethanol/sodium acetate. Standard solid phase techniques (e.g. see Atherton, E. and Sheppard, R. C., 1989) are used to anchor the construct to an amino-functionalised solid phase through the free carboxylic acid functionality of (XVII), providing the loaded construct (XVIII). Loaded construct (XVIII) be reacted with a wide range of carboxylic acids available commercially or in the literature, to introduce the left-hand portion 'P3-P2'.

Preferred carboxylic acids for the introduction of the [R$^9$—CO] synthon are known in the literature with the following representative examples; furan-2-carboxylic acid, 5-chlorofuran-2-carboxylic acid, thiophene-2-carboxylic acid, 5-chlorothiophene-2-carboxylic acid, furan-3-carboxylic acid, 5-chlorofuran-3-carboxylic acid, thiophene-3-carboxylic acid, 5-chlorothiophene-3-carboxylic acid, oxazole-2-carboxylic acid, oxazole-5-carboxylic acid, 1,3,4-oxadiazole-2-carboxylic acid, thiazole-2-carboxylic acid, thiazole-5-carboxylic acid, 1,3,4-thiadiazole-2-carboxylic acid, benzoic acid, 3-methylbenzoic acid, 3-chlorobenzoic acid, 3-fluorobenzoic acid, 3-bromobenzoic acid, 3-methoxybenzoic acid, 3-nitrobenzoic acid, 3,5-difluorobenzoic acid, nicotinic acid (CAS 59-67-6), 5-fluoronicotinic acid, 5-chloronicotinic acid, 5-methoxynicotinic acid, 5-nitronicotinic acid, pyrimidine-5-carboxylic acid (CAS 4595-61-3), isonicotinic acid, 2-fluoroisonicotinic acid, 3-(1H-pyrrol-1-yl)benzoic acid (CAS 61471-45-2), 3-(1H-pyrazol-1-yl)benzoic acid (CAS 264264-33-7), 3-(1H-imidazol-1-yl)benzoic acid (CAS 108035-47-8), 3-(1H-1,2,3-triazol-1-yl)benzoic acid (CAS 335255-82-8), 3-(4H-1,2,4-triazol-4-yl)benzoic acid (CAS 335255-80-6), 3-(1H-1,2,4-triazol-1-yl)benzoic acid (CAS 167626-64-4), 3-(1H-tetrazol-1-yl)benzoic acid (CAS 204196-80-5), 3-(2H-1,2,3-triazol-2-yl)benzoic acid (CAS 90556-58-4), 3-(1H-imidazol-5-yl)benzoic acid (CAS 912569-71-2), 3-(1H-imidazol-2-yl)benzoic acid (CAS 391668-62-5), 3-(4H-1,2,4-triazol-3-yl)benzoic acid (CAS 876715-37-6), 3-(1H-tetrazol-5-yl)benzoic acid (CAS 73096-39-6), 3-(1H-pyrazol-3-yl)benzoic acid (CAS 850375-11-0), 3-(furan-2-yl)benzoic acid (CAS 35461-99-5), 3-(thiophen-2-yl)benzoic acid (CAS 29886-63-3), 3-(isoxazol-5-yl)benzoic acid (852180-44-0), 3-(isothiazol-5-yl)benzoic acid (CAS 904085-98-9), 3-(oxazol-5-yl)benzoic acid (CAS 252928-82-8), 3-(thiazol-5-yl)benzoic acid (CAS 252928-84-0), 3-(oxazol-2-yl)benzoic acid (CAS 473538-18-0), 3-(thiazol-2-yl)benzoic acid (CAS 847956-27-8), 3-(furan-3-yl)benzoic acid, (CAS 168619-07-6), 3-(thiophen-3-yl)benzoic acid (CAS 20608-89-3), 3-(2-methylthiazol-4-yl)benzoic acid (CAS 28077-41-0), 3-(1,2,4-oxadiazol-3-yl)benzoic acid (CAS 912577-30-1), 3-(1-methyl-1H-pyrazol-3-yl)benzoic acid (CAS 915707-39-0), 3-(2-methyl-1H-imidazol-1-yl)benzoic acid (CAS 898289-59-3), 3-(3-methyl-1,2,4-oxadiazol-5-yl)benzoic acid (CAS 915707-45-8), 3-(1-methyl-1H-pyrazol-5-yl)benzoic acid (CAS 628297-55-2), 3-(pyridin-4-yl)benzoic acid, 3-(pyrimidin-4-yl)benzoic acid, 3-(pyridin-3-yl)benzoic acid (CAS 4385-77-7), 3-(pyrimidin-5-yl)benzoic acid (CAS 852180-74-6), 3-(pyridin-2-yl)benzoic acid (CAS 4467-07-6), 3-(pyrimidin-2-yl)benzoic acid (CAS 579476-26-9), benzo[d]thiazole-6-carboxylic acid (3622-35-3), 1H-indole-5-carboxylic acid (1670-81-1), 1H-benzo[d][1,2,3]triazole-6-carboxylic acid (23814-12-2), benzo[d][1,2,5]oxadiazole-5-carboxylic acid (19155-88-5), 6-hydroxypicolinic acid (19621-92-2), 2,3-dioxo-1,2,3,4-tetrahydroquinoxaline-6-carboxylic acid, 2-oxo-1,2,3,4-tetrahydroquinoline-6-carboxylic acid (CAS 70639-77-9), 2-oxoindoline-5-carboxylic acid (CAS 102359-00-2), 2-oxoindoline-6-carboxylic acid (CAS 334952-09-9), 2,3-dioxoindoline-5-carboxylic acid (CAS 25128-32-9), 3-oxo-3,4-dihydro-2H-benzo[b][1,4]oxazine-7-carboxylic acid (CAS 214848-62-1), 4-(methylsulfonamido)benzoic acid (CAS 7151-76-0), 2-oxo-2,3,4,5-tetrahydro-1H-benzo[b]azepine-7-carboxylic acid (CAS 117030-69-0).

The present invention is further described by way of example.

EXAMPLES

General Procedures

Solvents were purchased from ROMIL Ltd, U.K. at SpS or Hi-Dry grade unless otherwise stated. $^1$H NMR and $^{13}$C NMR were obtained on a Bruker DPX400 (400 MHz $^1$H frequency and 100 MHz $^{13}$C frequency; QXI probe) or Bruker Avance 500 MHz (TXI probe with ATM) in the solvents indicated. Chemical shifts are expressed in parts per million (δ) and are referenced to residual signals of the solvent. Coupling constants (J) are expressed in Hz. All analytical HPLC were obtained on Phenomenex Jupiter C$_4$, 5μ, 300 Å, 250×4.6 mm, using mixtures of solvent A (0.1% aq trifluoroacetic acid (TFA)) and solvent B (90% acetonitrile/10% solvent A) on automated Agilent systems with 215 and/or 254 nm UV detection. Unless otherwise stated a gradient of 10 to 90% B in A over 25 min at 1.5 mL/min was performed for full analytical HPLC. HPLC-MS analysis was performed on an Agilent 1100 series LC/MSD, using automated Agilent HPLC systems, with a gradient of 10 to 90% B in A over 10 min on Phenomenex Luna C$_8$, 5μ, 300 Å, 50×2.0 mm at 0.6 mL/min. Semi-preparative HPLC purification was performed on Phenomenex Jupiter C$_4$, 5μ, 300 Å, 250×10 mm, using a gradient of 10 to 90% B in A over 25 min at 4 mL/min on automated Agilent systems with 215 and/or 254 nm UV detection. Flash column purification was performed on silica gel 60 (Merck 9385) or using isolute SPE flash silica columns (Biotage, Hengoed, UK).

Preparation of Benzyl (R)-2-((S)-2,5-dihydrofuran-2-yl)-2-hydroxyethyl carbamate (18). (i) Preparation of (3R,3aS,6S,6aS)-hexahydrofuro[3,2-b]furan-3,6-diyl bis(4-methylbenzenesulfonate) (42). A stirred solution of p-toluenesulfonyl chloride (57.4 g, 301 mmol) and isosorbide (43) (20 g, 137 mmol) in pyridine (315 mL) was heated at 95° C. for 4.5 hours under an atmosphere of argon then stood at ambient temperature for 16 hours before being poured onto iced-water (1 L). The aqueous was extracted with dichloromethane (2×500 mL), then the combined organic layers were washed with water (2×500 mL), then dried ($Na_2SO_4$), filtered then reduced in vacuo to leave a viscous oil (65.22 g). The oil was crystallized from hot methanol (350 mL). The white solid was collected by filteration in vacuo, then washed with methanol (100 mL) and dried in vacuo to obtain ditosylate (42) as a white solid (45.87 g, 74%). TLC ($R_f$=0.30, EtOAc:heptane 2:3), analytical HPLC single main peak, $R_t$=20.219 min., HPLC-MS 455.1 $[M+H]^+$, 931.2 $[2M+Na]^+$, $[\alpha]_D^{20}$+57.2° (c=10.2, $CHCl_3$); $\delta_H$ (500 MHz, $CDCl_3$) 2.44 (6H, s, $CH_3$), 3.68 (1H, dd, J=9.80 and 6.46 Hz, $CH_2$), 3.82-3.87 (2H, m, $CH_2$), 3.94 (1H, d, J=11.28 Hz, $CH_2$), 4.46 (1H, d, J=4.44 Hz, CHCHOTs), 4.58 (1H, t, J=4.74 Hz, CHCHOTs), 4.82-4.86 (2H, m, CHOTs), 7.32-7.36 (4H, m, aromatic $CH_3CCH$), 7.74-7.80 (4H, m, aromatic $OSO_2CCH$).

(ii) Preparation of (3S,3aS,6S,6aS)-6-bromohexahydrofuro[3,2-b]furan-3-yl 4-methylbenzenesulfonate (47). Lithium bromide (9.6 g, 110.1 mmol) was added to a stirred solution of ditosylate (42) (20.0 g, 44.05 mmol) in dimethylformamide (100 mL) under an atmosphere of argon. The mixture was heated at 110° C. for 5 hours then stood at ambient temperature for 3 days, then heated at 90° C. for 3.5 hours. The mixture was diluted with water (250 mL) extracted with tert-butyl methyl ether (4×125 mL) then the organic phase washed with water (3×125 mL), brine (125 mL), dried ($MgSO_4$), filtered and reduced in vacuo to leave a brown oil (16.8 g). Flash chromatography over silica, eluting with ethyl acetate:heptane mixtures 0:100 to 30:70 gave bromotosylate (47) (11.88 g, 74%) as a pale yellow solid. TLC ($R_f$=0.20, EtOAc:heptane 1:3); analytical HPLC main peak, $R_t$=18.050 min; HPLC-MS 381.0/383.0 $[M+H_2O+H]^+$, 385.0/387.0 $[M+Na]^+$; $[\alpha]_D^{18}$+51.0° (c=5.0, $CHCl_3$); $\delta_H$ (500 MHz, $CDCl_3$) 2.45 (3H, s, $CH_3$), 3.84 (1H, dd, J=11.19 and 3.51 Hz, $CH_2$), 4.05-4.15 (3H, m, $CH_2$), 4.28 (1H, d, J=3.40 Hz, CHBr), 4.78 (1H, d, J=3.37 Hz, CHCH), 4.84 (1H, d, J=3.42 Hz, CHOTs), 4.90 (1H, d, J=3.37 Hz, CHCH), 7.36 (2H, brd, J=7.98 Hz, aromatic $CH_3CCH$), 7.79 (2H, brd, J=8.32 Hz, aromatic $OSO_2CCH$).

(iii) Preparation of (S)-1-((S)-2,5-dihydrofuran-2-yl)-2-hydroxyethyl 4-methyl benzenesulfonate (14). Ammonium chloride (20 mg, 0.37 mmol) then zinc dust (20 mg, 0.31 mmol) were added to a solution of bromotosylate (47) (100 mg, 0.28 mmol) in ethanol (1.5 mL) under argon. The mixture was stirred for 16 hours before filtering the suspension through celite in vacuo. The filter cake was washed with ethanol (20 mL) then the filtrate reduced in vacuo to leave a residue (111 mg). Flash chromatography over silica, eluting with ethyl acetate:heptane mixtures 20:80 to 40:60 gave alcohol (14) (53 mg, 68%) as a white solid. TLC ($R_f$=0.15, EtOAc: heptane 1:2); analytical HPLC main peak, $R_t$=12.543 min; HPLC-MS 285.1 $[M+H]^+$, 302.1, 591.2 $[2M+Na]^+$; $[\alpha]_D^{15}$-86.8° (c=5.3, $CHCl_3$); $\delta_H$ (500 MHz, $CDCl_3$) 2.12 (1H, brs, OH), 2.44 (3H, s, aryl-$CH_3$), 3.77 (2H, d, J=4.85 Hz, $CH_2OH$), 4.54-4.58 (3H, m, $CH_2OCH$), 4.94-4.98 (1H, m, CHOTs), 5.64-5.67 and 5.97-6.00 (2H total, m, $CH_2CH=CH$), 7.33 (2H, brd, J=8.23 Hz, aromatic $CH_3CCH$), 7.79 (2H, brd, J=8.31 Hz, aromatic $OSO_2CCH$); $\delta_C$ (125 MHz, $CDCl_3$) 21.660 ($CH_3$), 62.303 ($CH_2OH$), 75.940 ($OCH_2CH=CH$), 82.720 and 85.221 (OCHCHOTs), 124.792, 127.977, 129.479 and 129.749 ($OCH_2CH=CH$ and aromatic CH), 133.496 ($CHOSO_2C$ quaternary), 144.973 ($CH_3C$ quaternary).

(iv) Alternative preparation of (S)-1-((S)-2,5-dihydrofuran-2-yl)-2-hydroxyethyl 4-methyl benzenesulfonate (14). A solution of ammonium chloride (200 mg, 3.7 mmol) in water (2.5 mL) then zinc dust (200 mg, 3.1 mmol) were added to a solution of bromotosylate (47) (1 g, 2.75 mmol) in tetrahydrofuran (10 mL) and propan-2-ol (5 mL) under argon. The mixture was stirred for 16 hours before filtering the suspension through celite in vacuo. The filter cake was washed with diethyl ether (20 mL). Hydrochloric acid (1M, 20 mL) was added to the filtrate then the organic phase separated. The aqueous layer was extracted with diethyl ether (20 mL) then the combined organic phase was washed with brine (20 mL), then dried ($MgSO_4$), filtered and reduced in vacuo to leave a residue (1.06 g). Flash chromatography over silica, eluting with ethyl acetate:heptane mixtures 20:80 to 50:50 gave alcohol (14) (528 mg, 68%) as a white solid. $[\alpha]_D^{16}$-82.7° (c=11.3, $CHCl_3$).

(v) Preparation of benzyl (R)-2-((S)-2,5-dihydrofuran-2-yl)-2-hydroxyethylcarbamate (18). Zinc and 'One-pot' procedure. A solution of ammonium chloride (600 mg, 11.2 mmol) in water (7.5 mL) was added to a solution of bromotosylate (47) (3.0 g, 8.26 mmol) in propan-2-ol (15 mL) under argon. Zinc dust (600 mg, 9.2 mmol) was then added in portions over 4 minutes and the mixture was stirred for 16 hours before filtering the suspension through celite in vacuo. The filter cake was washed with diethyl ether (60 mL). Hydrochloric acid (1M, 60 mL) was added to the filtrate then the organic phase separated. The aqueous layer was extracted with diethyl ether (60 mL) then the combined organic phase was washed with brine (60 mL), then dried ($MgSO_4$), filtered and reduced in vacuo. The residue was dissolved in ammonium hydroxide (18 mL) and a solution of ammonia in propan-2-ol (12 mL, 2.0M, 24 mmol), then divided into two equal portions and heated in sealed tubes at 75° C. for 16 hours. The mixtures were combined using methanol then the solvents were removed in vacuo. The residue was azeotroped with diethyl ether (3×10 mL) to obtain (R)-2-amino-1-((S)-2,5-dihydrofuran-2-yl)ethanol which was used without further purification.

A solution of sodium carbonate (1.84 g, 17.4 mmol) in water (16 mL) was added whilst stirring to a suspension of (R)-2-amino-1-((S)-2,5-dihydrofuran-2-yl)ethanol (assumed to be 8.26 mmol) in 1,4-dioxane (20 mL). The mixture was cooled to 0° C. then benzylchloroformate (1.77 mL, 12.4 mmol) was added dropwise over 5 minutes. The mixture was stirred at 0° C. for 55 minutes then dichloromethane (75 mL) and water (100 mL) added. The organic phase was separated and the aqueous extracted with dichloromethane (2×50 mL). The organic phase was washed with brine (50 mL), then dried ($Na_2SO_4$), filtered and reduced in vacuo to leave a residue (3.7 g). Flash chromatography over silica, eluting with ethyl acetate: heptane mixtures 20:80 to 70:30 gave alcohol (18) (1.26 g, 58%). $[\alpha]_D^{16}$-62.0° (c=5.0, $CHCl_3$).

Preparation of (R)-2-(benzyloxycarbonylamino)-1-((S)-2,5-dihydrofuran-2-yl)ethyl 4-methyl benzenesulfonate (32b). A solution of p-toluenesulfonyl chloride (368 mg, 2.03 mmol) in pyridine (1.5 mL) was added to alcohol (18) (333 mg, 1.27 mmol). The mixture was stirred at 14° C. for 16 hours and at 24° C. for 3.5 hours then diluted with tert-butyl methyl ether (35 mL). The organic layer was washed with water (15 mL), brine (15 mL), then dried (MgSO$_4$), filtered and reduced in vacuo to leave a pale yellow oil (0.712 g). Flash chromatography over silica, eluting with ethyl acetate: heptane mixtures 15:85 to 30:70 gave tosylate (32b) (429 mg, 81%) as a white solid. TLC (R$_f$=0.75, EtOAc:heptane 3:1), analytical HPLC single main peak, R$_t$=18.93 min., HPLC-MS 374.2, 418.2 [M+H]$^+$, 857.3 [2M+Na]$^+$; [α]$_D^{18.5}$–30.2° (c=1.326, CHCl$_3$); δ$_H$ (500 MHz, CDCl$_3$) 2.39 (3H, s, aryl-CH$_3$), 3.29-3.37 and 3.53-3.62 (2H total, m, CH$_2$NH), 4.44-4.50 and 4.52-4.57 (2H total, m, OCH$_2$CH=CH), 4.59-4.65 (1H, m, OCHCH=CH), 4.87-4.92 (1H, m, CHOTs), 5.05 (2H, m, OCH$_2$Ph), 5.03 (1H, brs, NH), 5.69-5.73 and 5.94-5.98 (2H total, m, CH$_2$CH=CH), 7.28 (2H, d, J=8.10 Hz, aromatic CH$_3$CCH), 7.29-7.37 (5H, phenyl CH), 7.77 (2H, d, J=8.10 Hz, aromatic OSO$_2$CCH); δ$_C$ (125 MHz, CDCl$_3$) 21.627 (aryl-CH$_3$), 41.119 (CH$_2$NHCbz), 66.856 (CH$_2$Ph), 75.987 (OCH$_2$CH=CH), 82.352 (CHOTs), 85.622 (OCHCH=CH), 124.792, 127.825, 128.027, 128.126, 128.504, 129.357 and 129.537 (OCH$_2$CH=CH and aromatic CH), 133.674 (CHOSO$_2$C quaternary), 136.348 (Cbz quaternary), 144.941 (CH$_3$C quaternary), 156.273 (Cbz C=O).

Epoxidation Studies with (R)-2-(benzyloxycarbonylamino)-1-((S)-2,5-dihydro furan-2-yl)ethyl 4-methylbenzenesulfonate (32b)

(a) 3-Chloroperbenzoic acid (97 mg, ≦77%, 0.43 mmol) was added to a stirred solution of alkene (32b) (36 mg, 0.086 mmol) in dichloromethane (1.5 mL). The mixture was stirred for 20 hours at ambient temperature then 3-chloroperbenzoic acid (97 mg, ≦77%, 0.43 mmol) was added and stirring continued for 1 day at 24° C. then diluted with dichloromethane (15 mL). The organic phase was washed with aqueous sodium hydroxide solution (5%, 10 mL), water (10 mL), then dried (Na$_2$SO$_4$), filtered and reduced in vacuo to leave a residue (0.038 mg). Flash chromatography over silica, eluting with ethyl acetate: heptane mixtures 10:90 to 50:50 gave (in order of elution) anti-(33b) (16 mg, 43%) as a colourless viscous oil and syn-epoxide (9 mg, 24%) as a white solid. Data for anti-(33b); TLC (R$_f$=0.50, EtOAc:heptane 1:1), analytical HPLC single main peak, R$_t$=17.999 min., HPLC-MS 434.1 [M+H]$^+$, 456.1 [M+Na]$^+$, 889.2 [2M+Na]$^+$; [α]$_D^{17}$+25.6° (c=2.54, CHCl$_3$); δ$_H$ (500 MHz, CDCl$_3$) 2.41 (3H, s, aryl-CH$_3$), 3.31-3.38 and 3.60-3.66 (2H total, m, CH$_2$NH), 3.67 (1H, d, J=10.46 Hz, OCH$_2$CH), 3.75 and 3.81 (each 1H, d, J=2.50 and 2.75 Hz respectively, OCH$_2$CHCH), 3.94 (1H, d, J=10.57 Hz, OCH$_2$CH), 4.07 (1H, d, J=6.90 Hz, OCHCHOTs), 4.60-4.64 (1H, m, CHOTs), 4.97-5.01 (1H brt, NH), 5.08 (2H, brs, CH$_2$Ph), 7.29-7.37 (7H, aromatic CH$_3$CCH and phenyl CH), 7.78 (2H, d, J=8.18 Hz, aromatic OSO$_2$CCH); δ$_C$ (125 MHz, CDCl$_3$) 21.665 (aryl-CH$_3$), 42.054 (CH$_2$NHCbz), 56.175 and 57.048 (OCH$_2$CHCH), 67.031 (CH$_2$Ph), 67.672 (OCH$_2$CH), 76.732 (OCHCHOTs), 79.388 (CHOTs), 127.776, 128.108, 128.222, 128.544 and 130.043 (aromatic CH), 133.249 (CHOSO$_2$C quaternary), 136.192 (Cbz quaternary), 145.487 (CH$_3$C quaternary), 156.224 (Cbz C=O).

(b) To a solution of alkene (32b) (262 mg, 0.63 mmol) in acetonitrile (4 mL) and aqueous Na$_2$.EDTA (4 mL, 0.4 mmol solution) at 0° C. was added 1,1,1-trifluoroacetone (0.67 mL, 7.54 mmol) via a pre-cooled syringe. To this solution was added in portions a mixture of sodium bicarbonate (0.44 g, 5.28 mmol) and OXONE® (1.20 g, 1.95 mmol) over a period of 55 minutes. The mixture was stirred for 2.5 hours then diluted with water (25 mL) and the product extracted into dichloromethane (2×25 mL). The combined organic layers were washed with brine (12.5 mL) then dried (Na$_2$SO$_4$), filtered and reduced in vacuo to leave a residue (310 mg). Flash chromatography over silica, eluting with ethyl acetate: heptane mixtures 15:85 to 50:50 gave anti-(33b) as a viscous white oil (216 mg, 79%).

Preparation of (3R,3aR,6R,6aS)-3-hydroxyhexahydro-2H-furo[3,2-b]pyrrol-6-yl 4-methylbenzenesulfonate (74). Ethanol (1.5 mL) was added dropwise to a mixture of 10% palladium on charcoal (20 mg) and anti-(33b) (100 mg, 0.25 mmol) under an atmosphere of argon. The argon was replaced by hydrogen then the suspension was stirred for 4.5 hours before filtering the mixture through celite in vacuo. The filter cake was washed with ethanol (10 mL) then the solvents removed in vacuo from the filtrate. The residue was azeotroped with toluene (2×3 mL) to obtain (3R,3aR,6R,6aS)-3-hydroxyhexahydro-2H-furo[3,2-b]pyrrol-6-yl 4-methylbenzenesulfonate (74) which was used without further purification. TLC (R$_f$=0.01, EtOAc:heptane 1:1), HPLC-MS 300.1 [M+H]$^+$, 621.2 [2M+Na]$^+$.

Preparation of (3R,3aR,6R,6aS)-benzyl 3-hydroxy-6-(tosyloxy)tetrahydro-2H-furo[3,2-b]pyrrole-4(5H)-carboxylate (34b). A solution of sodium carbonate (6.2 mg, 0.058 mmol) in water (0.15 mL) was added whilst stirring to a solution of aminoalcohol (74) in 1,4-dioxane (0.3 mL). Benzylchloroformate (5.9 µL, 0.042 mmol) was added then the mixture stirred for 2 hours. Water (5 mL) was added and the product extracted into dichloromethane (2×5 mL). The organic layer was washed with brine (5 mL), then dried (Na$_2$SO$_4$), filtered and reduced in vacuo to leave a residue (10.6 mg). Flash chromatography over silica, eluting with ethyl acetate:heptane mixtures 20:80 to 50:50 gave bicyclic alcohol (34b) (6.6 mg, 54%) as a white solid. TLC (R$_f$=0.20, EtOAc:heptane 1:1), analytical HPLC single main peak, R$_t$=17.32 min., HPLC-MS 434.1 [M+H]$^+$, 889.2 [2M+Na]$^+$; [α]$_D^{20}$–25.7° (c=2.53, CHCl$_3$); δ$_H$ (500 MHz, CDCl$_3$) mixture of rotamers major: minor 2:1; 2.01 (0.33H, brs, OH minor), 2.43 (3H, s, aryl-CH$_3$), 2.77 (0.66H, brs, OH major), 3.18-3.24 (0.33H, m, CbzNCH$_2$ minor), 3.33-3.38 (0.66H, m, CbzNCH$_2$ major), 3.79-3.85 (1H, m, OCH$_2$CHOH), 3.86-3.91 (1H, m, CbzNCH$_2$), 3.92-3.96 (0.33H, m, OCH$_2$CHOH minor), 3.96-4.01 (0.66H, m, OCH$_2$CHOH major), 4.13-4.16 (1H, m, CbzNCH), 4.35 (0.33H, m, OCH$_2$CHOH minor), 4.45 (0.66H, m, OCH$_2$CHOH major), 4.56 (0.33H, t, J=4.64 Hz, TsOCHCH, minor), 4.64 (0.66H, t, J=4.36 Hz, TsOCHCH, major), 4.71-4.78 (1H, m, TsOCHCH), 5.06-5.17 (2H, m, CH$_2$Ph), 7.31-7.38 (7H, m, phenyl CH and aromatic CH$_3$CCH), 7.80 (2H, d, J=8.33 Hz, aromatic OSO$_2$CCH); δ$_C$ (125 MHz, CDCl$_3$) 21.683 (aryl-CH$_3$), 47.384/47.855 (CbzNCH$_2$), 67.636/67.717 (CH$_2$Ph), 68.042/68.817 (CbzNCH), 75.525/75.967 (OCH$_2$CHOH), 75.967/76.836 (OCH$_2$CHOH), 76.068/76.401 (TsOCHCH), 79.342/80.208 (TsOCHCH), 127.965, 128.107, 128.382, 128.510, 128.605, 128.753, 129.940 and 129.997 (aromatic CH), 132.991 (CHOSO$_2$C quaternary), 135.779/135.869 (Cbz quaternary), 145.319 (CH$_3$C quaternary), 153.862/154.751 (Cbz C=O).

Preparation of (3aS,6S,6aS)-(9H-Fluoren-9-yl)methyl 6-chloro-3-oxotetrahydro-2H-furo[3,2-b]pyrrole-4(5H)-carboxylate (71). Following Scheme 17

(i) Preparation of (3R,3aR,6S,6aS)—Benzyl 6-chloro-3-hydroxytetrahydro-2H-furo[3,2-b]pyrrole-4(5H)-carboxylate (68).

Scheme 17. (a) LiCl, DMF, 130° C.; (b) Pd—C, H₂, ethanol; (c) Fmoc-Cl, Na₂CO₃, dioxane, H₂O; (d) Dess-Martin periodinane, anhydrous DCM; (e) LiCl, DMF, 130° C; fb) Cbz-Cl, Na₂CO₃, dioxane, H₂O.

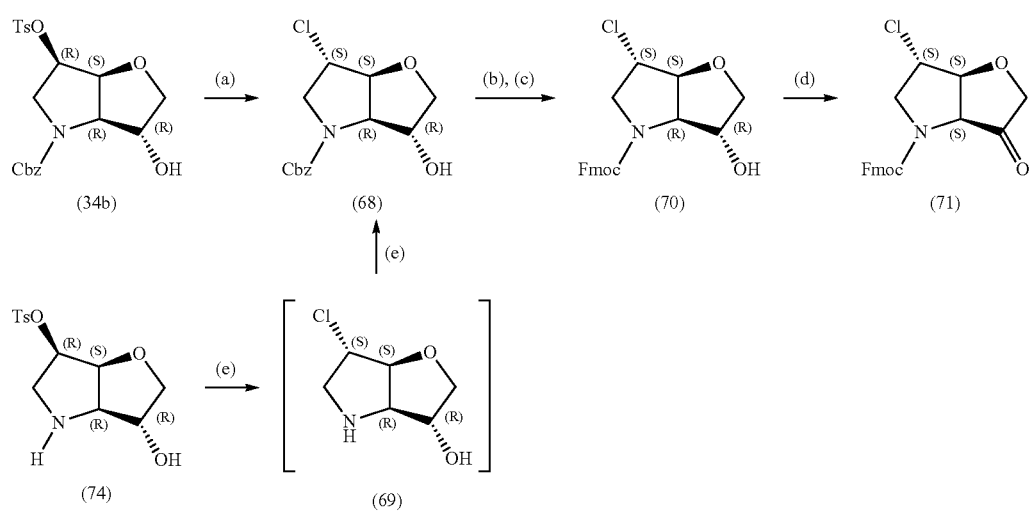

Lithium chloride (2.38 g, 56.2 mmol) was added to a stirred solution of (3R,3aR,6R, 6aS)-benzyl 3-hydroxy-6-(tosyloxy) tetrahydro-2H-furo[3,2-b]pyrrole-4(5H)-carboxylate (34b) (2.435 g, 5.62 mmol) in dimethylformamide (75 mL) under an atmosphere of argon. The mixture was heated at 130° C. for 7 hours then allowed to cool to ambient temperature. The mixture was diluted with dichloromethane (100 mL), then water (50 mL) was added and the mixture filtered through celite (filter cake washed with dichloromethane). The filtrate was separated then the organic phase washed with water (2×50 mL), then dried (Na₂SO₄), filtered and reduced in vacuo to leave a residue (1.54 g). Flash chromatography over silica, eluting with ethyl acetate:heptane mixtures 20:80 to 60:40 gave alcohol (68) (1.28 g, 77%) as an orange-brown solid. TLC (R$_f$=0.40, EtOAc:heptane 2:1), analytical HPLC single main peak, R$_t$=11.47 min., HPLC-MS 298.1/300.1 [M+H]⁺, 617.1 [2M+Na]⁺; [α]$_D^{23.0}$ −72.8° (c=2.61, CHCl₃); δ$_H$ (500 MHz, CDCl₃) mixture of rotamers major:minor 2:1; 1.78 and 2.24 (approx. 1H total, each brs, OH), 3.58-3.63 (1H, m, 1×CbzNCH₂), 3.83-3.88 (2H, m, OCH₂CHOH), 3.91 (0.66H, d, J=13.08 Hz, 1×CbzNCH₂, major), 4.02 (0.33H, J=13.09 Hz, 1×CbzNCH₂, minor), 4.24-4.26 (1H, m, CHCl), 4.39-4.42 (0.66H, m, CbzNCH minor and OCH₂CHOH minor), 4.43 (0.66H, d, J=4.33 Hz, CbzNCH major), 4.52 (0.66H, brs, OCH₂CHOH major), 4.72-4.75 (1H, m, CHCHCl), 5.11-5.16 (1.66H, m, 2×CH₂Ph major and 1×CH₂Ph minor), 5.24 (0.33H, d, J=12.29 Hz 1×CH₂Ph minor), 7.29-7.37 (5H, m, phenyl CH); δ$_C$ (125 MHz, CDCl₃) 53.57/53.74 (CbzNCH₂), 57.91/58.38 (CHCl), 67.53/67.58 (CH₂Ph), 67.69/68.64 (CbzNCH), 75.06/75.93 (OCH₂CHOH), 75.12/75.18 (OCH₂CHOH), 86.66/87.59 (CHCHCl), 127.85, 127.90, 128.24, 128.32, 128.56 and 128.69 (aromatic CH), 135.97/136.15 (Cbz quaternary), 154.41/154.96 (Cbz C=O).

(ii) (3R,3aR,6S,6aS)-(9H-Fluoren-9-yl)methyl 6-chloro-3-hydroxytetrahydro-2H-furo[3,2-b]pyrrole-4(5H)-carboxylate (70). Ethanol (8.5 mL) was added dropwise to a mixture of 10% palladium on charcoal (55 mg) and alcohol (68) (550 mg, 1.85 mmol) under an atmosphere of argon. The argon was replaced by hydrogen then the suspension was stirred for 1 hour 35 minutes before filtering the mixture through celite in vacuo. The filter cake was washed with ethanol (45 mL) then the solvents removed in vacuo from the filtrate. The residue was azeotroped with toluene (3×5 mL) to obtain (3R,3aR,6S,6aS)-6-chlorohexahydro-2H-furo[3,2-b]pyrrol-3-ol (69) which was used without further purification.

A solution of sodium carbonate (0.49 g, 4.63 mmol) in water (7.5 mL) followed by a solution of 9-fluorenyl-methoxycarbonyl chloride (0.55 g, 2.13 mmol) in 1,4-dioxane (2.5 mL) was added dropwise over 15 minutes whilst stirring to a solution of aminoalcohol (69) in 1,4-dioxane (5 mL). The mixture was stirred for 60 minutes then water (50 mL) was added and the product extracted into dichloromethane (3×25 mL), then dried (Na₂SO₄), filtered and reduced in vacuo to leave a colourless oil. Flash chromatography over silica, eluting with ethyl acetate:heptane mixtures 10:90 to 45:55 gave alcohol (70) (623 mg, 87%) as a white solid. TLC (R$_f$=0.45, EtOAc:heptane 1:1), analytical HPLC single main peak, R$_t$=16.54 min., HPLC-MS 386.1/388.1 [M+H]⁺, 408.1/410.1 [M+Na]⁺; [α]$_D^{27.5}$ −51.9° (c=2.31, CHCl₃); (proton complex) δ$_C$ (125 MHz, CDCl₃) 47.21/47.41 (Fmoc CH), 53.30/53.43 (FmocNCH₂), 57.74/58.36 (CHCl), 66.04/67.42 (Fmoc CH₂), 67.87/68.52 (FmocNCH), 74.81/75.09 (OCH₂CHOH), 74.92/75.51 (OCH₂CHOH), 86.57/87.24 (CHCHCl), 119.80/119.82/120.00/120.64/124.55/124.63/124.90/127.04/127.08/127.40/127.51/127.78/127.80/127.87 and 127.91 (aromatic CH), 141.21/141.29/141.38/143.44/143.70/143.88 and 143.91 (aromatic quaternary), 154.13/154.79 (Fmoc C=O).

(iii) (3aS,6S,6aS)-(9H-Fluoren-9-yl)methyl 6-chloro-3-oxotetrahydro-2H-furo[3,2-b]pyrrole-4(5H)-carboxylate (71). Dess-Martin periodinane (1.32 g, 3.11 mmol) was added to a stirred solution of alcohol (70) (600 mg, 1.56 mmol) in dichloromethane (15 mL) under an atmosphere of argon. The mixture was stirred for 19 hours then diluted with dichloromethane (50 mL) then washed with a mixture of saturated aqueous sodium bicarbonate and 0.25M sodium thiosulphate solution (1:1, 30 mL), saturated aqueous sodium bicarbonate (25 mL), brine (25 mL), then dried (Na₂SO₄), filtered and reduced in vacuo to obtain a white solid (935 mg). Flash chromatography over silica, eluting with ethyl acetate: heptane mixtures 15:85 to 100:0 gave ketone (71) (506 mg, 85%) as a white solid contaminated with 2-iodosylbenzoic acid (<5%). TLC (R$_f$=0.35, EtOAc:heptane 1:1), analytical HPLC single main peak, R$_t$=15.81 min., HPLC-MS 384.1/386.1 [M+H]$^+$, 406.1/408.1 [M+Na]$^+$, 424.1/426.1 [M+H$_2$O+Na]$^+$, 789.1/791.2 [2M+Na]; [α]$_D^{25.5}$–144.6° (c=2.18, CHCl$_3$); δ$_H$ (500 MHz, CDCl$_3$) mixture of rotamers major:minor 0.55:0.45; 3.75-3.89 (1H, m, 1×FmocNCH$_2$), 3.93-4.03 (1.55H, m, 1×OCH$_2$C=O and 1×FmocNCH$_2$ major), 4.12-4.22 (1.45H, m, 1×OCH$_2$C=O and 1×FmocNCH$_2$ minor), 4.25 (0.55H, brt, J=6.72 Hz, Fmoc CH major), 4.30-4.44 (2.45H, m, CHCl, 1×FmocNCH$_2$ and Fmoc CH minor), 4.45 (0.45H, d, J=4.46 Hz, FmocNCH minor), 4.50-4.58 (1.55H, m, 1×Fmoc CH$_2$ and FmocNCH major), 4.85 (0.55H, d, J=4.44 Hz, CHCHCl major), 4.90 (0.45H, d, J=4.41 Hz, CHCHCl minor), 7.27-7.76 (8H, aromatic CH); δ$_C$ (125 MHz, CDCl$_3$) 47.09/47.13 (Fmoc CH), 53.43/53.66 (FmocNCH$_2$), 57.60/58.09 (CHCl), 60.47/60.87 (FmocNCH), 67.86/68.56 (Fmoc CH$_2$), 70.75 (OCH$_2$C=O), 86.32/87.32 (CHCHCl), 119.93/119.99/120.08/124.87/124.94/125.17/125.36/127.09/127.71 and 127.74 (aromatic CH), 141.28/141.32/143.51/143.63 and 144.16 (aromatic quaternary), 154.88/154.94 (Fmoc C=O), 206.45/206.64 (OCH$_2$C=O).

Alternative preparation of (3R,3aR,6S,6aS)—Benzyl 6-chloro-3-hydroxytetrahydro-2H-furo[3,2-b]pyrrole-4 (5H)-carboxylate (68). Lithium chloride (142 mg, 3.34 mmol) was added to a stirred solution of (3R,3aR,6R,6aS) 3-hydroxyhexahydro-2H-furo[3,2-b]pyrrol-6-yl 4-methylbenzenesulfonate (74) (100 mg, 0.33 mmol) in dimethylformamide (3 mL) under an atmosphere of argon. The mixture was heated at 130° C. for 2.75 hours then allowed to cool to ambient temperature to give a solution containing 6-chloroaminoalcohol (69). A solution of sodium carbonate (89 mg, 0.84 mmol) in water (1.5 mL) was added followed by benzylchloroformate (0.105 mL, 0.74 mmol). The mixture was stirred for 35 minutes then dichloromethane (10 mL) and water (15 mL) added. The organic phase was separated and the aqueous extracted with dichloromethane (2×5 mL). The combined organic phase was washed with brine (5 mL), then dried (Na$_2$SO$_4$), filtered and reduced in vacuo to leave a black residue (97 mg). Flash chromatography over silica, eluting with ethyl acetate:heptane mixtures 5:95 to 50:50 gave 6-chloroalcohol (68) (48 mg, 48%) as a pale yellow oil. TLC (R$_f$=0.30, EtOAc:heptane 3:2), analytical HPLC single main peak, R$_t$=11.47 min., HPLC-MS 298.0/300.0 [M+H]$^+$, 617.1/619.1 [2M+Na]$^+$; [α]$_D^{22}$–76.9° (c=4.81, CHCl$_3$).

Solid Phase Chemistry

Fmoc-ketone building block (71) may be utilised in a solid phase synthesis of EXAMPLE inhibitors (1-39) of general formula I. The methods used were directly analogous to those described in detail in WO02057270, utilising the 4-{[(Hydrazinocarbonyl)amino]methyl}cyclohexane carboxylic acid trifluoroacetate based linker, solid phase lanterns (ex Mimotopes), standard Fmoc chemistries and acidolytic cleavage followed by semi-preparative HPLC purification (see WO02057270 pg 124-127 for full generic details). Novel compounds (1-5) or prior art compound (38) are detailed for comparison and can readily be prepared by the general methods detailed in WO02057270 or WO0807127 through use of appropriate Fmoc-ketone building blocks (e.g. 6-unsubstituted bicycle (WO02057270), compound 19, pg 134; 6(S)-fluoro bicycle (WO0807127, compound 63, pg 88); 6(S)-chloro bicycle (WO0807127, compound 71, pg 94); 6(R)-chloro bicycle (WO0807127, compound 79, pg 98)). Fmoc-ketone building blocks are then derivatised as appropriate with a R$^9$—COOH carboxylic acid via standard uronium activation techniques.

Example 1

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide

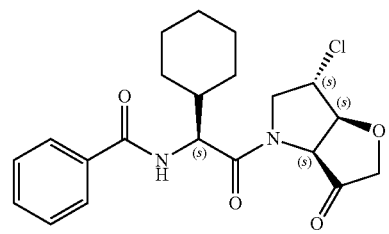

HPLC-MS R$_t$=2.82 min, 405.1/407.1 [M+H]$^+$, 423.2/425.2 [M+H+18]$^+$.

Example 2

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-tetrazol-1-yl)benzamide

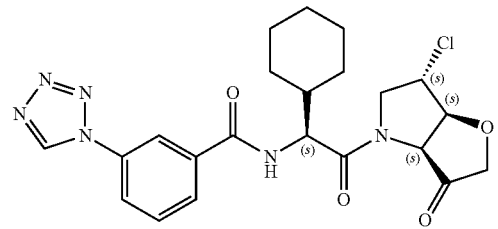

HPLC-MS R$_t$=2.65 min, 473.2/475.2 [M+H]$^+$, 491.2/493.2 [M+H+18]$^+$.

Example 3

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-imidazol-1-yl)benzamide

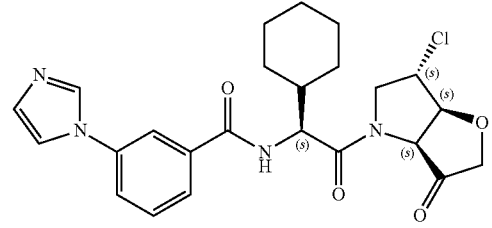

HPLC-MS R$_t$=2.37 min, 471.2/473.2 [M+H]$^+$, 489.2/491.2 [M+H+18]$^+$.

Example 4

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-imidazol-1-yl)benzamide

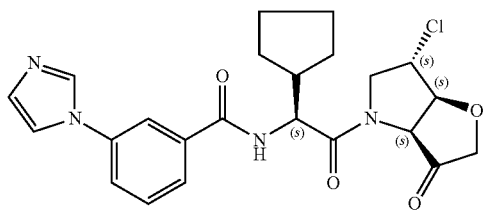

HPLC-MS R$_t$=2.12 min, 457.1/459.1 [M+H]$^+$, 475.2/477.2 [M+H+18]$^+$.

Example 5

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide

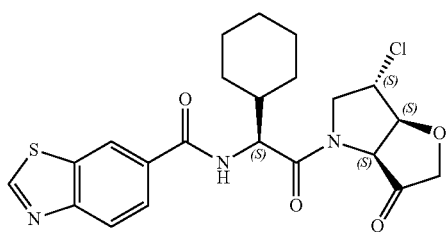

HPLC-MS R$_t$=2.68 min, 462.1/464.1 [M+H]$^+$, 480.1/482.1 [M+H+18]$^+$.

Example 6

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(5,6-dihydroimidazo[2,1-b]thiazol-3-yl)benzamide

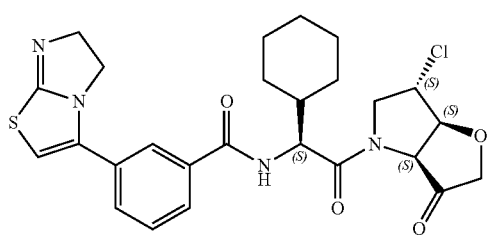

HPLC-MS R$_t$=2.49 min, 529.2/531.2 [M+H]$^+$, 547.2/549.2 [M+H+18]$^+$.

Example 7

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-pyrazol-4-yl)benzamide

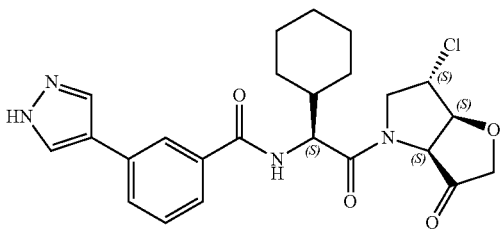

HPLC-MS R$_t$=2.75 min, 457.2/459.2 [M+H]$^+$, 475.2/477.2 [M+H+18]$^+$.

Example 8

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-benzo[d][1,2,3]triazole-6-carboxamide

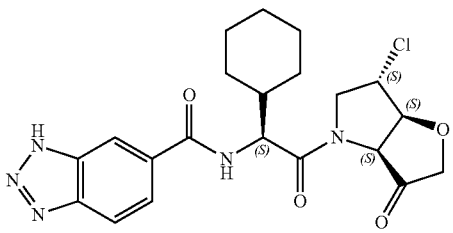

HPLC-MS R$_t$=2.72 min, 446.2/448.2 [M+H]$^+$, 464.2/466.2 [M+H+18]$^+$.

Example 9

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-benzo[d][1,2,3]triazole-6-carboxamide

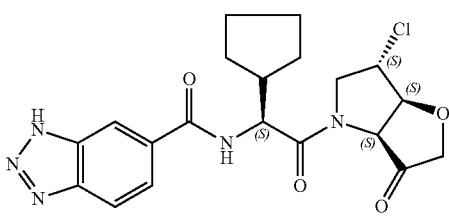

HPLC-MS R$_t$=2.48 min, 432.1/434.1 [M+H]$^+$, 450.1/452.1 [M+H+18]$^+$.

Example 10

2-Amino-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide

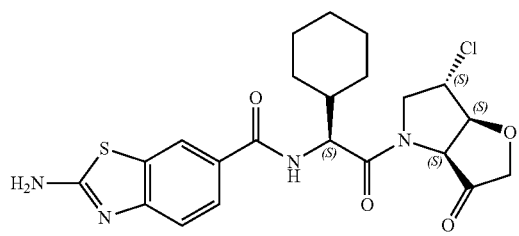

HPLC-MS R$_t$=2.10 min, 477.2/479.2 [M+H]$^+$, 495.2/497.2 [M+H+18]$^+$.

Example 11

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)oxazole-5-carboxamide

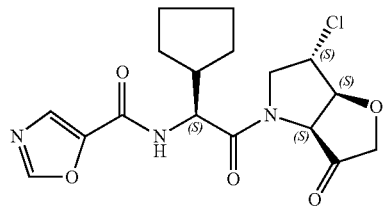

HPLC-MS R$_t$=2.29 min, 382.1/384.1 [M+H]$^+$, 400.1/402.1 [M+H+18]$^+$.

Example 12

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indazole-6-carboxamide

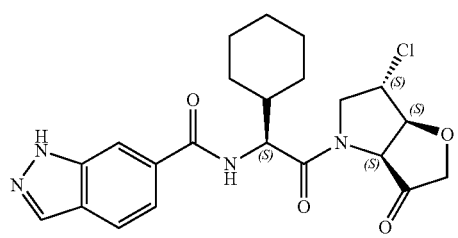

HPLC-MS R$_t$=2.16 min, 445.2/447.2 [M+H]$^+$, 463.2/465.2 [M+H+18]$^+$.

Example 13

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-pyrazol-4-yl)benzamide

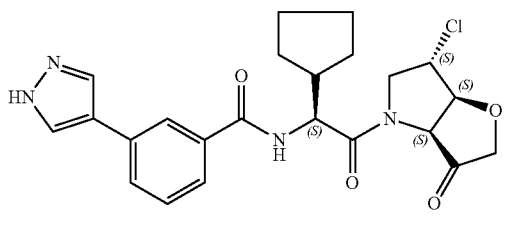

HPLC-MS R$_t$=2.47 min, 457.2/459.2 [M+H]$^+$, 475.2/477.2 [M+H+18]$^+$.

Example 14

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)nicotinamide

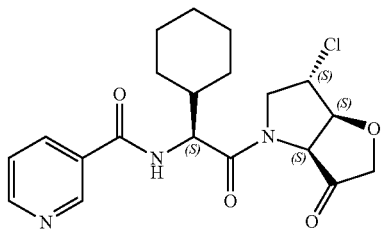

HPLC-MS R$_t$=2.19 min, 406.1/408.1 [M+H]$^+$, 424.2/426.2 [M+H+18]$^+$.

Example 15

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)isonicotinamide

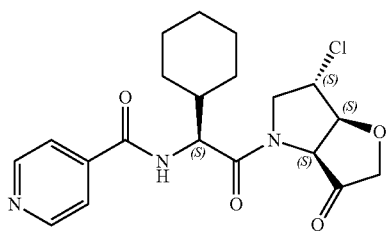

HPLC-MS R$_t$=2.15 min, 406.2/408.1 [M+H]$^+$, 424.2/426.2 [M+H+18]$^+$.

Example 16

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-fluorobenzamide

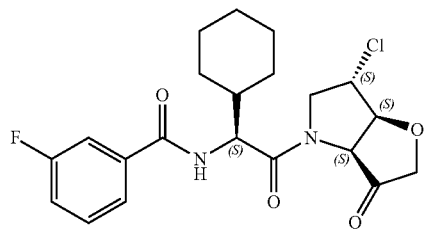

HPLC-MS $R_t$=2.96 min, 423.2/425.2 [M+H]$^+$, 441.2/443.2 [M+H+18]$^+$.

Example 17

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(pyridin-3-yl)benzamide

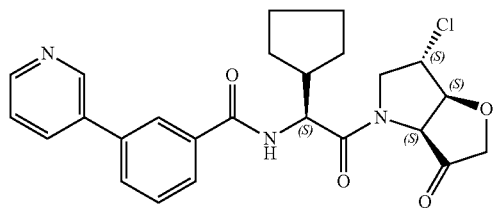

HPLC-MS $R_t$=2.26 min, 468.2/470.2 [M+H]$^+$, 486.2/488.2 [M+H+18]$^+$.

Example 18

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2,3-dioxo-1,2,3,4-tetrahydroquinoxaline-6-carboxamide

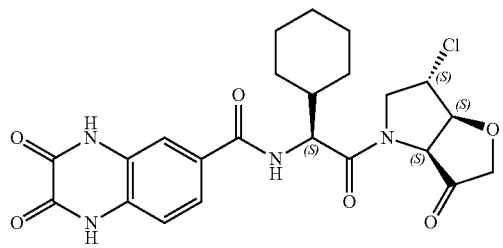

HPLC-MS $R_t$=2.16 min, 489.2/491.2 [M+H]$^+$, 507.2/509.2 [M+H+18]$^+$.

Example 19

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide

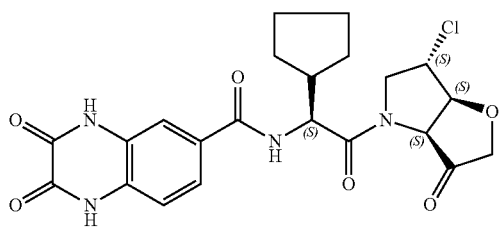

HPLC-MS $R_t$=1.97 min, 475.2/477.2 [M+H]$^+$, 493.2/495.2 [M+H+18]$^+$.

Example 20

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-1,2,3,4-tetrahydroquinoline-6-carboxamide

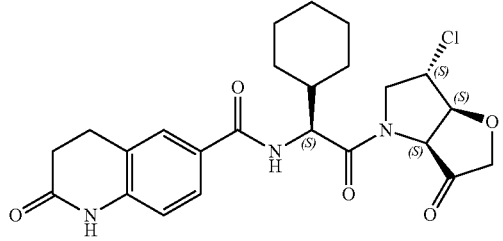

HPLC-MS $R_t$=2.04 min, 474.2/476.2 [M+H]$^+$, 492.2/494.2 [M+H+18]$^+$.

Example 21

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide

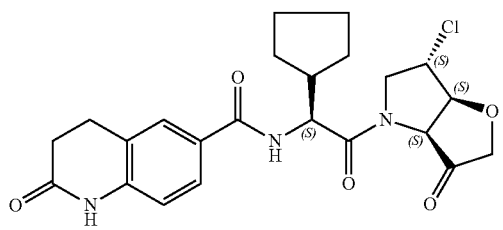

HPLC-MS $R_t$=1.84 min, 460.2/462.2 [M+H]$^+$, 478.2/480.2 [M+H+18]$^+$.

Example 22

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-5-carboxamide

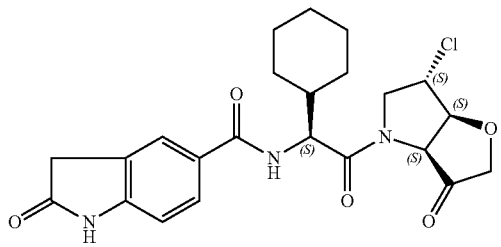

HPLC-MS R$_t$=1.93 min, 460.2/462.2 [M+H]$^+$, 478.2/480.2 [M+H+18]$^+$.

Example 23

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-5-carboxamide

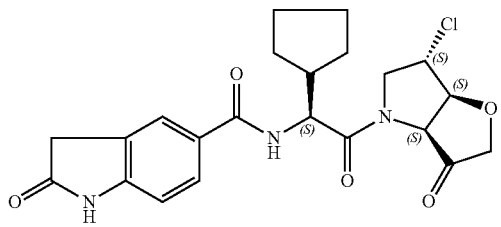

HPLC-MS R$_t$=1.58 min, 446.2/448.2 [M+H]$^+$, 464.2/466.2 [M+H+18]$^+$.

Example 24

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-6-carboxamide

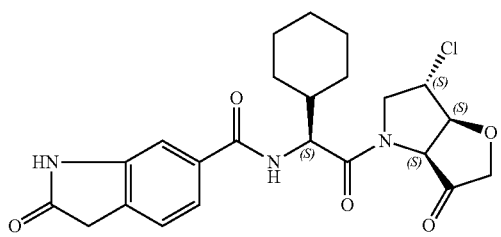

HPLC-MS R$_t$=1.98 min, 460.2/462.2 [M+H]$^+$, 478.2/480.2 [M+H+18]$^+$.

Example 25

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-6-carboxamide

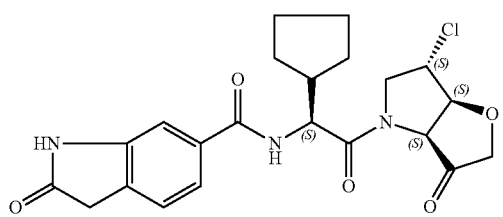

HPLC-MS R$_t$=1.65 min, 446.2/448.2 [M+H]$^+$, 464.2/466.2 [M+H+18]$^+$.

Example 26

4-Acetamido-N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide

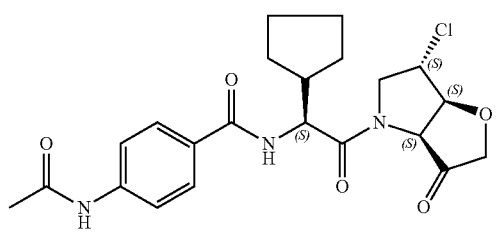

HPLC-MS R$_t$=1.92 min, 448.2/450.2 [M+H]$^+$, 466.2/468.2 [M+H+18]$^+$.

Example 27

4-Acetamido-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide

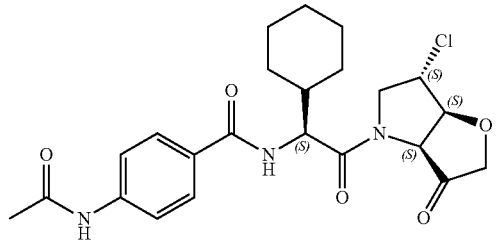

HPLC-MS R$_t$=2.05 min, 462.2/464.2 [M+H]$^+$, 480.2/482.2 [M+H+18]$^+$.

Example 28

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(cyclopropanecarboxamido) benzamide

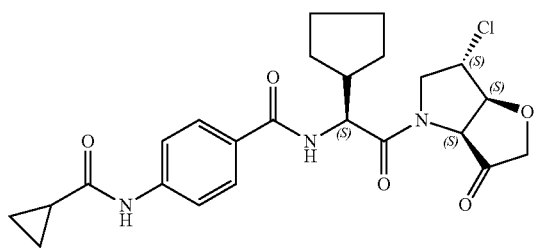

HPLC-MS $R_t$=2.20 min, 474.2/476.2 [M+H]$^+$, 492.2/494.2 [M+H+18]$^+$.

Example 29

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(cyclopropanecarboxamido) benzamide

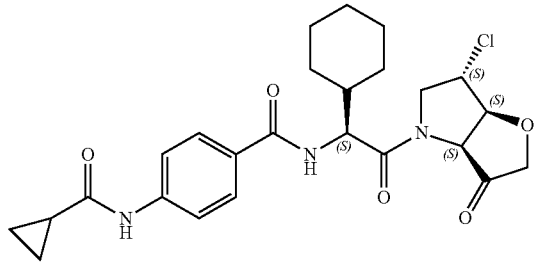

HPLC-MS $R_t$=2.35 min, 488.3/490.3 [M+H]$^+$, 506.3/508.3 [M+H+18]$^+$.

Example 30

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(methylsulfonamido)benzamide

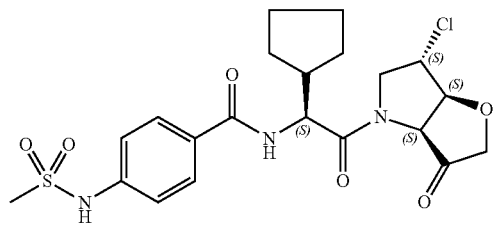

HPLC-MS $R_t$=2.01 min, 484.1/486.1 [M+H]$^+$, 505.2/504.2 [M+H+18]$^+$.

Example 31

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(methylsulfonamido)benzamide

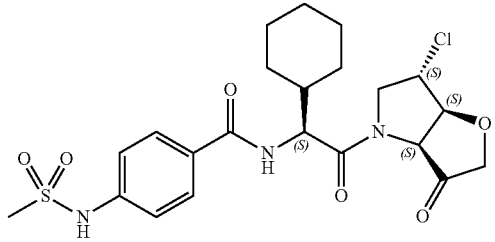

HPLC-MS $R_t$=2.20 min, 498.2/500.2 [M+H]$^+$, 516.2/518.2 [M+H+18]$^+$.

Example 32

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydro-1H-benzo[d]imidazole-5-carboxamide

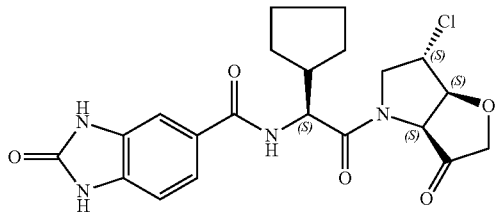

HPLC-MS $R_t$=1.83 min, 447.1/449.1 [M+H]$^+$, 465.2/467.2 [M+H+18]$^+$.

Example 33

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydro-1H-benzo[d]imidazole-5-carboxamide

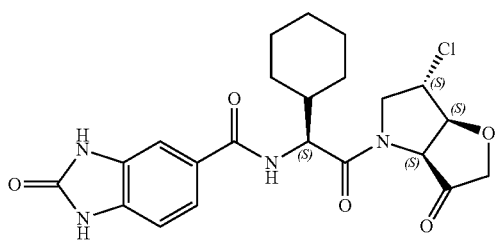

HPLC-MS $R_t$=1.94 min, 461.2/463.2 [M+H]$^+$, 479.2/481.2 [M+H+18]$^+$.

Example 34

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydrobenzo[d]thiazole-6-carboxamide

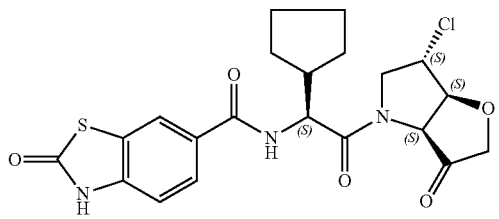

HPLC-MS $R_t$=2.03 min, 464.1/466.1 [M+H]$^+$, 482.2/484.2 [M+H+18]$^+$.

Example 35

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydrobenzo[d]thiazole-6-carboxamide

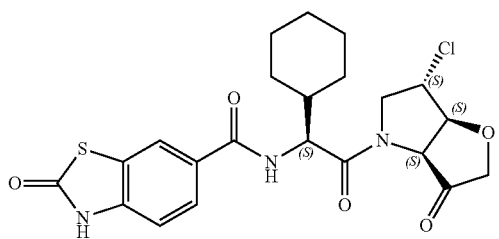

HPLC-MS $R_t$=2.22 min, 478.1/480.1 [M+H]$^+$, 496.2/498.2 [M+H+18]$^+$.

Example 36

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3,4,5-tetrahydro-1H-benzo[b]azepine-7-carboxamide

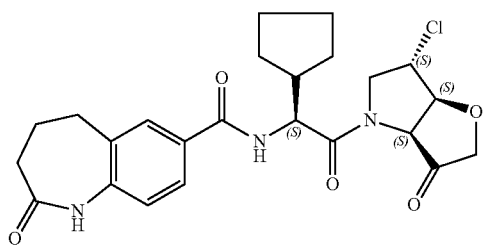

HPLC-MS $R_t$=1.99 min, 474.2/476.2 [M+H]$^+$, 492.2/494.2 [M+H+18]$^+$.

Example 37

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3,4,5-tetrahydro-1H-benzo[b]azepine-7-carboxamide

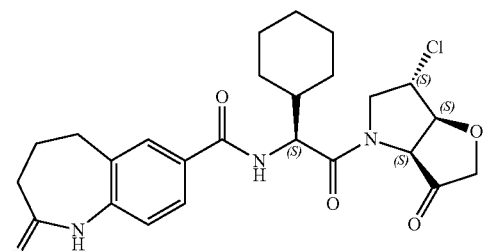

HPLC-MS $R_t$=2.13 min, 488.2/490.2 [M+H]$^+$, 506.2/508.2 [M+H+18]$^+$.

Example 38

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-oxo-3,4-dihydro-2H-benzo[b][1,4]oxazine-7-carboxamide

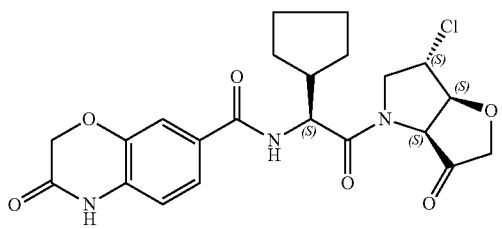

HPLC-MS $R_t$=1.90 min, 462.2/464.2 [M+H]$^+$, 480.2/482.2 [M+H+18]$^+$.

Example 39

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-oxo-3,4-dihydro-2H-benzo[b][1,4]oxazine-7-carboxamide

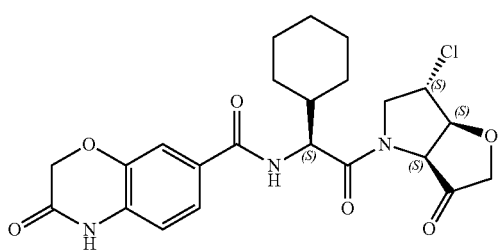

HPLC-MS $R_t$=2.08 min, 476.2/478.2 [M+H]$^+$, 494.2/496.2 [M+H+18]$^+$.

Solution Phase Syntheses

Alternatively, EXAMPLES of the invention may be prepared by traditional solution phase organic chemistry techniques for example from building block (69) (3R,3aR,6S,6aS)-6-chlorohexahydro-2H-furo[3,2-b]pyrrol-3-ol (e.g. following the general methods detailed in WO08007127, pg 103-107).

Formation of EXAMPLE .Hydrochloride Salt.

EXAMPLE ketone (free base) (1 mmol) was dissolved in acetonitrile (16.7 mL) and standardised 0.1N HCl (1.3 eq, 13.0 mL) was added. The mixture was frozen and lyophilised to leave the EXAMPLE .hydrochloride salt as a solid.

Example A

Assays for Cysteine Protease Activity

The compounds of this invention may be tested in one of a number of literature based biochemical assays that are designed to elucidate the characteristics of compound inhibition. The data from these types of assays enables compound potency and the rates of reaction to be measured and quantified. This information, either alone or in combination with other information, would allow the amount of compound required to produce a given pharmacological effect to be determined.

In Vitro Cathepsin Ki Inhibition Measurements

Stock solutions of substrate or inhibitor were made up to 10 mM in 100% dimethylsulfoxide (DMSO) (Rathburns, Glasgow, U.K.) and diluted as appropriately required. In all cases the DMSO concentration in the assays was maintained at less than 1% (vol./vol.). The equilibrium inhibition constants ($K_i^{ss}$) for each compound were measured under steady-state conditions monitoring enzyme activity as a function of inhibitor concentration. The values were calculated on the assumption of pure competitive behaviour (Cornish-Bowden, A. *Fundamentals of enzyme kinetics* Portland Press; 1995, 93-128).

Human recombinant cathepsin K (0.25 nM final; B. Turk, Josef, Stefan Institute, Ljubljana, Slovenia), was routinely assayed in 100 mM sodium acetate; pH 5.5 containing 1 mM EDTA, 10 mM L-cysteine and 1.8 µM Z-Leu-Arg-AMC ([S]= $K_M$).

Human recombinant cathepsin S (0.25 nM final, Merck, *E. coli* cat #219343) was routinely assayed in 10 mM Bis Tris Propane; pH 6.5 containing 1 mM EDTA, 5 mM β mercaptoethanol, 1 mM CaCl$_2$ and 45 µM Boc-Val-leu-Lys-AMC ([S]=$K_M$) (Sigma Chemical Company, Poole, U.K.).

Human liver cathepsin B (0.25 nM final; Merck Biosciences), was routinely assayed in 10 mM bis-tris propane; pH 6.5 containing 1 mM EDTA, 5 mM 2-mercaptoethanol, 1 mM CaCl$_2$ and 60 µM Z-Phe-Arg-AMC ([S]=$K_M$) (Bachem, Weil am Rhein, Germany).

Human recombinant cathepsin V (0.25 nM final, Merck Biosciences) was routinely assayed in 100 mM sodium acetate; pH 5.5 containing 10 mM L-cysteine, 0.001% (vol./vol.) zwittergent 3-12 (Merck Biosciences) and 5 µM Z-Leu-Arg-AMC ($K_M$=0.5 µM) (Amura).

Human liver cathepsin L (0.25 nM final, Athens Research and Technology, GA, USA) was routinely assayed in 10 mM bis-tris propane; pH 6.5 containing 1 mM EDTA, 5 mM 2-mercaptoethanol, 1 mM CaCl$_2$ and 4 µM Ac-Phe-Arg-AMC ([S]=$K_M$) (Bachem).

Measurement of the Apparent Macroscopic Binding (Michaelis) Constants ($K_M^{app}$) for Substrates The apparent macroscopic binding constant ($K_M^{app}$) for each substrate was calculated, from the dependence of enzyme activity as a function of substrate concentration. The observed rates were plotted on the ordinate against the related substrate concentration on the abscissa and the data fitted by direct regression analysis (Prism v 3.02; GraphPad, San Diego, USA) using Equation 1 (Cornish-Bowden, A. *Fundamentals of enzyme kinetics* Portland Press; 1995, 93-128).

$$v_i = \frac{V_{max}^{app} \cdot [S_o]}{[S_o] + K_M^{app}} \quad (1)$$

In Equation 1 '$v_i$' is the observed initial rate, '$V_{max}^{app}$' is the observed maximum activity at saturating substrate concentration, '$K_M^{app}$' is the apparent macroscopic binding (Michaelis) constant for the substrate, '$[S_o]$' is the initial substrate concentration.

Measurement of the Inhibition Constants

The apparent inhibition constant ($K_i$) for each compound was determined on the basis that inhibition was reversible and occurred by a pure-competitive mechanism. The $K_i$ values were calculated, from the dependence of enzyme activity as a function of inhibitor concentration, by direct regression analysis (Prism v 3.02) using Equation 2 (Cornish-Bowden, A., 1995).

$$v_i = \frac{V_{max}^{app} \cdot [S]}{[S] + \{K_M^{app} \cdot ([I]/K_i)\}} \quad (2)$$

In Equation 2 '$v_i$' is the observed residual activity, '$V_{max}^{app}$' is the observed maximum activity (i.e. in the absence of inhibitor), '$K_M^{app}$' is the apparent macroscopic binding (Michaelis) constant for the substrate, '[S]' is the initial substrate concentration, '$K_i$' is the apparent dissociation constant and '[I]' is the inhibitor concentration. In situations where the apparent dissociation constant ($K_i^{app}$) approached the enzyme concentrations, the $K_i^{app}$ values were calculated using a quadratic solution in the form described by Equation 3 (Morrison, J. F. *Trends Biochem. Sci.,* 7, 102-105, 1982; Morrison, J. F. *Biochim. Biophys. Acta,* 185, 269-286, 1969; Stone, S. R. and Hofsteenge, *J. Biochemistry,* 25, 4622-4628, 1986).

$$v_i = \frac{F\left\{E_o - I_o - K_i^{app} + \sqrt{(E_o - I_o - K_i^{app})^2 + 4 \cdot K_i^{app} \cdot E_o}\right\}}{2} \quad (3)$$

$$K_i^{app} = K_i(1 + [S_o]/K_M^{app}) \quad (4)$$

In Equation 3 '$v_i$' is the observed residual activity, 'F' is the difference between the maximum activity (i.e. in the absence of inhibitor) and minimum enzyme activity, '$E_o$' is the total enzyme concentration, '$K_i^{app}$' is the apparent dissociation constant and '$I_o$' is the inhibitor concentration. Curves were fitted by non-linear regression analysis (Prism) using a fixed value for the enzyme concentration. Equation 4 was used to account for the substrate kinetics, where '$K_i$' is the inhibition constant, '$[S_o]$' is the initial substrate concentration and '$K_M^{app}$' is the apparent macroscopic binding (Michaelis) constant for the substrate (Morrison, 1982).

The Second-Order Rate of Reaction of Inhibitor with Enzyme

Where applicable, the concentration dependence of the observed rate of reaction ($k_{obs}$) of each compound with enzyme was analysed by determining the rate of enzyme inactivation under pseudo-first order conditions in the presence of substrate (Morrison, J. F., *TIBS*, 102-105, 1982; Tian, W. X. and Tsou, C. L., *Biochemistry*, 21, 1028-1032, 1982; Morrison, J. F. and Walsh, C. T., from Meister (Ed.), *Advances in Enzymol.*, 61, 201-301, 1988; Tsou, C. L., from Meister (Ed.), *Advances in Enzymol.*, 61, 381-436, 1988). Assays were carried out by addition of various concentrations of inhibitor to assay buffer containing substrate. Assays were initiated by the addition of enzyme to the reaction mixture and the change in fluorescence monitored over time. During the course of the assay less than 10% of the substrate was consumed.

$$F = v_s t + \frac{(v_o - v_s)[1 - e^{(k_{obs} \cdot t)}]}{k_{obs}} + D \qquad (5)$$

The activity fluorescence progress curves were fitted by non-linear regression analysis (Prism) using Eq. 5 (Morrison, 1969; Morrison, 1982); where 'F' is the fluorescence response, 't' is time, '$v_o$' is the initial velocity, '$v_s$' is the equilibrium steady-state velocity, '$k_{obs}$' is the observed pseudo first-order rate constant and 'D' is the intercept at time zero (i.e. the ordinate displacement of the curve). The second order rate constant was obtained from the slope of the line of a plot of $k_{obs}$ versus the inhibitor concentration (i.e. $k_{obs}/[I]$). To correct for substrate kinetics, Eq. 6 was used, where '[$S_o$]' is the initial substrate concentration and '$K_M^{app}$' is the apparent macroscopic binding (Michaelis) constant for the substrate.

$$k_{inact} = \frac{k_{obs}(1 + [S_o]/K_M^{app})}{[I]} \qquad (6)$$

Compounds of the invention when tested by the above described assays exhibit cathepsin K inhibitory activity with an in vitro Ki inhibitory constant of less than or equal to 100 nM.

Liver Microsomal Incubations:

Human and rat liver microsomes were purchased from BD Gentest (Woburn, Mass., USA) and β-nicotinamide adenine dinucleotide 2'-phosphate reduced tetrasodium salt (NADPH) was purchased from Sigma-Aldrich (Poole, Dorset, UK). All liver microsome incubations were carried out in 50 mM potassium phosphate buffer at pH 7.4, with a final microsomal protein concentration of 0.5 mg/mL. Compounds were taken from 5 mM DMSO stock solutions and diluted in incubation buffer to give a final concentration of 25 µM, with a final DMSO concentration of 0.5% v/v. In brief, compounds were added to the incubation buffer along with the liver microsomes and incubated at 37° C. for 10 minutes. The reaction was then initiated by the addition of NADPH, previously dissolved in incubation buffer, to give a final concentration of 1 mM and re-incubated at 37° C. Aliquots were removed at 2 and 60 minutes and quenched with an equal volume of cold acetonitrile. After mixing vigorously, the precipitated protein matter was removed by filtration (Multiscreen Solvinert filter plates, Millipore, Bedford, Mass., USA) and the filtrate analysed by reverse phase HPLC with mass spectrometric detection, using single ion monitoring of the [M+H]$^+$ species. Metabolic turnover was determined by comparison of peak areas from the ion chromatograms of the parent compound at 2 and 60 minutes and expressed as percent remaining at 1 hour.

Plasma Incubations:

Human and rat plasma were purchased from Innovative Research Inc. (Southfield. MI, USA). Compounds were taken from 5 mM DMSO stock solutions and added to plasma, which had previously been incubated at 37° C., to give a final concentration of 25 µM and re-incubated. Aliquots were removed at 2 and 60 minutes and quenched with an equal volume of cold acetonitrile. After mixing vigorously, the precipitated protein matter was removed by filtration (Multiscreen Solvinert filter plates, Millipore, Bedford, Mass., USA) and the filtrate analysed by reverse phase HPLC with mass spectrometric detection, using single ion monitoring of the [M+H]$^+$ species. Metabolic turnover was determined by comparison of peak areas from the ion chromatograms of the parent compound at 2 and 60 minutes and expressed as percent remaining at 1 hour.

LogD Determinations:

LogD$_{(PBS)}$ determinations were performed in 96 well microtitre plates using a miniaturised "shake-flask" method. In brief, compounds were taken from 10 mM DMSO stock solutions and added to wells containing equal volumes of phosphate buffered saline (10 mM; pH 7.4) (PBS) and 1-octanol (Sigma-Aldrich, Poole, Dorset, UK) to give a final concentration of 50 µM. The plates were then capped and mixed vigorously for 1 hour on a microtitre plate shaker, after which they were left to stand, allowing the PBS and octanol phases to separate. The PBS layer was analysed by reverse phase HPLC with mass spectrometric detection, using single ion monitoring of the [M+H]$^+$ species. LogD$_{(PBS)}$ was determined by comparison of the peak area from the ion chromatogram of the compound in the PBS phase with that of a 50 µM standard of the same compound dissolved in acetonitrile/water (50:50) and calculated using the following formula:

$$\text{Log}D = \text{Log}\left[\frac{AUCstd - AUCpbs}{AUCpbs}\right]$$

Where AUCstd and AUCpbs are the peak areas from the standard and test ion chromatograms respectively. LogD$_{(PBS)}$ determinations were also made using PBS at pH 6.9 and 5.5 by adjusting the pH of the buffer prior to the start of the assay, with 0.1 M HCL.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Biological properties for EXAMPLE compounds, prior art compound (38)
(WO-A-02057270, pg 151) and novel Compounds 1-5.

| Compound | In vitro Ki (nM) vs Cath S | In vitro Ki (nM) vs Cath K |
|---|---|---|
| Prior art compound 38 (WO-A-02057270, pg 151) | 555 | >4000 |
| Compound 1; within (but not specifically exemplified) prior art (Quibell, M. et. al. WO02057270). | 225 | 305 |
| Compound 2; novel compound for comparison. | 59 | 95 |
| EXAMPLE 1 | 8.5 | 35 |
| Compound 3; within (but not specifically exemplified) prior art (Quibell, M. et. al. WO02057270). | 170 | 560 |

TABLE 1-continued
Biological properties for EXAMPLE compounds, prior art compound (38) (WO-A-02057270, pg 151) and novel Compounds 1- 5.
| Compound | In vitro Ki (nM) vs Cath S | In vitro Ki (nM) vs Cath K |
|---|---|---|
| 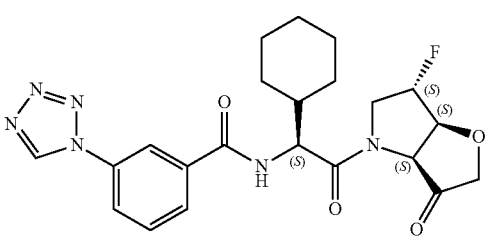 Compound 4; novel compound for comparison. | 50 | 340 |
| 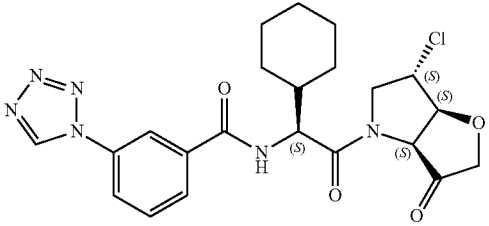 EXAMPLE 2 | 3.6 | 27 |
| 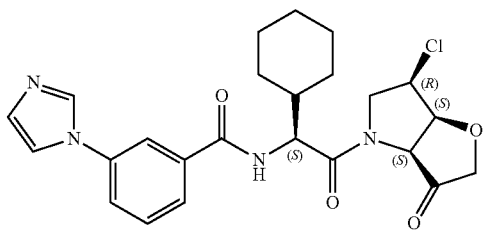 Compound 5; novel compound for comparison. | 32 | 230 |
| 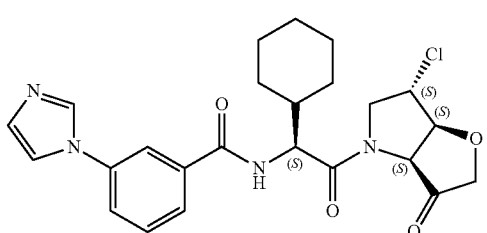 EXAMPLE 3 | 1.7 | 23 |
| 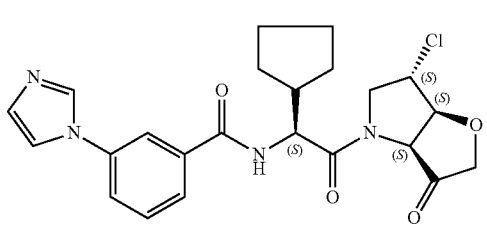 EXAMPLE 4 | 10.4 | 14.6 |

The invention claimed is:

1. A compound of formula (I), or a pharmaceutically acceptable salt, or hydrate thereof,

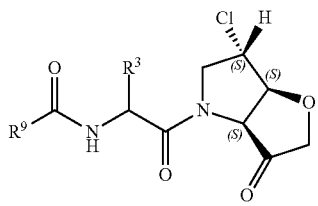

(I)

wherein:

$R^3$ is selected from cyclopentyl and cyclohexyl;
$R^9$ is selected from the following:

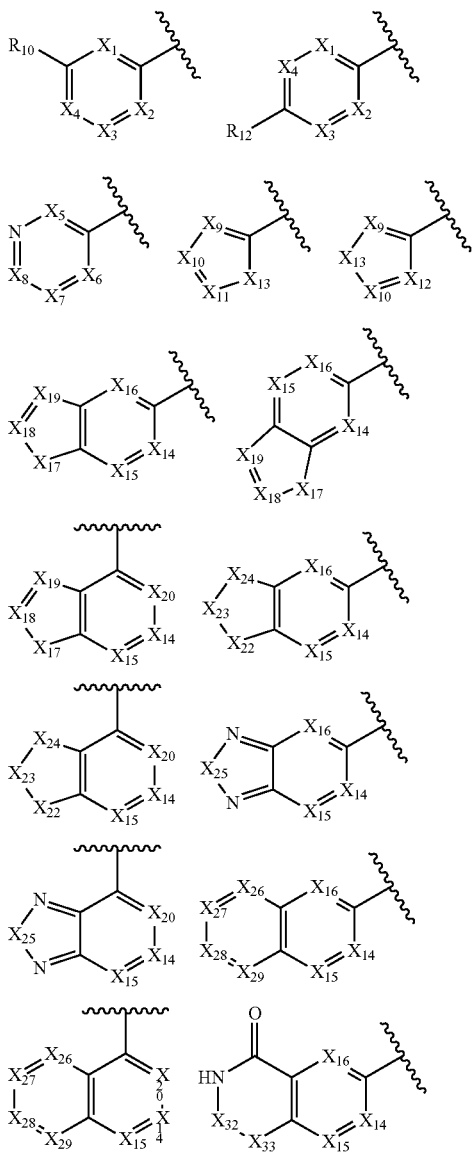

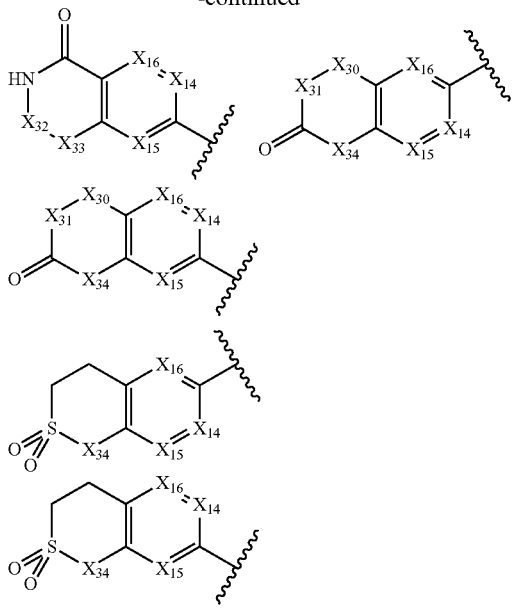

wherein:
$X_1$, $X_2$, $X_3$, $X_4$, $X_{14}$, $X_{15}$, $X_{16}$ and $X_{20}$ are each independently selected from:
  CH, C—($C_{1-6}$-alkyl), C—($C_{1-6}$-alkoxy), C-halo and N;
such that a maximum of two of $X_1$, $X_2$, $X_3$, $X_4$, $X_{14}$, $X_{15}$, $X_{16}$ and $X_{20}$ are selected from N, C-halo and C—($C_{1-6}$-alkoxy);
$X_5$, $X_6$, $X_7$ and $X_8$ are each independently selected from:
  CH, C—($C_{1-6}$-alkyl), C—($C_{1-6}$-alkoxy), C-halo, N and C—OH;
such that a maximum of one of $X_5$, $X_6$, $X_7$ and $X_8$ is N, C-halo, C—OH or C—($C_{1-6}$-alkoxy);
$X_9$ and $X_{12}$ are each independently selected from:
  CH, C—($C_{1-6}$-alkyl), C—($C_{1-6}$-alkoxy), C-halo and N;
$X_{10}$ and $X_{11}$ are each independently selected from:
  CH, C—($C_{1-6}$-alkyl), C—($C_{1-6}$-alkoxy), C-halo, N and $R_{10}$;
$X_{19}$ is selected from:
  CH, C—($C_{1-6}$-alkyl), C—($C_{1-6}$-alkoxy), C—C(O)NH$_2$, C—C(O)NH($C_{1-6}$-alkyl), C—C(O)N($C_{1-6}$-alkyl)$_2$, C-halo and N;
$X_{18}$ is selected from:
  CH, C—($C_{1-6}$-alkyl), C—($C_{1-6}$-alkoxy), C—NH$_2$, C—N($C_{1-6}$-alkyl)$_2$, C—NH($C_{1-6}$-alkyl), C—NHC(O)$C_{1-6}$-alkyl, C-halo and N;
  or when $X_{19}$ is CH, C—($C_{1-6}$-alkyl), or C-halo then $X_{18}$ may additionally be selected from C—C(O)NH$_2$ and C—C(O)N($C_{1-6}$-alkyl)$_2$;
$X_{13}$ and $X_{17}$ are each independently selected from:
  O, S, NH and N—($C_{1-6}$-alkyl);
$X_{22}$ and $X_{24}$ are each independently selected from:
  CH$_2$, CH—($C_{1-6}$-alkyl), O, S, NH, NMe and ⟩C═O;
$X_{23}$ is selected from:
  CH$_2$, CH—($C_{1-6}$-alkyl), C—($C_{1-6}$-alkyl)$_2$, NH and NMe;
  or when either $X_{22}$ or $X_{24}$ are other than ⟩C═O then $X_{23}$ may additionally be ⟩C═O or ⟩S(O)$_2$;
$X_{25}$ is selected from:
  O, S, NH and N($C_{1-6}$-alkyl);

$X_{26}$, $X_{27}$, $X_{28}$ and $X_{29}$ are each independently selected from:
CH, C—($C_{1-6}$-alkyl), C—($C_{1-6}$-alkoxy), C—OH, C-halo and N;
such that a maximum of two of $X_{26}$, $X_{27}$, $X_{28}$ and $X_{29}$ are selected from C—($C_{1-6}$-alkoxy), C—OH, C-halo and N;
$X_{30}$ is selected from:
$CH_2$, $CH_2CH_2$, NH, NMe, O, S and $\rangle$C=O;
$X_{31}$ is selected from:
$CH_2$, NH and NMe;
or when $X_{30}$ is other than $\rangle$C=O, O or S then $X_{31}$ may additionally be $\rangle$C=O or O;
$X_{32}$ is selected from:
$CH_2$, $CH_2CH_2$, NH, NMe and $\rangle$C=O,
$X_{33}$ is selected from:
$CH_2$, NH and NMe;
or when $X_{32}$ is other than $\rangle$C=O then $X_{33}$ may additionally be $\rangle$C=O or O;
$X_{34}$ is selected from:
NH and NMe;
$R_{10}$ is selected from:

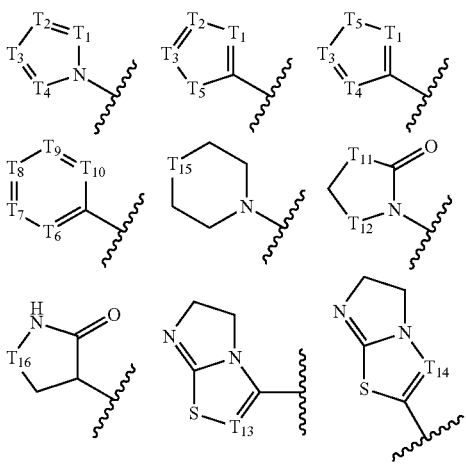

wherein:
$T_1$, $T_2$, $T_3$ and $T_4$ are each independently selected from:
CH, C—($C_{1-6}$-alkyl), C—($C_{1-6}$-alkoxy), C—$NH_2$, C—NH($C_{1-6}$-alkyl), C—N($C_{1-6}$-alkyl)$_2$, C-halo and N;
such that a maximum of one of $T_1$, $T_2$, $T_3$ and $T_4$ is C—($C_{1-6}$-alkoxy), C—$NH_2$, C—NH($C_{1-6}$-alkyl), C—N($C_{1-6}$-alkyl)$_2$ or C-halo;
$T_5$ is selected from:
O, S, NH and N($C_{1-6}$-alkyl);
$T_6$, $T_7$, $T_8$, $T_9$ and $T_{10}$ are each independently selected from:
CH, C—($C_{1-6}$-alkyl), C—($C_{1-6}$-alkoxy), C—$NH_2$, C—NH($C_{1-6}$-alkyl), C—N($C_{1-6}$-alkyl)$_2$, C-halo and N;
such that a maximum of two of $T_6$, $T_7$, $T_8$, $T_9$ and $T_{10}$ are selected from C—($C_{1-6}$-alkoxy), C—$NH_2$, C—NH($C_{1-6}$-alkyl), C—N($C_{1-6}$-alkyl)$_2$, C-halo and N;
$T_{11}$ is selected from:
$CH_2$, NH and N($C_{1-6}$-alkyl),
$T_{12}$ is selected from:
$CH_2$, NH, N($C_{1-6}$-alkyl) and $\rangle$C=O;

$T_{13}$ and $T_{14}$ are each independently selected from:
CH, C—($C_{1-6}$-alkyl) and C-halo;
$T_{15}$ is selected from:
O, NH and N($C_{1-6}$-alkyl);
$T_{16}$ is selected from:
$CH_2$ and $\rangle$C=O;
or $R_{10}$ is selected from:
H, $C_{1-6}$-alkyl, OH, $C_{1-6}$-alkoxy, $NO_2$, halo, CN, C(O)$NH_2$, C(O)NH($C_{1-6}$-alkyl), C(O)N($C_{1-6}$-alkyl)$_2$, C(O)NH($C_{3-6}$-cycloalkyl), S(O)$_2$$NH_2$, S(O)$_2$($C_{1-6}$-alkyl), S(O)$_2$NH($C_{1-6}$-alkyl), S(O)$_2$N($C_{1-6}$-alkyl)$_2$, S(O)$_2$NH($C_{3-6}$-cycloalkyl) and $(CH_2)_n$—$NR^{11}R^{12}$;
wherein n is 0 or 1;
and $R^{11}$ is selected from $C_{1-6}$-alkyl, C(O)$C_{1-6}$-alkyl, C(O)($C_{3-6}$-cycloalkyl), C(O)(aryl), C(O)$NH_2$, C(O)NH($C_{1-6}$-alkyl), C(O)N($C_{1-6}$-alkyl)$_2$, C(O)NH($C_{3-6}$-cycloalkyl), C(O)O($C_{1-6}$-alkyl), C(O)O($C_{3-6}$-cycloalkyl), C(O)O(aryl), S(O)$_2$($C_{1-6}$-alkyl), S(O)$_2$($C_{3-6}$-cycloalkyl), S(O)$_2$$NH_2$, S(O)$_2$NH($C_{1-6}$-alkyl), S(O)$_2$N($C_{1-6}$-alkyl)$_2$, S(O)$_2$NH($C_{3-6}$-cycloalkyl) and S(O)$_2$(aryl);
and $R^{12}$ is selected from H and $C_{1-6}$-alkyl;
$R_{13}$ is selected from:
C(O)$NH_2$, C(O)NH($C_{1-6}$-alkyl), C(O)N($C_{1-6}$-alkyl)$_2$, C(O)NH($C_{3-6}$-cycloalkyl), S(O)$_2$$NH_2$, S(O)$_2$($C_{1-6}$-alkyl), S(O)$_2$NH($C_{1-6}$-alkyl), S(O)$_2$N($C_{1-6}$-alkyl)$_2$, S(O)$_2$NH($C_{3-6}$-cycloalkyl) and $(CH_2)_n$—$NR^{14}R^{15}$;
wherein n is 0 or 1;
and $R^{14}$ is selected from H, $C_{1-6}$-alkyl, C(O)$C_{1-6}$-alkyl, C(O)($C_{3-6}$-cycloalkyl), C(O)(aryl), C(O)$NH_2$, C(O)NH($C_{1-6}$-alkyl), C(O)N($C_{1-6}$-alkyl)$_2$, C(O)NH($C_{3-6}$-cycloalkyl), C(O)O($C_{1-6}$-alkyl), C(O)O($C_{3-6}$-cycloalkyl), C(O)O(aryl), S(O)$_2$($C_{1-6}$-alkyl), S(O)$_2$($C_{3-6}$-cycloalkyl), S(O)$_2$$NH_2$, S(O)$_2$NH($C_{1-6}$-alkyl), S(O)$_2$N($C_{1-6}$-alkyl)$_2$, S(O)$_2$NH($C_{3-6}$-cycloalkyl) and S(O)$_2$(aryl);
and $R^{15}$ is selected from H and $C_{1-6}$-alkyl.

2. A compound according to claim 1 wherein:
$R^3$ is selected from cyclopentyl or cyclohexyl;
$X_1$, $X_2$, $X_3$, $X_4$, $X_{14}$, $X_{15}$, $X_{16}$ and $X_{20}$ are independently selected from:
CH, CMe, C—OMe, C—F, C—Cl and N:
such that a maximum of two of $X_1$, $X_2$, $X_3$, $X_4$, $X_{14}$, $X_{15}$, $X_{16}$ and $X_{20}$ are chosen as N or C—Cl or C—OMe;
$X_5$, $X_6$, $X_7$ and $X_8$ are independently selected from:
CH, CMe, C—OMe, C—F, C—Cl, N and OH;
such that a maximum of one of $X_5$, $X_6$, $X_7$ and $X_8$ is chosen as N or C—Cl or C—OH or C—OMe;
$X_9$ and $X_{12}$ are independently selected from:
CH, CMe, C—OMe, C—F, C—Cl and N;
$X_{10}$ and $X_{11}$ are independently selected from:
CH, CMe, C—OMe, C—F, C—Cl, N and $R_{10}$;
$X_{19}$ is selected from:
CH, CMe, C—OMe, C—C(O)$NH_2$, C—C(O)$NMe_2$, C—F, C—Cl and N;
$X_{18}$ is selected from:
CH, CMe, C—OMe, C—$NH_2$, C—$NMe_2$, C—NHMe, C—NHC(O)Me, C—F, C—Cl and N;
or when $X_{19}$ is CH, CMe or C—F then $X_{18}$ may additionally be selected from C—C(O)$NH_2$ and C—C(O)$NMe_2$;
$X_{13}$ and $X_{17}$ are independently selected from:
O, S, NH and NMe;
$X_{22}$ and $X_{24}$ are independently selected from:
$CH_2$, CHMe, O, S, NH, NMe and $\rangle$C=O;
$X_{23}$ is selected from:
$CH_2$, CHMe, $CMe_2$, NH and NMe;

or when either $X_{22}$ or $X_{24}$ are other than $\rangle C=O$ then $X_{23}$ may additionally be $\rangle C=O$ or $\rangle S(O)_2$;

$X_{25}$ is selected from:
O, S, NH and NMe;

$X_{26}$, $X_{27}$, $X_{28}$ and $X_{29}$ are independently selected from:
CH, CMe, C—OMe, C—F, C—Cl, C—Br and N;

such that a maximum of two of $X_{26}$, $X_{27}$, $X_{28}$ and $X_{29}$ are chosen as C—OMe, C—Cl, C—Br and N;

$X_{30}$ is selected from:
$CH_2$, $CH_2CH_2$, NH, NMe, O, S and $\rangle C=O$;

$X_{31}$ is selected from:
$CH_2$, NH, and NMe;

or when $X_{30}$ is other than $\rangle C=O$, O or S then $X_{31}$ may additionally be $\rangle C=O$ or O;

$X_{32}$ is selected from:
$CH_2$, NH, NMe and $\rangle C=O$;

$X_{33}$ is selected from:
$CH_2$, NH and NMe;

or when $X_{32}$ is other than $\rangle C=O$ then $X_{33}$ may additionally be $\rangle C=O$ or O;

$X_{34}$ is selected from:
NH and NMe;

$T_1$, $T_2$, $T_3$ and $T_4$ are independently selected from:
CH, CMe, C—OMe, C—$NH_2$, C—NHMe, C-$NMe_2$, C—F, C—Cl and N;

such that a maximum of one of $T_1$, $T_2$, $T_3$ and $T_4$ is chosen as C—OMe, C—$NH_2$, C—NHMe, C—$NMe_2$, C—F and C—Cl;

$T_5$ is selected from:
O, S, NH and NMe;

$T_6$, $T_7$, $T_8$, $T_9$ and $T_{10}$ are independently selected from:
CH, CMe, C—OMe, C—$NH_2$, C—NHMe, C—$NMe_2$, C—F, C—Cl and N;

such that a maximum of two of $T_6$, $T_7$, $T_8$, $T_9$ and $T_{10}$ are chosen as C—OMe, C—$NH_2$, C—NHMe, C—$NMe_2$, C—F, C—Cl and N;

$T_{11}$ is selected from:
$CH_2$, NH and NMe;

$T_{12}$ is selected from:
$CH_2$, NH, NMe and $\rangle C=O$;

$T_{13}$ and $T_{14}$ are independently selected from:
CH, CMe, C—F and C—Cl;

$T_{15}$ is selected from:
O, NH and NMe;

$T_{16}$ is selected from:
$CH_2$ and $\rangle C=O$;

or $R_{10}$ is selected from:
H, Me, OH, OMe, OEt, OiPr, $NO_2$, F, Cl, Br, CN, C(O)$NH_2$, C(O)NHMe, C(O)$NMe_2$, and $(CH_2)_n$—$NR^{11}R^{12}$;

wherein n=0 or 1;

and $R^{11}$ is selected from H, Me, acetyl, C(O)$NH_2$, C(O)$NMe_2$;

and $R^{12}$ is selected from H and Me;

$R_{13}$ is selected from:
C(O)$NH_2$, C(O)NHMe, C(O)N(Me)$_2$, C(O)NH(cyclopropyl), S(O)$_2NH_2$, S(O)$_2$(Me), S(O)$_2$NH(Me), S(O)$_2$N(Me)$_2$, S(O)$_2$NH(cyclopropyl) and $(CH_2)_n$—$NR^{14}R^{15}$;

wherein n is 0 or 1;

and $R^{14}$ is selected from H, Me, C(O)Me, C(O)Et, C(O)(cyclopropyl), C(O)Ph, C(O)$NH_2$, C(O)NH(Me), C(O)N(Me)$_2$, C(O)NH(cyclopropyl), C(O)O(Me), C(O)O(cyclopropyl), C(O)OPh, S(O)$_2$(Me), —S(O)$_2$(cyclopropyl), S(O)$_2NH_2$, S(O)$_2$NH(Me), S(O)$_2$N(Me)$_2$, S(O)$_2$NH(cyclopropyl) and S(O)$_2$Ph;

and $R^{15}$ is selected from H and Me.

3. A compound according to claim 1 wherein $R^3$ is cyclopentyl.

4. A compound according to claim 1 wherein $R^3$ is cyclohexyl.

5. A compound according to claim 1 which is of formula Ia, wherein $X_1$, $X_2$, $X_3$, $X_4$, $X_5$, $X_6$, $X_7$, $X_8$, $X_9$, $X_{10}$, $X_{11}$, $X_{13}$, $X_{14}$, $X_{15}$, $X_{16}$, $X_{17}$, $X_{18}$, $X_{19}$, $X_{22}$, $X_{23}$, $X_{24}$, $X_{25}$, $X_{30}$, $X_{31}$, $X_{34}$, $R_{10}$ and $R_{13}$ are as defined in claim 1.

6. A compound according to claim 1 which is of formula Ib,

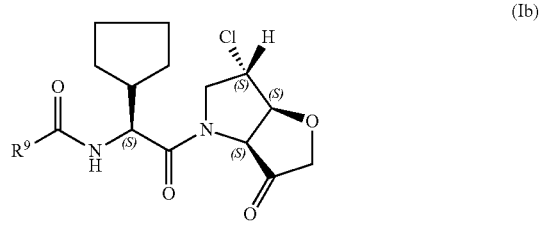

(Ib)

wherein $R^9$ is as defined in claim 1.

7. A compound according to claim 1 wherein $R^9$ is selected from:

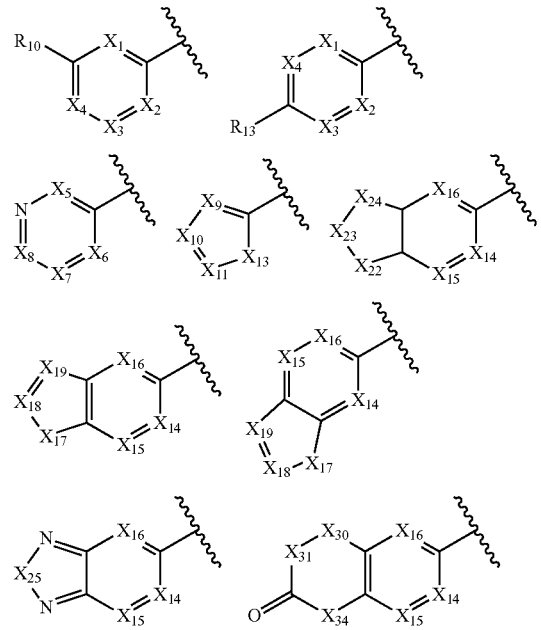

wherein aryl, $X_2$, $X_3$, $X_{18}$, $X_{19}$, $X_{22}$, $X_{24}$, $X_{30}$ and $X_{31}$ are as defined in claim 1 and;

$R^{14}$ is selected from C(O)Me, C(O)Et, C(O)(cyclopropyl), C(O)$NH_2$, C(O)NH(Me), C(O)N(Me)$_2$, C(O)NH(cyclopropyl), C(O)O(Me), C(O)O(cyclopropyl), S(O)$_2$(Me), S(O)$_2$(cyclopropyl), S(O)$_2NH_2$, S(O)$_2$NH(Me), S(O)$_2$N(Me)$_2$, S(O)$_2$NH(cyclopropyl) and S(O)$_2$Ph.

8. A compound according to claim 1 wherein $R^9$ is selected from:
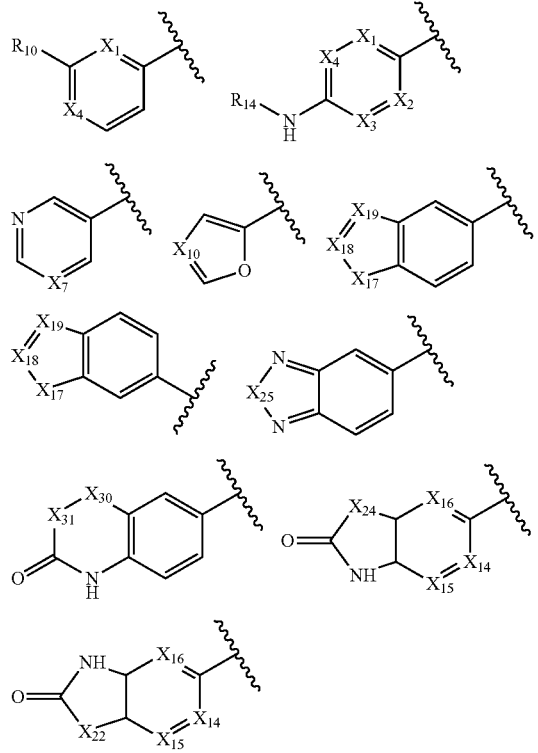
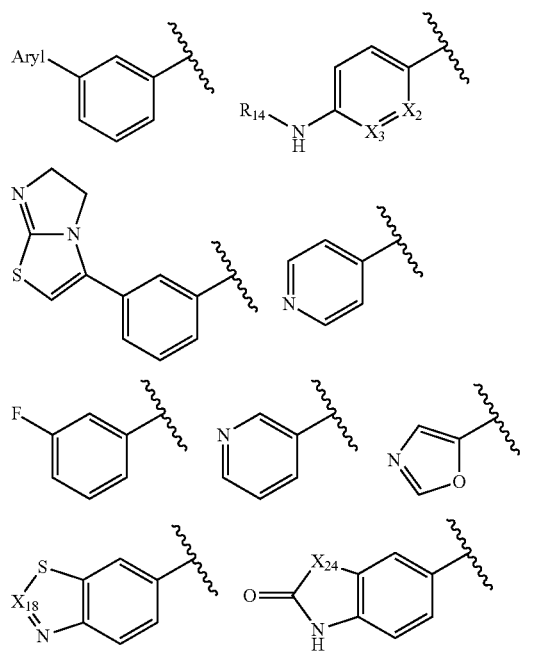
wherein $X_1$, $X_2$, $X_3$, $X_4$, $X_7$, $X_{10}$, $X_{17}$, $X_{18}$, $X_{19}$, $X_{22}$, $X_{24}$, $X_{25}$, $X_{30}$, $X_{31}$, $R_{10}$ and $R_{14}$ are as defined in claim 1.
9. A compound according to claim 1 wherein $R^9$ is selected from:
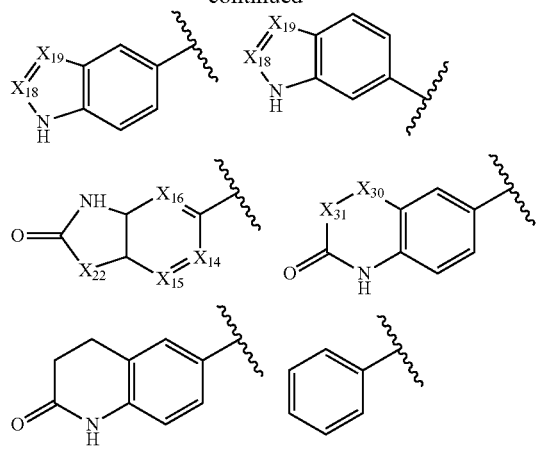
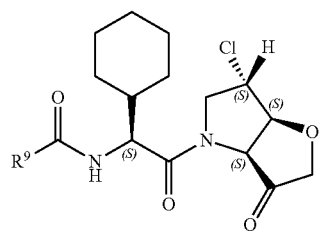
(Ia)
wherein $R^9$ is as defined in claim 1.
10. A compound according to claim 1 wherein $R^9$ is selected from:
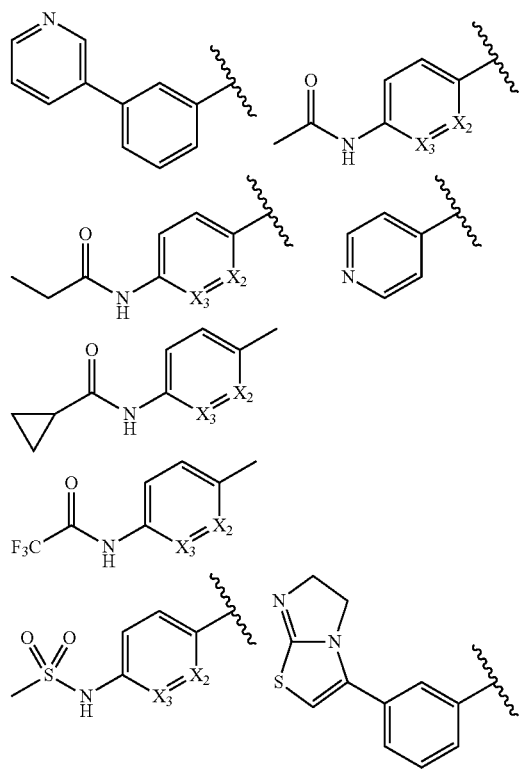

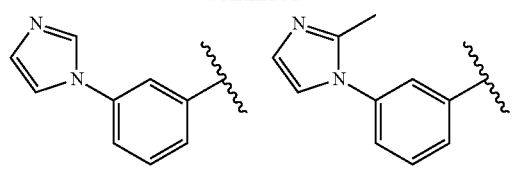
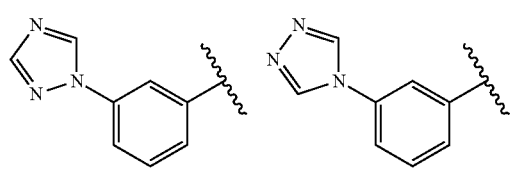
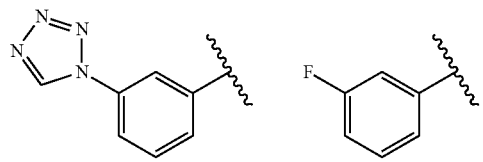
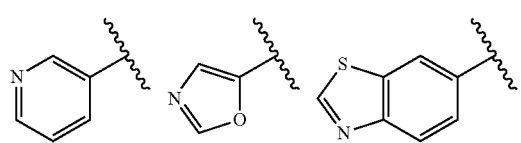
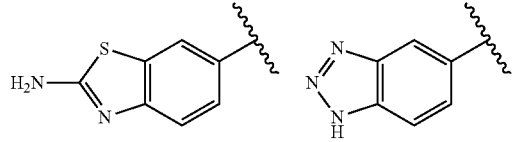
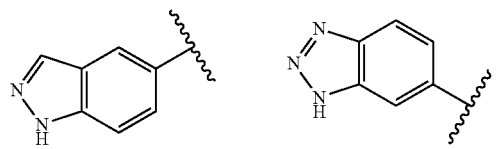
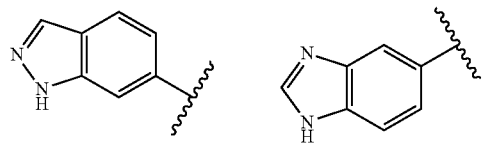
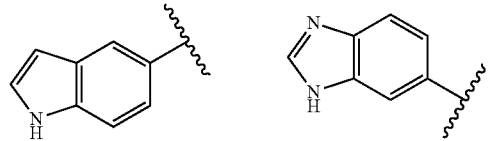
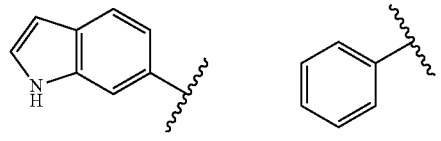
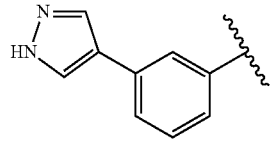
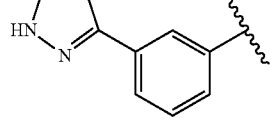
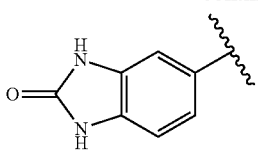
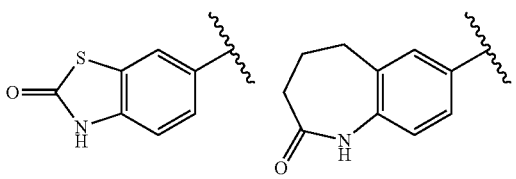
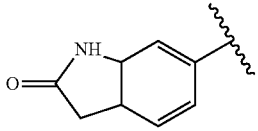
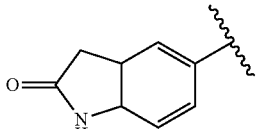
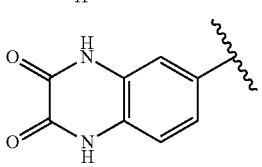
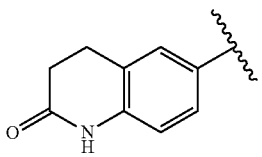
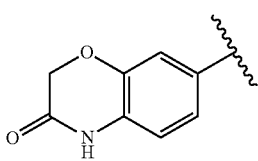
wherein $X_2$ and $X_3$ are as defined in claim 1.
11. A compound according to claim 1 wherein $R^9$ is selected from:
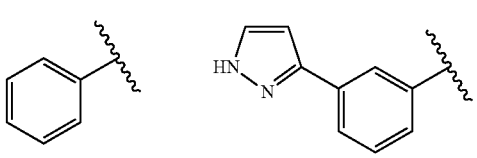
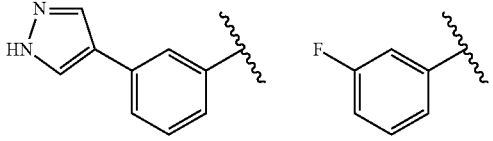
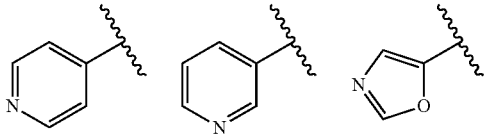

12. A compound according to claim 1 which is selected from the following:

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)nicotinamide;

N—((S)-2-((3aS,6S,6aS)-6-chloro-3-oxodihydro-2H-furo[3,2-t]pyrrol-4(5H,6H,6aH)-yl)-1-cyclohexyl-2-oxoethyl)-3-(1H-tetrazol-1-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)isonicotinamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-fluorobenzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-imidazol-1-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(2-methyl-1H-imidazol-1-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(pyridin-3-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(5,6-dihydroimidazo[2,1-b]thiazol-3-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indole-5-carboxamide;

N—((S)-2-((3aS,6S,6aS)-6-chloro-3-oxodihydro-2H-furo[3,2-b]pyrrol-4 (5H,6H,6aH)-yl)-1-cyclohexyl-2-oxoethyl)-3-(1H-pyrazol-4-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-pyrazol-3-yl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-benzo[d][1,2,3]triazole-6-carboxamide;

2-Amino-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indazole-6-carboxamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)oxazole-5-carboxamide;

N—((S)-2-((3aS,6S,6aS)-6-chloro-3-oxodihydro-2H-furo[3,2-t]pyrrol-4(5H,6H,6aH)-yl)-1-cyclohexyl-2-oxoethyl)-2,3-dioxo-1,2,3,4-tetrahydroquinoxaline-6-carboxamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-1,2,3,4-tetrahydroquinoline-6-carboxamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-5-carboxamide;

N—((S)-2-((3aS,6S,6aS)-6-chloro-3-oxodihydro-2H-furo[3,2-t]pyrrol-4(5H,6H,6aH)-yl)-1-cyclohexyl-2-oxoethyl)-2-oxoindoline-6-carboxamide;

4-Acetamido-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(cyclopropanecarboxamido) benzamide;

N—((S)-2-((3aS,6S,6aS)-6-chloro-3-oxodihydro-2H-furo[3,2-b]pyrrol-4 (5H,6H,6aH)-yl)-1-cyclohexyl-2-oxoethyl)-4-(methylsulfonamido)benzamide;

N—((S)-2-((3aS,6S,6aS)-6-chloro-3-oxodihydro-2H-furo[3,2-b]pyrrol-4 (5H,6H,6aH)-yl)-1-cyclohexyl-2-oxoethyl)-2-oxo-2,3-dihydro-1H-benzo[d]imidazole-5-carboxamide;

N—((S)-2-((3aS,6S,6aS)-6-chloro-3-oxodihydro-2H-furo[3,2-t]pyrrol-4(5H,6H,6aH)-yl)-1-cyclohexyl-2-oxoethyl)-2-oxo-2,3-dihydrobenzo[d]thiazole-6-carboxamide;

N—((S)-2-((3aS,6S,6aS)-6-chloro-3-oxodihydro-2H-furo[3,2-b]pyrrol-4 (5H,6H,6aH)-yl)-1-cyclohexyl-2-oxoethyl)-2-oxo-2,3,4,5-tetrahydro-1H-benzo[b]azepine-7-carboxamide;

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-oxo-3,4-dihydro-2H-benzo[b][1,4]oxazine-7-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)nicotinamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-tetrazol-1-yl)benzamide;

N—((S)-2-((3aS,6S,6aS)-6-chloro-3-oxodihydro-2H-furo[3,2-b]pyrrol-4 (5H,6H,6aH)-yl)-1-cyclopentyl-2-oxoethyl)isonicotinamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-fluorobenzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-imidazol-1-yl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(2-methyl-1H-imidazol-1-yl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(pyridin-3-yl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzo[d]thiazole-6-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(5,6-dihydroimidazo[2,1-b]thiazol-3-yl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-indole-5-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-pyrazol-4-yl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-pyrazol-3-yl)benzamide;

N—((S)-2-((3aS,6S,6aS)-6-chloro-3-oxodihydro-2H-furo[3,2-t]pyrrol-4 (5H,6H,6aH)-yl)-1-cyclopentyl-2-oxoethyl)-1H-benzo[d][1,2,3]triazole-6-carboxamide;

2-Amino-N—((S)-2-((3aS,6S,6aS)-6-chloro-3-oxodihydro-2H-furo[3,2-b]pyrrol-14(5H,6H,6aH)-yl)-1-cyclopentyl-2-oxoethyl)benzo[d]thiazole-6-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-indazole-6-carboxamide;

N—((S)-2-((3aS,6S,6aS)-6-chloro-3-oxodihydro-2H-furo[3,2-b]pyrrol-4 (5H,6H,6aH)-yl)-1-cyclopentyl-2-oxoethyl)oxazole-5-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-1,2,3,4-tetrahydroquinoline-6-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-5-carboxamide;

N—((S)-2-((3aS,6S,6aS)-6-chloro-3-oxodihydro-2H-furo[3,2-b]pyrrol-4 (5H,6H,6aH)-yl)-1-cyclopentyl-2-oxoethyl)-2-oxoindoline-6-carboxamide;

4-Acetamido-N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(cyclopropanecarboxamido) benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(methylsulfonamido)benzamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydro-1H-benzo[d]imidazole-5-carboxamid %

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydrobenzo[d]thiazole-6-carboxamide;

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3,4,5-tetrahydro-1H-benzo[b]azepine-7-carboxamide; and N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-oxo-3,4-dihydro-2H-benzo[b][1,4]oxazine-7-carboxamide.

13. A compound according to claim 12 which is selected from the following:

N—((S)-2-((3aS,6S,6aS)-6-chloro-3-oxodihydro-2H-furo[3,2-b]pyrrol-4 (5H,6H,6aH)-yl)-1-cyclohexyl-2-oxoethyl)benzamide [1];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-tetrazol-1-yl)benzamide [2];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-imidazol-1-yl)benzamide [3];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-imidazol-1-yl)benzamide [4];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide [5];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(5,6-dihydroimidazo[2,1-b]thiazol-3-yl)benzamide [6];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-pyrazol-4-yl)benzamide [7];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-benzo[d][1,2,3]triazole-6-carboxamide [8];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-benzo[d][1,2,3]triazole-6-carboxamide [9];

2-Amino-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide [10];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)oxazole-5-carboxamide [11];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indazole-6-carboxamide [12];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-pyrazol-4-yl)benzamide [13];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)nicotinamide [14];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)isonicotinamide [15];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-fluorobenzamide [16];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(pyridin-3-yl)benzamide [17];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2,3-dioxo-1,2,3,4-tetrahydroquinoxaline-6-carboxamide [18];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide [19];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-1,2,3,4-tetrahydroquinoline-6-carboxamide [20];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide [21];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-5-carboxamide [22];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-5-carboxamide [23];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-6-carboxamide [24];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-6-carboxamide [25];

4-Acetamido-N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide [26];

4-Acetamido-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide [27];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(cyclopropanecarboxamido) benzamide [28];

N—((S)-2-((3aS,6S,6aS)-6-chloro-3-oxodihydro-2H-furo[3,2-b]pyrrol-4(5H,6H,6a-yl)-1-cyclohexyl-2-oxoethyl)-4-(cyclopropanecarboxamido) benzamide[29];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(methylsulfonamido)benzamide [30];

N—((S)-2-((3aS,6S,6aS)-6-chloro-3-oxodihydro-2H-furo[3,2-b]pyrrol-4(5H,6H,6a-yl)-1-cyclohexyl-2-oxoethyl)-4-(methylsulfonamido)benzamide [31];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydro-1H-benzo[d]imidazole-5-carboxamide [32];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydro-1H-benzo[d]imidazole-5-carboxamide [33];

N—((S)-2-((3aS,6S,6aS)-6-chloro-3-oxodihydro-2H-furo[3,2-t]pyrrol-4(5H,6H,6aH)-yl)-1-cyclopentyl-2-oxoethyl)-2-oxo-2,3-dihydrobenzo[d]thiazole-6-carboxamide [34];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydrobenzo[d]thiazole-6-carboxamide [35];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3,4,5-tetrahydro-1H-benzo[b]azepine-7-carboxamide [36], N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3,4,5-tetrahydro-1H-benzo[b]azepine-7-carboxamide [37], N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-oxo-3,4-dihydro-2H-benzo[b][1,4]oxazine-7-carboxamide [38]; and N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-oxo-3,4-dihydro-2H-benzo[b][1,4]oxazine-7-carboxamide [39].

14. A compound according to claim 13 which is selected from the following:

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-tetrazol-1-yl)benzamide [2];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(1H-imidazol-1-yl)benzamide [3];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(1H-imidazol-1-yl)benzamide [4];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide [5];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-(5,6-dihydroimidazo[2,1-b]thiazol-3-yl)benzamide [6];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-1H-benzo[d][1,2,3]triazole-6-carboxamide [9];

2-Amino-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzo[d]thiazole-6-carboxamide [10];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-1H-indazole-6-carboxamide [12];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)nicotinamide [14];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)isonicotinamide [15];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-fluorobenzamide [16];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-(pyridin-3-yl)benzamide [17];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2,3-dioxo-1,2,3,4-tetrahydroquinoxaline-6-carboxamide [18];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide [19];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-1,2,3,4-tetrahydroquinoline-6-carboxamide [20];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2,3-dioxo-1,2,3,4-tetrahydroquinoxaline-6-carboxamide [21];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-5-carboxamide [22];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-5-carboxamide [23];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxoindoline-6-carboxamide [24];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxoindoline-6-carboxamide [25];

4-Acetamido-N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)benzamide [26];

4-Acetamido-N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)benzamide [27];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(cyclopropanecarboxamido) benzamide [28];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(cyclopropanecarboxamido) benzamide [29];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-4-(methylsulfonamido)benzamide [30];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-4-(methylsulfonamido)benzamide [31];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydro-1H-benzo[d]imidazole-5-carboxamide [32];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydro-1H-benzo[d]imidazole-5-carboxamide [33];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3-dihydrobenzo[d]thiazole-6-carboxamide [34];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3-dihydrobenzo[d]thiazole-6-carboxamide [35];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-2-oxo-2,3,4,5-tetrahydro-1H-benzo[b]azepine-7-carboxamide [36];

N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-2-oxo-2,3,4,5-tetrahydro-1H-benzo[b]azepine-7-carboxamide [37];

N—((S)-2-((3aS,6S,6aS)-6-chloro-3-oxodihydro-2H-furo[3,2-b]pyrrol-4(5H,6H,6aH)-yl)-1-cyclopentyl-2-oxoethyl)-3-oxo-3,4-dihydro-2H-benzo[b][1,4]oxazine-7-carboxamide [38]; and N—((S)-2-((3aS,6S,6aS)-6-chloro-3-oxodihydro-2H-furo[3,2-b]pyrrol-4(5H,6H,6aH)-yl)-1-cyclohexyl-2-oxoethyl)-3-oxo-3,4-dihydro-2H-benzo[b][1,4]oxazine-7-carboxamide [39].

15. A pharmaceutical or veterinary composition comprising a compound according to claim 1 and a pharmaceutically acceptable or veterinarily acceptable diluent, excipient and/or carrier.

16. A process for preparing a pharmaceutical or veterinary composition, said process comprising admixing a compound according to claim 1 with a pharmaceutically acceptable or veterinarily acceptable diluent, excipient and/or carrier.

17. A method of inhibiting a cysteine proteinase in a cell, said method comprising contacting said cell with a compound according claim 1.

18. A method of inhibiting a cysteine proteinase in a subject, said method comprising administering to the subject a pharmacologically effective amount of a compound according to claim 1.

19. A method according to claim 17 wherein the cysteine proteinase is a CAC1 cysteine proteinase.

20. A method according to claim 19 wherein the CAC1 cysteine proteinases are cathepsin S and cathepsin K.

21. A method of treating a disease selected from rheumatoid arthritis, osteoarthritis, chronic obstructive pulmonary disease (COPD), atherosclerosis, cardiovascular diseases which exhibit damage and remodeling of extracellular matrix (ECM) and chronic pain, in a subject, said method comprising administering to the subject a pharmacologically effective amount of a compound according to claim 1.

22. A method of validating a known or putative cysteine proteinase as a therapeutic target, the method comprising:
    (a) assessing the in vitro binding of a compound according to claim 1 to an isolated or known putative cysteine proteinase, providing a measure of potency; and optionally, one or more of the steps of:
    (b) assessing the binding of a compound according to claim 1 to closely related homologous proteinases of the target and general housekeeping proteinases to provide a measure of selectivity;
    (c) monitoring a cell-based functional marker of a particular cysteine proteinase activity in the presence of a compound according to claim 1; and
    (d) monitoring an animal model-based functional marker of a particular cysteine proteinase activity in the presence of a compound according to claim 1.

23. A process of preparing a compound according to claim 1, said process comprising treating a compound of formula (II) with an oxidizing agent,

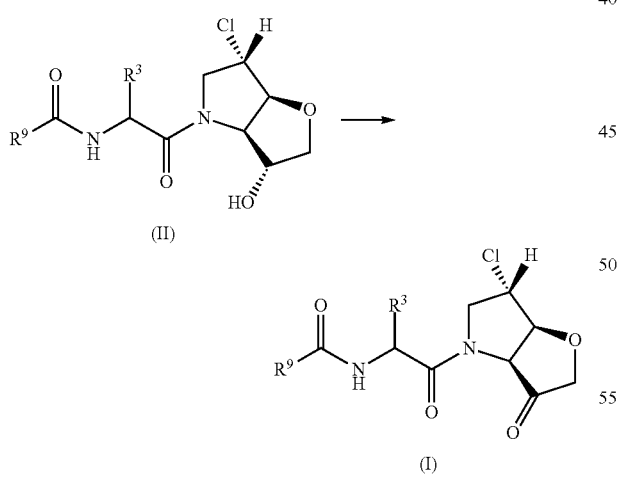

wherein $R^9$ is as defined in claim 1.

24. A process according to claim 23 wherein the oxidizing agent is Dess-Martin periodinane.

25. A process according to claim 23 which comprises the step of converting a compound of formula (III), where $R^5$ is a protecting group or hydrogen, into a compound of formula (II), by treating a compound of formula (IIIa) ($R^5$=H) with a compound of formula $R^9$CONHCH($R^3$)COOH

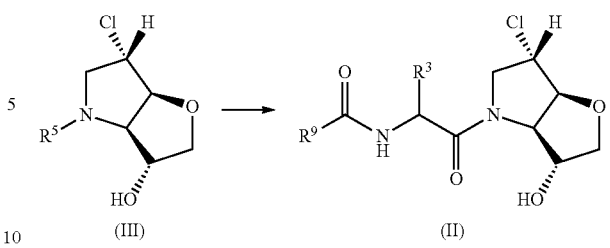

where $R^5$ is a protecting group or hydrogen.

26. A process according to claim 25 wherein protecting group $R^5$ is selected from benzyloxycarbonyl, tert-butoxycarbonyl, fluoren-9-ylmethoxycarbonyl, 1-(biphenyl-4-yl)-1-methylethoxycarbonyl, α,α-dimethyl-3,5-dimethoxylbenzyloxycarbonyl, p-methoxybenzyloxycarbonyl, p-nitrobenzyloxycarbonyl, allyloxycarbonyl and trichloroethoxycarbonyl.

27. A process according to claim 25 which comprises the step of converting a compound of formula (IV) into a compound of formula (III; $R^5$=H)

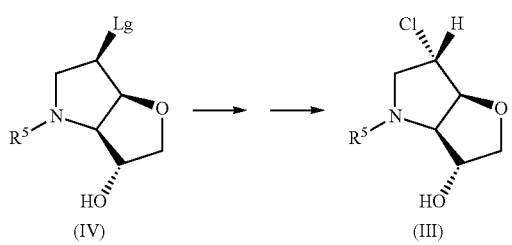

where Lg is a leaving group such as tosylate or mesylate and $R^5$ is as defined in claim 25.

28. A process according to claim 27 which comprises the step of converting a compound of formula (IVa; $R^5$=H) into a compound of formula (IIIa) or a compound of formula (IVb; $R^5$=Cbz) into a compound of formula (IIIb)

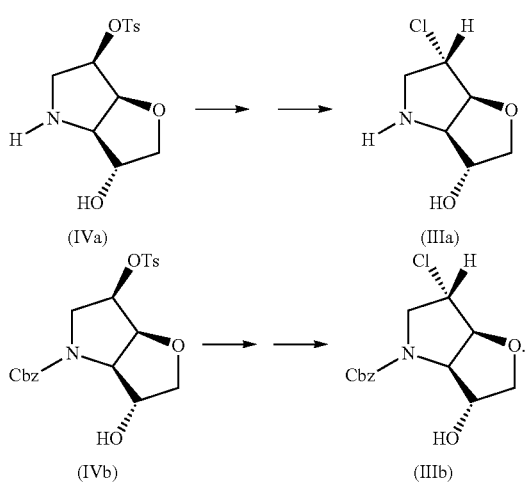

29. A process according to claim 27 which comprises the step of converting a compound of formula (V) into a compound of formula (IV)

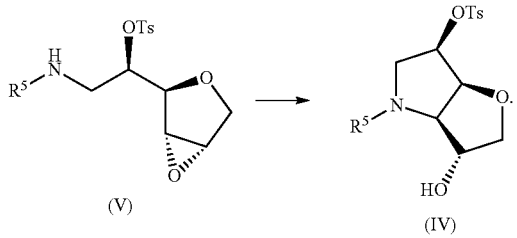

30. A process according to claim 29 wherein $R^5$ is benzyloxycarbonyl (Cbz), and the process comprises hydrogenating a compound of formula (V) in the presence of a palladium catalyst.

31. A process according to claim 29 which comprises the step of converting a compound of formula (VI) into a compound of formula (V) by treating said compound of formula (VI) with an oxidizing agent

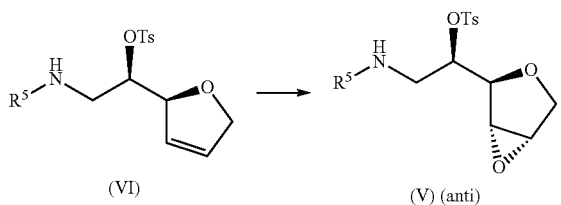

32. A process according to claim 31 wherein the oxidising agent is mCPBA or a dioxirane.

33. A process according to claim 31 which comprises the step of converting a compound of formula (VII) into a compound of formula (VI)

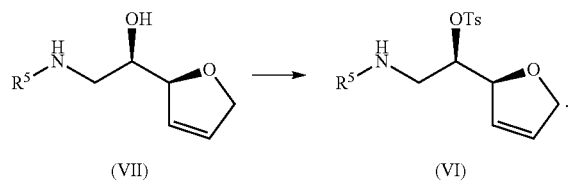

34. A process according to claim 33 which comprises treating a compound of formula (VII) with (a) tosyl chloride in pyridine, or (b) tosyl chloride in dichloromethane and triethylamine.

35. A process according to claim 33 which comprises the step of converting a compound of formula (VIII) into a compound of formula (VII)

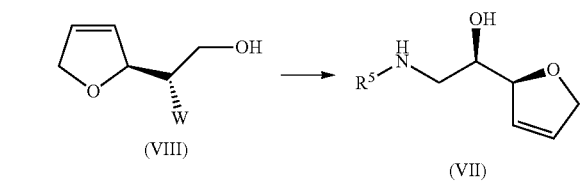

where W is halogen or tosyl.

36. A process according to claim 35 which comprises the steps of:
 (a) reacting a compound of formula (VIII), where W is halogen or OTs, with aqueous ammonia and alcohol; and
 (b) converting the product formed in step (a) to a compound of formula (VII).

37. A process according to claim 36 wherein steps (a) and (b) are carried out in a one-pot process.

38. A process according to claim 35 wherein said compound of formula VIII is prepared from a compound of formula IX

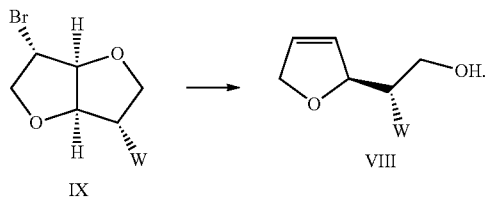

39. A process according to claim 38 which comprises treating said compound of formula IX with zinc in aqueous isopropanol.

* * * * *